(12) United States Patent
Garibaldi et al.

(10) Patent No.: US 11,137,887 B1
(45) Date of Patent: *Oct. 5, 2021

(54) UNIFIED ECOSYSTEM EXPERIENCE FOR MANAGING MULTIPLE HEALTHCARE APPLICATIONS FROM A COMMON INTERFACE

(71) Applicant: Navvis & Company, LLC, St. Louis, MO (US)

(72) Inventors: Jeffrey Garibaldi, St. Louis, MO (US); Joshua Wilson, Nashville, TN (US)

(73) Assignee: NAVVIS & COMPANY, LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/126,646

(22) Filed: Dec. 18, 2020

Related U.S. Application Data

(60) Provisional application No. 62/961,530, filed on Jan. 15, 2020.

(51) Int. Cl.
*G06F 3/0484* (2013.01)
*G06F 9/451* (2018.01)
(Continued)

(52) U.S. Cl.
CPC .......... *G06F 3/04842* (2013.01); *G06F 9/451* (2018.02); *G06F 9/547* (2013.01);
(Continued)

(58) Field of Classification Search
CPC ...... G06F 3/04842; G06F 9/451; G06F 9/547; G06F 16/9574; G06F 16/9577; G16H 10/60
See application file for complete search history.

(56) References Cited

U.S. PATENT DOCUMENTS

D296,114 S   6/1988  Wells-Papanek et al.
5,301,326 A  4/1994  Linnett et al.
(Continued)

FOREIGN PATENT DOCUMENTS

CN   303718982        6/2016
CN   109343925 A      2/2019
(Continued)

OTHER PUBLICATIONS

FAQ for GoldenLayout-a multi-window javascript layout manager for webapps; downloaded Nov. 5, 2019 from http://golden-layout.com/faq/; 2 pages.

(Continued)

*Primary Examiner* — Eric J. Bycer
(74) *Attorney, Agent, or Firm* — Thompson Coburn LLP

(57) ABSTRACT

A browser-based, user interface served by a manager application providing for a unified ecosystem experience empowering healthcare users with seamless control over a plurality of different applications and/or websites in a maximized, consolidated and synchronized manner. The manager application includes a user interface with common toolbar controlling a plurality of panels built upon underlying frame data for displaying various applications and/or websites in a consolidated view. Therefore, a uniform user experience with consistent look-and-feel is provided despite using separate applications and/or websites.

58 Claims, 50 Drawing Sheets

(51) Int. Cl.
  *G16H 10/60* (2018.01)
  *G06F 16/957* (2019.01)
  *G06F 9/54* (2006.01)

(52) U.S. Cl.
  CPC ...... *G06F 16/9574* (2019.01); *G06F 16/9577* (2019.01); *G16H 10/60* (2018.01)

(56) References Cited

U.S. PATENT DOCUMENTS

| | | |
|---|---|---|
| 5,712,995 A | 1/1998 | Cohn |
| D397,999 S | 9/1998 | Kovanen et al. |
| D400,520 S | 11/1998 | Baker et al. |
| D414,758 S | 10/1999 | Hodgson |
| D418,120 S | 12/1999 | Okura et al. |
| D419,981 S | 2/2000 | Coleman |
| D422,580 S | 4/2000 | Faris et al. |
| D424,543 S | 5/2000 | Hodgson |
| D426,525 S | 6/2000 | Coleman |
| D427,979 S | 7/2000 | Li et al. |
| D433,392 S | 11/2000 | Hodgson |
| D436,967 S | 1/2001 | Yasui et al. |
| D445,427 S | 7/2001 | Faris et al. |
| 6,278,448 B1 | 8/2001 | Brown et al. |
| D447,751 S | 9/2001 | Hodgson |
| D450,058 S | 11/2001 | Istvan et al. |
| D453,936 S | 2/2002 | Istvan et al. |
| D453,937 S | 2/2002 | Wasko et al. |
| D460,762 S | 7/2002 | Wasko |
| D461,821 S | 8/2002 | Lindsay et al. |
| D469,444 S | 1/2003 | Ording et al. |
| D475,062 S | 5/2003 | Horie |
| D490,440 S | 5/2004 | Ording et al. |
| D491,955 S | 6/2004 | Ording et al. |
| D492,692 S | 7/2004 | Fallon et al. |
| 6,784,869 B1 | 8/2004 | Clark et al. |
| D501,211 S | 1/2005 | Ligameri et al. |
| D518,829 S | 4/2006 | Hally et al. |
| 7,117,452 B1 * | 10/2006 | Pavelski ................. G06F 9/451 715/792 |
| D539,808 S | 4/2007 | Cummins et al. |
| D540,339 S | 4/2007 | Cummins et al. |
| D540,342 S | 4/2007 | Cummins et al. |
| D544,878 S | 6/2007 | Cummins et al. |
| D545,829 S | 7/2007 | Fletcher |
| D550,688 S | 9/2007 | Cummins et al. |
| D551,240 S | 9/2007 | Cummins |
| D557,273 S | 12/2007 | Mar et al. |
| D562,842 S | 2/2008 | Cameron |
| D564,533 S | 3/2008 | Sadler et al. |
| D564,534 S | 3/2008 | Sadler et al. |
| D564,535 S | 3/2008 | Sadler et al. |
| D568,901 S | 5/2008 | Sadler et al. |
| D570,859 S | 6/2008 | Hsiao et al. |
| D571,819 S | 6/2008 | Scott et al. |
| D575,298 S | 8/2008 | Chen et al. |
| D592,221 S | 5/2009 | Rehling et al. |
| D594,013 S | 6/2009 | Singh et al. |
| D594,014 S | 6/2009 | Taylor et al. |
| D594,019 S | 6/2009 | Ball et al. |
| D604,313 S | 11/2009 | Hoefnagels et al. |
| D604,316 S | 11/2009 | Hoefnagels et al. |
| D607,463 S | 1/2010 | Krieter et al. |
| D628,211 S | 11/2010 | Ording et al. |
| 7,844,917 B2 * | 11/2010 | Rigolet ................. G06F 9/451 715/798 |
| D642,194 S | 7/2011 | Kozlowski et al. |
| D651,608 S | 1/2012 | Allen et al. |
| D652,424 S | 1/2012 | Cahill et al. |
| D653,671 S | 2/2012 | Cahill et al. |
| D658,200 S | 4/2012 | Gleasman et al. |
| D658,201 S | 4/2012 | Gleasman et al. |
| D658,675 S | 5/2012 | Gleasman et al. |
| D658,677 S | 5/2012 | Gleasman et al. |
| D664,558 S | 7/2012 | Tanghe et al. |
| D664,559 S | 7/2012 | Ismail et al. |
| D664,973 S | 8/2012 | Gleasman et al. |
| D664,974 S | 8/2012 | Gleasman et al. |
| D664,978 S | 8/2012 | Tanghe et al. |
| D664,979 S | 8/2012 | Barcheck et al. |
| D664,987 S | 8/2012 | Gleasman et al. |
| D665,401 S | 8/2012 | Rai et al. |
| D665,404 S | 8/2012 | Williams et al. |
| D665,405 S | 8/2012 | Williams et al. |
| D667,421 S | 9/2012 | Kriese et al. |
| D672,785 S | 12/2012 | Rai et al. |
| D676,861 S | 2/2013 | Ho Kushner et al. |
| D677,268 S | 3/2013 | Howes et al. |
| D678,311 S | 3/2013 | Reyna et al. |
| D679,723 S | 4/2013 | Tanghe |
| D690,319 S | 9/2013 | Wenz et al. |
| D692,019 S | 10/2013 | Baumann |
| D692,456 S | 10/2013 | Brinda et al. |
| D692,906 S | 11/2013 | Coudron |
| D693,839 S | 11/2013 | Hally |
| D695,304 S | 12/2013 | Cahill et al. |
| 8,639,812 B2 | 1/2014 | Leibow |
| D699,742 S | 2/2014 | Edwards et al. |
| D702,704 S | 4/2014 | Santos et al. |
| D704,203 S | 5/2014 | Pearson et al. |
| D705,247 S | 5/2014 | McCormack et al. |
| D705,251 S | 5/2014 | Pearson et al. |
| D708,199 S | 7/2014 | Molaro et al. |
| D708,205 S | 7/2014 | Maloney et al. |
| D709,497 S | 7/2014 | Akutsu et al. |
| D709,908 S | 7/2014 | Wujcik et al. |
| D710,876 S | 8/2014 | Cahill et al. |
| D717,325 S | 11/2014 | Hwang et al. |
| D718,777 S | 12/2014 | Hobbs et al. |
| D723,057 S | 2/2015 | Scott et al. |
| D723,583 S | 3/2015 | Cahill et al. |
| D726,211 S | 4/2015 | Konzelmann |
| 9,081,746 B1 * | 7/2015 | Helter ................. G06F 15/16 |
| D735,748 S | 8/2015 | Francisco et al. |
| D741,357 S | 10/2015 | Seo et al. |
| D741,885 S | 10/2015 | Gomez |
| D747,332 S | 1/2016 | Sic et al. |
| D752,092 S | 3/2016 | Steplyk et al. |
| D756,383 S | 5/2016 | Makida et al. |
| D757,068 S | 5/2016 | Lewis et al. |
| D758,397 S | 6/2016 | Lee |
| D760,255 S | 6/2016 | Russell et al. |
| D761,817 S | 7/2016 | Yang et al. |
| D761,834 S | 7/2016 | Debitsch et al. |
| D762,226 S | 7/2016 | Yang et al. |
| D763,892 S | 8/2016 | Kisselev et al. |
| D765,700 S | 9/2016 | Federighi et al. |
| D765,716 S | 9/2016 | Cho et al. |
| D769,289 S | 10/2016 | Cho et al. |
| D772,281 S | 11/2016 | Watson et al. |
| D773,502 S | 12/2016 | Park et al. |
| D783,668 S | 4/2017 | Clarke et al. |
| D784,393 S | 4/2017 | Federighi et al. |
| D787,546 S | 5/2017 | Otero et al. |
| D790,584 S | 6/2017 | Sakuma |
| D793,424 S | 8/2017 | Bao et al. |
| D795,914 S | 8/2017 | Mattox, Jr. et al. |
| D797,138 S | 9/2017 | Reiter et al. |
| D807,908 S | 1/2018 | Husoy et al. |
| D810,104 S | 2/2018 | Schuh et al. |
| D812,083 S | 3/2018 | Piguet et al. |
| D812,084 S | 3/2018 | Piguet et al. |
| D813,898 S | 3/2018 | St. Arnaud et al. |
| 9,996,212 B2 * | 6/2018 | Sun ................. G06F 3/0481 |
| D822,709 S | 7/2018 | Rajeswaran et al. |
| D828,847 S | 9/2018 | Burghart et al. |
| D835,149 S | 12/2018 | Balcom et al. |
| D837,255 S | 1/2019 | Lucas et al. |
| 10,185,703 B2 | 1/2019 | Abrahami |
| D842,323 S | 3/2019 | Arnaud et al. |
| D844,657 S | 4/2019 | Scott et al. |
| D845,989 S | 4/2019 | Scott et al. |
| 10,276,261 B2 | 4/2019 | Von Reden |
| D848,451 S | 5/2019 | Baber et al. |

(56) References Cited

U.S. PATENT DOCUMENTS

| | | | |
|---|---|---|---|
| D848,458 S | 5/2019 | Rocha et al. | |
| D855,069 S | 7/2019 | Shimomura | |
| D857,735 S | 8/2019 | Ferrante et al. | |
| D865,793 S | 11/2019 | Dye et al. | |
| D866,589 S | 11/2019 | Chaudhri et al. | |
| D868,102 S | 11/2019 | Meixner | |
| D890,802 S | 7/2020 | Lokhtin et al. | |
| D892,847 S | 8/2020 | Lokhtin et al. | |
| D894,949 S | 9/2020 | Shuttleworth et al. | |
| D895,665 S | 9/2020 | Felkins et al. | |
| D900,132 S | 10/2020 | English et al. | |
| D914,736 S | 3/2021 | Jung et al. | |
| 2003/0023754 A1 | 1/2003 | Eichstadt et al. | |
| 2005/0125739 A1 | 6/2005 | Thompson et al. | |
| 2006/0067654 A1 | 3/2006 | Herberger et al. | |
| 2006/0074711 A1 | 4/2006 | Mahesh et al. | |
| 2006/0224697 A1 | 10/2006 | Norris | |
| 2006/0224978 A1 | 10/2006 | Albrecht et al. | |
| 2006/0230110 A1 | 10/2006 | VanHarlingen et al. | |
| 2006/0282302 A1 | 12/2006 | Hussain | |
| 2008/0055239 A1 | 3/2008 | Garibaldi et al. | |
| 2008/0058608 A1 | 3/2008 | Garibaldi et al. | |
| 2008/0058609 A1 | 3/2008 | Garibaldi et al. | |
| 2008/0058963 A1 | 3/2008 | Garibaldi et al. | |
| 2008/0059598 A1 | 3/2008 | Garibaldi et al. | |
| 2008/0064933 A1 | 3/2008 | Garibaldi et al. | |
| 2008/0140722 A1 | 6/2008 | Jakobovits | |
| 2008/0208912 A1 | 8/2008 | Garibaldi | |
| 2009/0012821 A1 | 1/2009 | Besson et al. | |
| 2009/0106691 A1* | 4/2009 | Ballard | G06F 3/0481 715/798 |
| 2009/0113444 A1* | 4/2009 | Hackborn | G06F 11/1438 719/312 |
| 2009/0300541 A1 | 12/2009 | Nelson | |
| 2010/0097315 A1 | 4/2010 | Garibaldi et al. | |
| 2010/0131482 A1 | 5/2010 | Linthicum et al. | |
| 2010/0238089 A1* | 9/2010 | Massand | G09G 5/14 345/1.1 |
| 2011/0004839 A1* | 1/2011 | Cha | G06F 9/451 715/765 |
| 2011/0161868 A1* | 6/2011 | Green | G06F 3/0481 715/789 |
| 2011/0302528 A1* | 12/2011 | Starr | G06F 9/451 715/800 |
| 2012/0010995 A1 | 1/2012 | Skirpa et al. | |
| 2012/0096397 A1* | 4/2012 | Ording | G06F 3/0482 715/802 |
| 2012/0281970 A1 | 11/2012 | Garibaldi et al. | |
| 2012/0304112 A1* | 11/2012 | Cutler | G06F 3/0481 715/788 |
| 2013/0024812 A1* | 1/2013 | Reeves | G09G 5/14 715/810 |
| 2013/0086508 A1* | 4/2013 | Oguz | G06F 3/04883 715/779 |
| 2014/0002330 A1* | 1/2014 | Teramae | G09G 5/14 345/30 |
| 2014/0040819 A1* | 2/2014 | Duffy | G06F 9/451 715/789 |
| 2014/0047379 A1* | 2/2014 | Urawaki | G06F 3/04886 715/789 |
| 2014/0049462 A1 | 2/2014 | Weinberger et al. | |
| 2014/0143710 A1* | 5/2014 | Zhao | G16H 30/40 715/781 |
| 2014/0172458 A1* | 6/2014 | Ueda | G16H 30/00 705/3 |
| 2014/0253801 A1* | 9/2014 | Richman | H04N 21/4312 348/564 |
| 2014/0303988 A1* | 10/2014 | Maneri | G16H 20/10 705/2 |
| 2014/0324469 A1* | 10/2014 | Reiner | G16H 10/60 705/3 |
| 2014/0331174 A1* | 11/2014 | Wen | G06F 3/04883 715/804 |
| 2014/0337794 A1* | 11/2014 | Vranjes | G06F 3/0481 715/800 |
| 2014/0380201 A1* | 12/2014 | Massand | G06F 3/0487 715/761 |
| 2015/0113422 A1* | 4/2015 | Pfeiffer | G16H 10/60 715/739 |
| 2015/0178447 A1* | 6/2015 | Cohen | G16H 30/20 705/2 |
| 2016/0034155 A1* | 2/2016 | Vranjes | G06F 3/04842 715/803 |
| 2016/0048398 A1* | 2/2016 | Taylor | G06F 9/4843 717/168 |
| 2016/0080549 A1* | 3/2016 | Yuan | H04N 21/440263 455/420 |
| 2016/0142394 A1* | 5/2016 | Ullrich | H04W 4/33 726/7 |
| 2016/0147938 A1* | 5/2016 | McConnell | G16H 10/60 715/763 |
| 2016/0147971 A1 | 5/2016 | Kolowitz et al. | |
| 2016/0202852 A1 | 7/2016 | Park et al. | |
| 2016/0364122 A1 | 12/2016 | Shimomura et al. | |
| 2016/0378272 A1 | 12/2016 | Whitlark et al. | |
| 2017/0132371 A1* | 5/2017 | Amarasingham | G06F 40/30 |
| 2017/0308650 A1* | 10/2017 | Brill | G16H 40/63 |
| 2018/0046602 A1 | 2/2018 | Sisson et al. | |
| 2018/0107632 A1* | 4/2018 | Blinn | G06F 16/9577 |
| 2018/0137938 A1* | 5/2018 | Vaddiraju | A61B 5/0004 |
| 2018/0217849 A1* | 8/2018 | Gullen | G06F 3/04842 |
| 2019/0034591 A1* | 1/2019 | Mossin | G16H 50/30 |
| 2019/0066831 A1* | 2/2019 | Mairs | G06T 11/206 |
| 2019/0103172 A1* | 4/2019 | Li | G16H 70/40 |
| 2019/0108201 A1 | 4/2019 | Abrahami et al. | |
| 2019/0189282 A1* | 6/2019 | Noro | G16H 40/63 |
| 2019/0391825 A1* | 12/2019 | Jann | G06F 3/0482 |
| 2020/0051677 A1 | 2/2020 | Harrison | |
| 2020/0117703 A1* | 4/2020 | Hinchliffe | H04L 67/306 |
| 2020/0159372 A1* | 5/2020 | Bates | G06F 3/0486 |
| 2020/0257920 A1* | 8/2020 | Kumar | G06T 1/0014 |
| 2020/0323504 A1* | 10/2020 | Okabe | G06F 3/1423 |

FOREIGN PATENT DOCUMENTS

| | | |
|---|---|---|
| CN | 305887463 | 6/2020 |
| CN | 306141178 | 10/2020 |
| EP | 0651330 B1 | 5/1995 |
| WO | 2018125280 A1 | 7/2018 |
| WO | 2018201182 A1 | 11/2018 |

OTHER PUBLICATIONS

GoldenLayout-a multi-window javascript layout manager for webapps; downloaded Nov. 5, 2019 from https://golden-layout.com/; 2 pages.

Soderlund, Tom, Micro frontends—a microservice approach to front-end web development; downloaded Nov. 5, 2019 from https://medium.com/@tomsoderlund/micro-frontends-a-microservice-approach-to-front-en; 5 pages.

Turn on Xmouse active window tracking (focus follows mouse pointer) feature in Windows 8.1, Windows 8 and Windows 7, Google Chrome; downloaded Nov. 21, 2019 from https://winaero.com/blog/turn-on-xmouse-active-window-tracking-focus-follows-mouse-; 6 pages.

CSS-Only Carousel, brand n/a, css-tricks.com <http://css-tricks.com>, published by Chris Coyier on Jan. 10, 2020 © not listed, online, site visited Apr. 24, 2021. Available at URL: <https://css-tricks.com/css-only-carousel/> (Year: 2020).

MetaSlider, WordPress, troldtekt.com <http://troldtekt.com>, author unlisted, published on May 20, 2013 © not listed, online, site visited Apr. 24, 2021. Available at URL: <https://wordpress.org/plugins/ml-slider/> (Year: 2013).

* cited by examiner

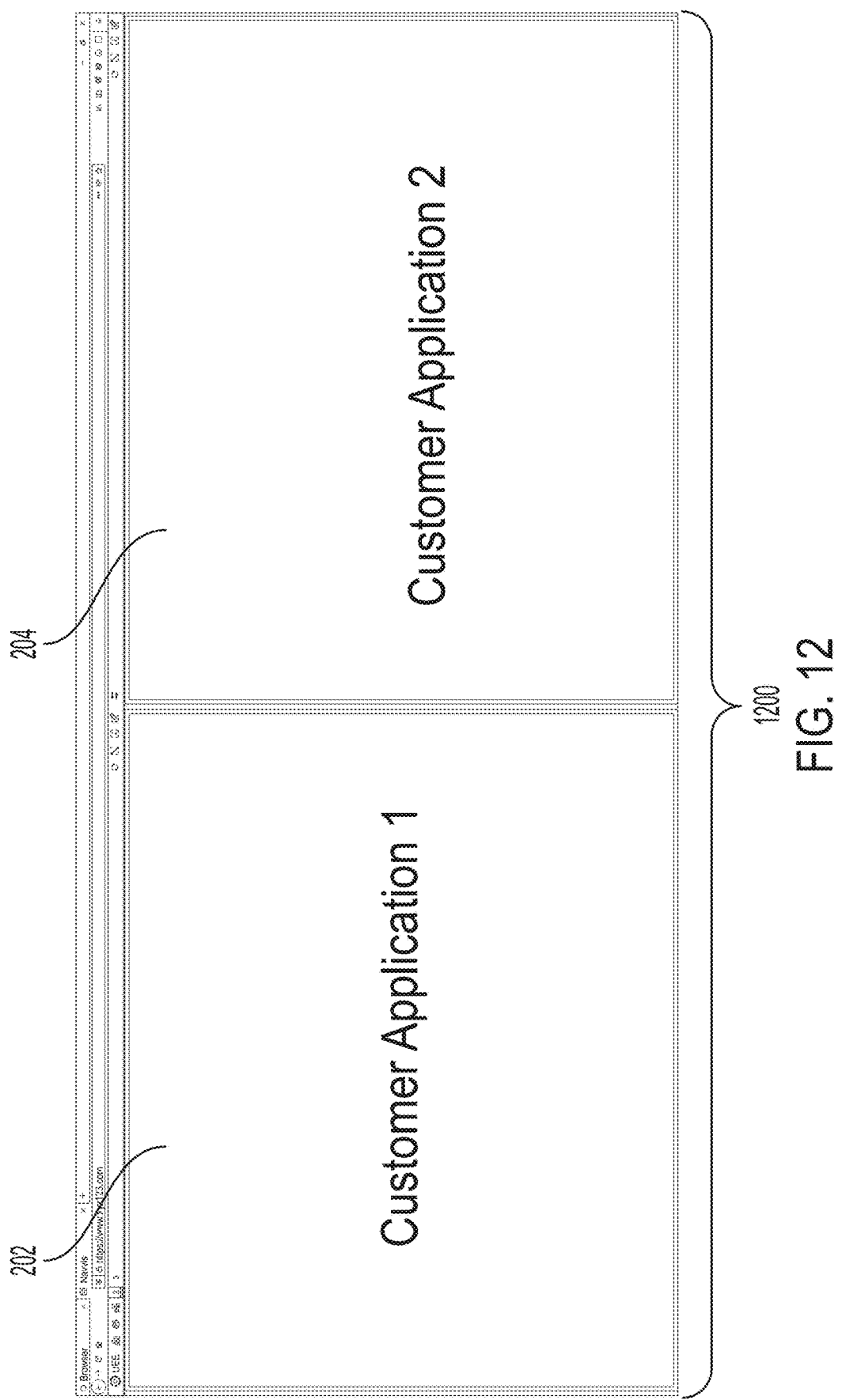

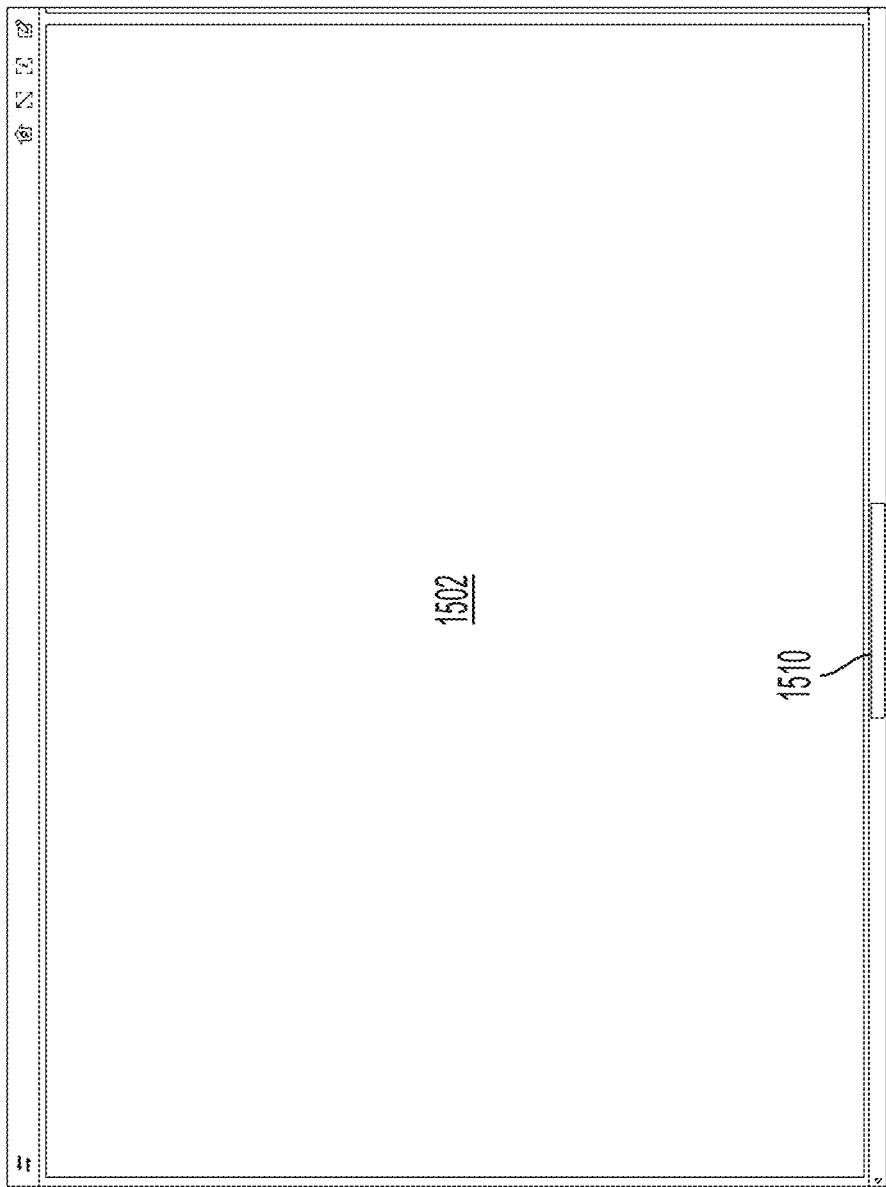

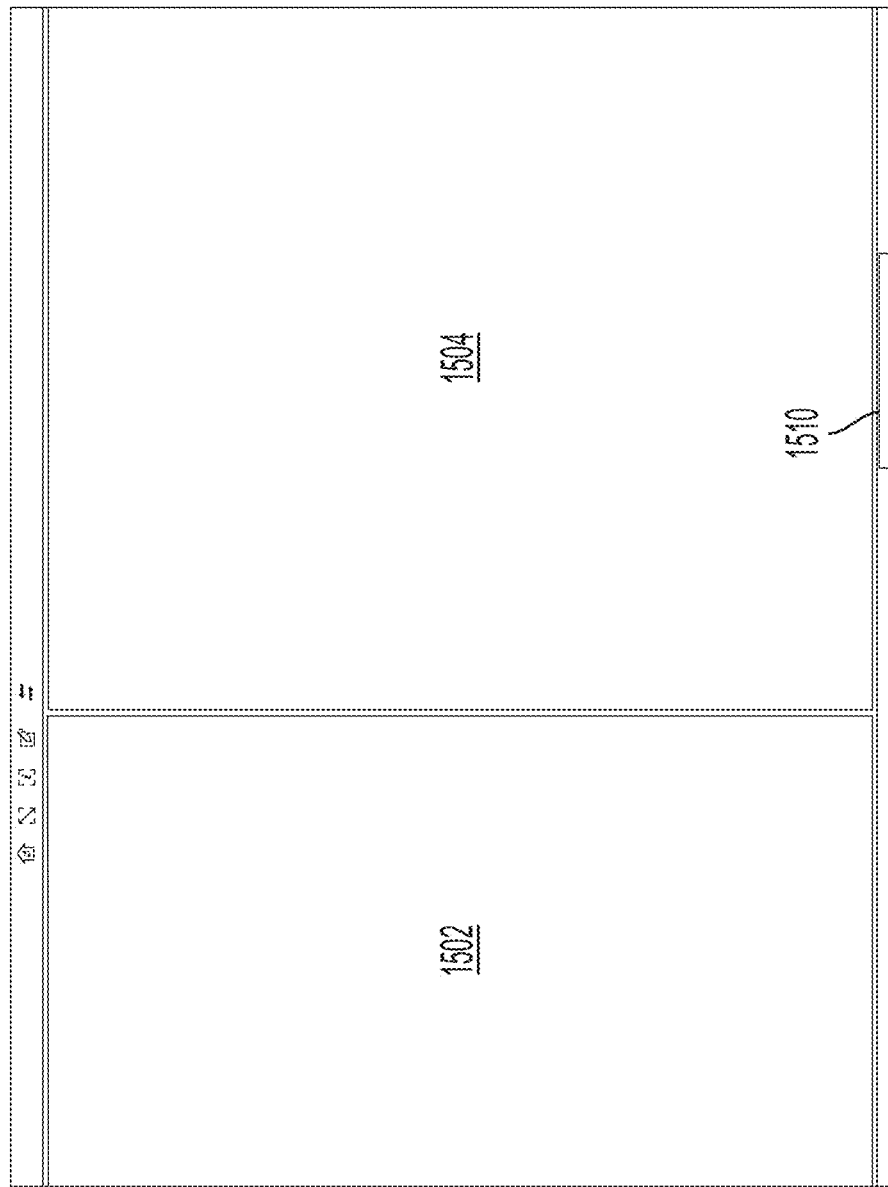

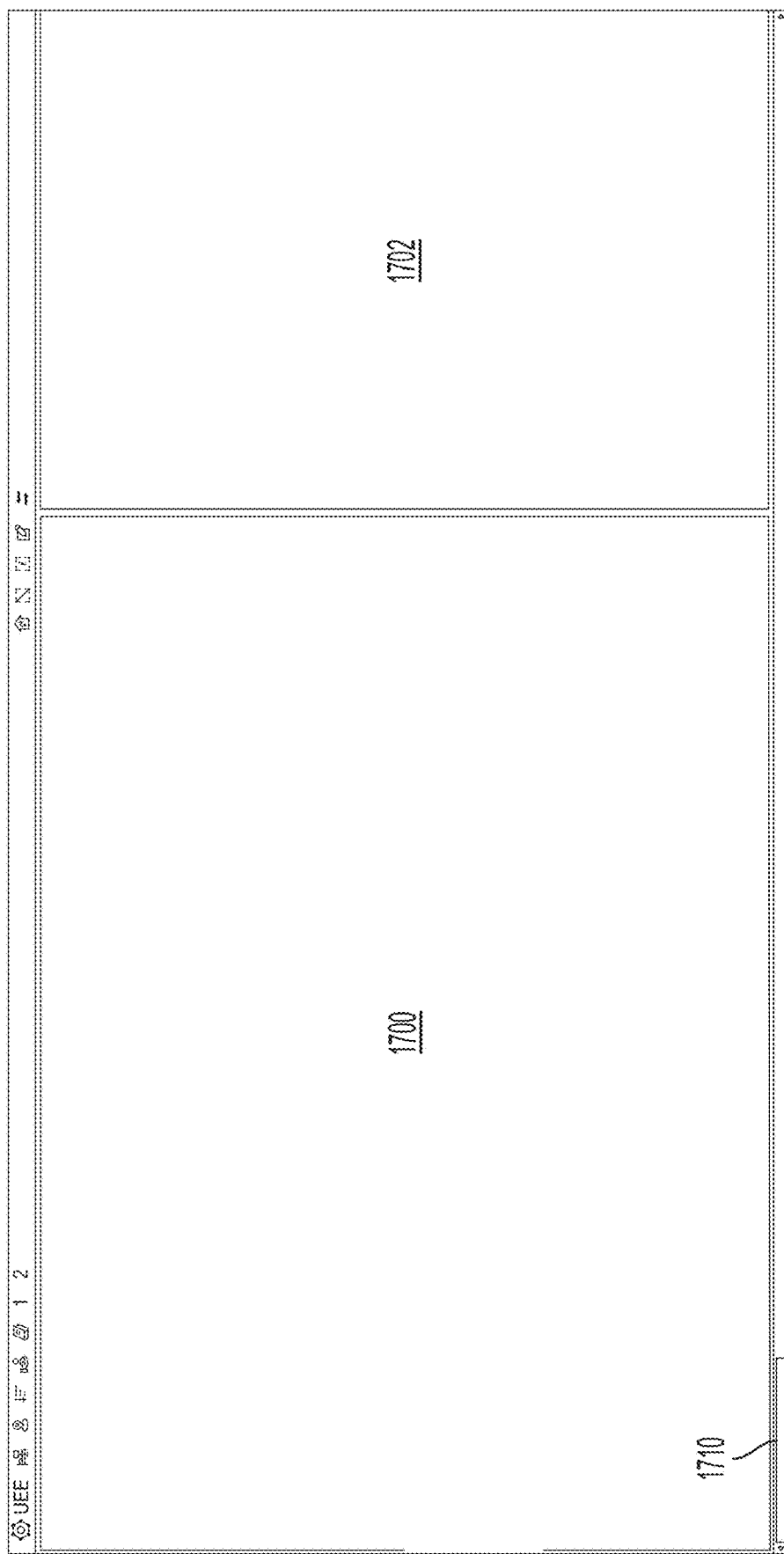

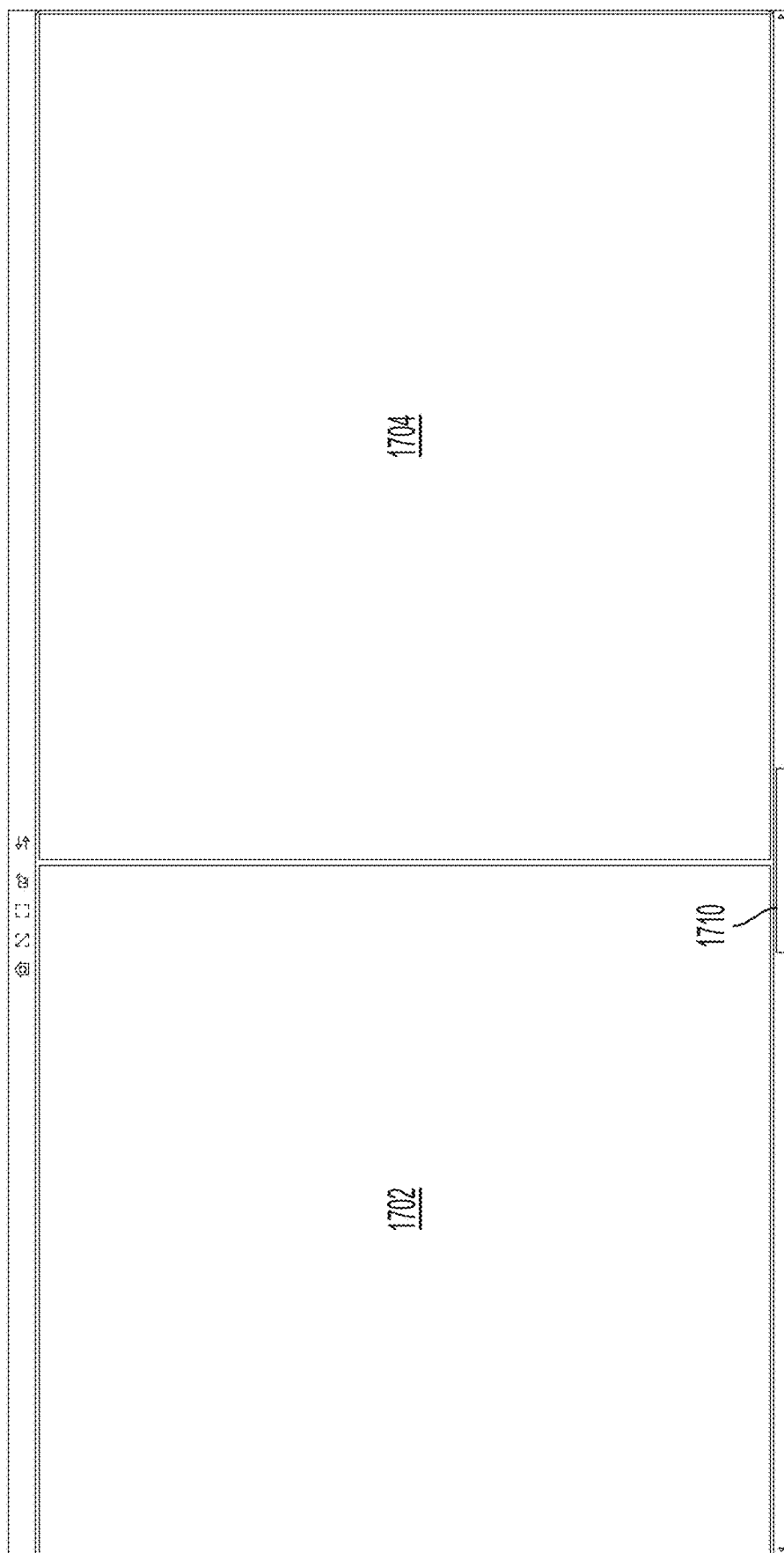

UNIFIED ECOSYSTEM EXPERIENCE FOR MANAGING MULTIPLE HEALTHCARE APPLICATIONS FROM A COMMON INTERFACE

CROSS-REFERENCE AND PRIORITY CLAIM TO RELATED PATENT APPLICATIONS

This patent application claims priority to U.S. provisional patent application Ser. No. 62/961,530, filed Jan. 15, 2020, and entitled "Unified Ecosystem Experience for Managing Multiple Healthcare Applications from a Common Interface", the entire disclosure of which is incorporated herein by reference.

This patent application is also related to (1) U.S. patent application Ser. No. 17/126,669, filed this same day, and entitled "Unified Ecosystem Experience for Managing Multiple Healthcare Applications from a Common Interface with Trigger-Based Layout Control" and (2) U.S. patent application Ser. No. 17/126,695, filed this same day, and entitled "Unified Ecosystem Experience for Managing Multiple Healthcare Applications from a Common Interface with Context Passing Between Applications", each of which claims priority to U.S. provisional patent application Ser. No. 62/961,530, filed Jan. 15, 2020, and entitled "Unified Ecosystem Experience for Managing Multiple Healthcare Applications from a Common Interface", and the entire disclosures of each of which are incorporated herein by reference.

INTRODUCTION

To effectively manage the health of populations, clinical and non-clinical professionals throughout the continuum of care must rely on computer applications for monitoring and engaging in patient care. However, such users of conventional healthcare computer platforms are inundated by a wide array of disparate applications, each having individualized user interfaces without coherency. The current user experience of such applications does not leverage an integrated experience due to the conventional approaches requiring users to awkwardly manage and navigate within each application via separate computers, displays, browsers and/or windows. At the same time, while these disparate applications may at times be integrated with common source data (e.g. electronic health record (EHR) data), care teams lack the ability to efficiently and effectively engage in multiple applications simultaneously alongside one another.

The complexities of managing the health of populations requires that healthcare professionals access the right information at the right time to empower their workflows leading to optimized cost and quality in healthcare. Such workflows commonly comprise a series of tasks to monitor and engage patients. Efficiency and effectiveness can be impacted by how certain tasks are accomplished, in what order they are accomplished, and by whom they are accomplished. In the case of a new Emergency Department (ED) visit by a patient, a healthcare user may need to engage in a workflow of receiving the ED visit alert, reviewing the specific acute care facility, engaging in a list of tasks assigned upon the visit, updating the patient record with details associated with the visit and engaging with the patient for care navigation. However, healthcare professionals are constrained by the limitations of currently relying on a plurality of healthcare applications that are required to view and complete the aforementioned workflow steps for this ED event.

For example, significant portions of the display real-estate in the conventional applications are consumed by elements (e.g. URLs, browser tabs, etc.) which have no clinical benefit to the workflow. Display real-estate is also lacking an ability to instantly adjust the layout of the applications that are simultaneously displayed and limited to the size of the desktop. In addition to this wasteful and suboptimal use of display real-estate, these conventional applications lack effective contextual connections to one another, and they also lack effective interoperability of data in some cases. Moreover, conventional applications are often constrained to a particular display type and are not amenable to being uniformly displayed across a plethora of different display types which are common place in modern healthcare. There is a need for healthcare users to be able to transition through different display formats during the day depending on the different locations from which they may work throughout the day from large form-factor single and multi-panel wall displays to desktop computer monitors and mobile device displays (e.g. tablets). In practice, the efficiency and effectiveness of clinical workflows are impacted by constantly switching a display between a single application at a time and the effort involved in accessing, sizing and positioning of extraneous elements such as application borders, browser tabs and URL lines. To add further complexity, healthcare users may have a need to monitor and engage in managing the health of multiple populations across multiple customers based upon centralized team configurations which can be a significant technical and engineering challenge.

Various technical approaches have been introduced to attempt to improve the management of multiple healthcare applications over the years including hardware-based solutions such as the use of video display and/or universal mouse processors (e.g. via hardware which employs conversion and switching techniques) to display and interact with multiple applications, in addition to the emergence of software solutions such as web frameworks and micro frontends. However, each of these solutions suffers from various drawbacks and limitations. For example, hardware-based techniques utilizing video display and/or a universal mouse processors rely on connecting systems at the video and mouse hardware signal level for sizing, positioning and controlling multiple applications. Further, these hardware solutions are often restricted to applications which are derived from locally-present systems connected via hardware cables. Web frameworks have evolved over the years to help enable multiple web applications to be displayed in a layout merely serving as a building block for a consolidated multi-panel layout. And, micro frontends have emerged more recently to help enable the appearance of a single web page which is fed by multiple web tiles. This allows for support of separate user interaction in the limited tiles presented within the single web page. However, current web frameworks and micro frontends do not consider or provide solutions for the overall technical challenges arising from the above-noted user-experience issues and major challenges of healthcare professionals. Thus, despite these current options, a significant need remains in the art for a technical solution providing for a unified ecosystem experience based upon improved embodiments for empowering healthcare users with seamless management and control over a plurality of different applications in a maximized, consolidated and synchronized user interface.

The present application discloses a browser-based, user interface manager application which manages and displays a plurality of healthcare applications presented in such a manner that the layout and overall look-and-feel of the applications within the browser provides a unified ecosystem experience (UEE) for a user.

Previously, the presentation of modern healthcare applications was limited by independent browsers or browser tabs being separately displayed and controlled often one at a time alongside user interface elements with no benefit to the clinical workflow. Engaging in these disparate applications requires constant manual context switching by the user, which negatively impacts efficiency and monitoring since healthcare users may miss relevant information leading to clinical errors due to applications being hidden by the current displayed application.

The UEE disclosed herein leverages the latest technology such as HTML Inline Frame (iframe) elements which enable nested browsing context embedding with a plurality of HTML based applications presented within one consolidated view for healthcare users. Each embedded browsing context has its own session history supporting particularized contexts within each application. A browsing context that embeds the others is called a parent browsing context. A topmost browsing context (e.g., one with no parent) is usually the overall browser window itself which is utilized to launch the overall UEE. The iframes generally can be referred to as frame data structures, and they can be utilized to provide a variety of browser functions, including but not limited to activating a full-screen mode (e.g., by calling a request full-screen command). Additionally, an API can be called from an application within the user interface manager application posting a message to be delivered to any application that it was generated for such as to an embedded iframe or the containing webpage. Iframe elements can have a displayed or hidden state to seamlessly present the optimal combination of applications at each point in the healthcare workflow. While hidden elements will not be shown visibly to the user, they continue to persist within a Document Object Model (DOM) and do not require a reload upon being shown since only the visibility of the element switched. This controlled switching by the UEE between a visible status and a hidden status for concurrently persisting frame data structures improves the functioning of the computer system by providing a mechanism for the display to quickly switch to different panel layouts (e.g., changing which applications are shown in which panels).

The overall browser of the user interface manager application handles the DOM. The DOM is a programming API for HTML and/or XML documents defining the logical structure of documents and the way a document is accessed or manipulated. The term document may comprise, for example, XML being used as a way of representing many different kinds of information that may be stored in diverse systems, and as such may be more properly referred to as data rather than a document. The XML presents this data as documents, and the DOM may be used to manage this data. The DOM allows for programming to create and build documents, navigate their structure, and add/delete/modify elements or content. In general, anything within the XML (or HTML) document can be accessed, changed, deleted, or added using the DOM.

The user interface manager application of the present application is capable of managing a display layout of the plurality of applications across a highly diverse set of display formats from mobile to desktop to wall screens while performing view synchronization. Therefore, this solution provides a seamless, unified graphical user interface (GUI) that displays the applications as a plurality of panels within a common view. Accordingly, the user interface manager application can also be referred to as an application layout and synchronization manager representing a substantial improvement over conventional techniques for the management of multiple healthcare applications.

BRIEF DESCRIPTION OF THE DRAWINGS

The accompanying drawings, which are incorporated in and form a part of the specification, illustrate the embodiments of the present user interface manager application disclosed herein and together with the description serve to explain the principles of the user interface manager application. In the drawings:

FIG. 12 illustrates a multi-customer view of the user interface manager application.

FIGS. 15A-15E show examples of scrollability for an example 3-panel view with respect to the first screen dimension.

FIGS. 17A-17C show examples of scrollability for an example 3-panel view with respect to the second screen dimension.

FIGS. 21A-21D show example application views corresponding to the different population levels—namely, the patient level, panel level, contract level, and system level, respectively.

It should be understood that all of the patient information described herein and shown by the drawings is fictitious patient information for fictitious patients.

DETAILED DESCRIPTION OF EXAMPLE EMBODIMENTS

Figure 1:
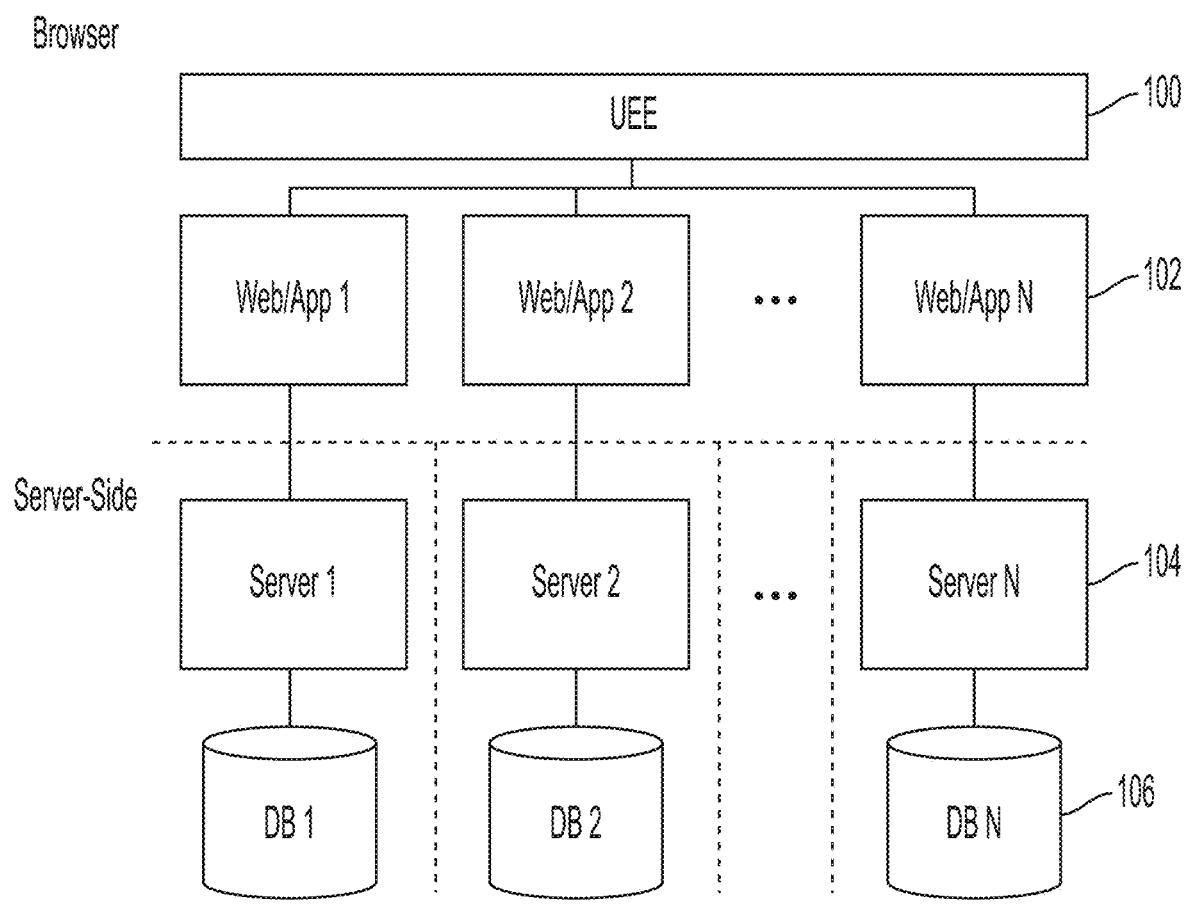
FIG. 1 depicts an exemplary process flow of the interoperation of system components of a system including the user interface manager application.

Referring to the accompanying drawings in which like reference numbers indicate like elements, FIG. 1 illustrates an embodiment of the present user interface manager application (also known as the UEE) 100. The user interface manager application 100 is configured in a browser, and capable of displaying a plurality of applications or websites 102 (e.g., Web/App 1, Web/App 2 . . . Web/App N) in a unified user interface. In order to populate the browser with the necessary information for the various applications on the server-side, there are respective servers 104 (e.g., Server 1, Server 2 . . . Server N) that correspond to the respective applications and/or websites (e.g., Web/App 1, Web/App 2 . . . Web/App N). Each server (e.g., Server 1, Server 2 . . . Server N) communicates with a respective databases 106 (e.g., DB 1, DB2 . . . DB N). These databases store certain information for populating aspects of the applications, including but not limited to image files, text files, among other types.

FIGS. 2A to 2D illustrate exemplary embodiments of the user interface manager application 100.

Figure 2A:
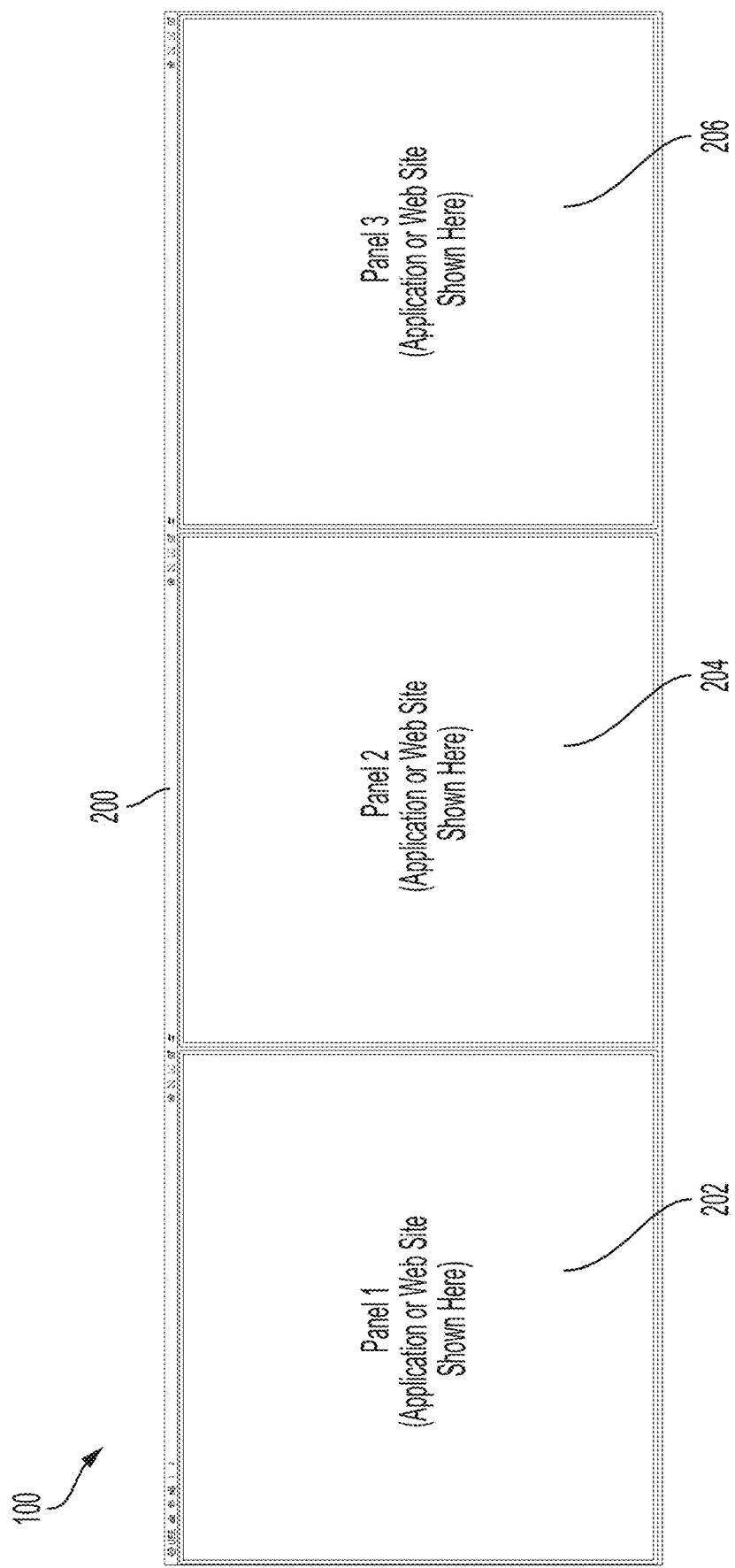
FIG. 2A illustrates a three panel embodiment of the user interface manager application.

FIG. 2A illustrates a main toolbar 200 and a three-panel arrangement of the user interface manager application 100. The first/left panel 202 of the three panels may for example display an application (not shown) containing information of a plurality of patients. The second/middle panel 204 may display an application (not shown) matching patient needs with providers who offer services including medical care, food, job training, etc. in a particular zip code. The third/right panel 206 may display a healthcare application (not shown including a dashboard of tasks, appointments and work queues.

Figure 2B:
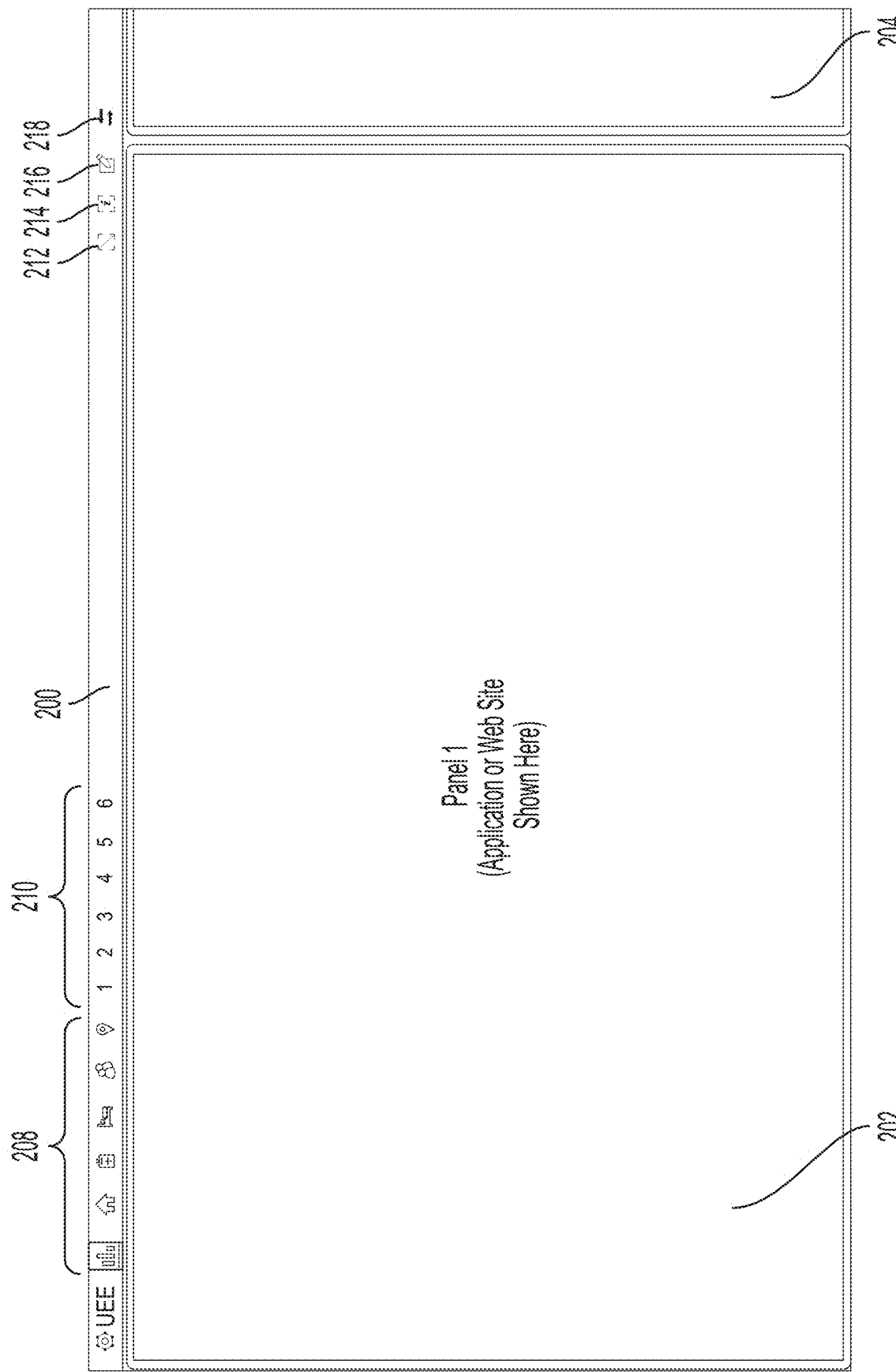
FIG. 2B illustrates a detail view of a toolbar of the user interface manager application in accordance with FIG. 2A.

FIG. 2B illustrates a zoomed-in view of the common main toolbar 200 that can span across the plurality of panels (e.g., 202, 204, 206) in the overall user interface 100. This toolbar 200 may include operative (e.g., clickable) icons/buttons directed to single-panel presets 208 and multi-panel presets 210 (discussed in greater detail below with reference to FIG. 10C) as well as buttons/icons for full screen expansion 212, help information 214, display settings 216 for editing screen layouts, and swapping 218 of (e.g., adjacent) application panels. These icons/buttons can grouped for user convenience. For example, the upper left icons in FIG. 2B may comprise global icons/buttons that apply changes to the overall window of the user interface manager application 100 from a global perspective, whereas the icons/buttons in the upper right of each panel may only apply local changes to that respective panel (e.g., 202).

Figure 2C:
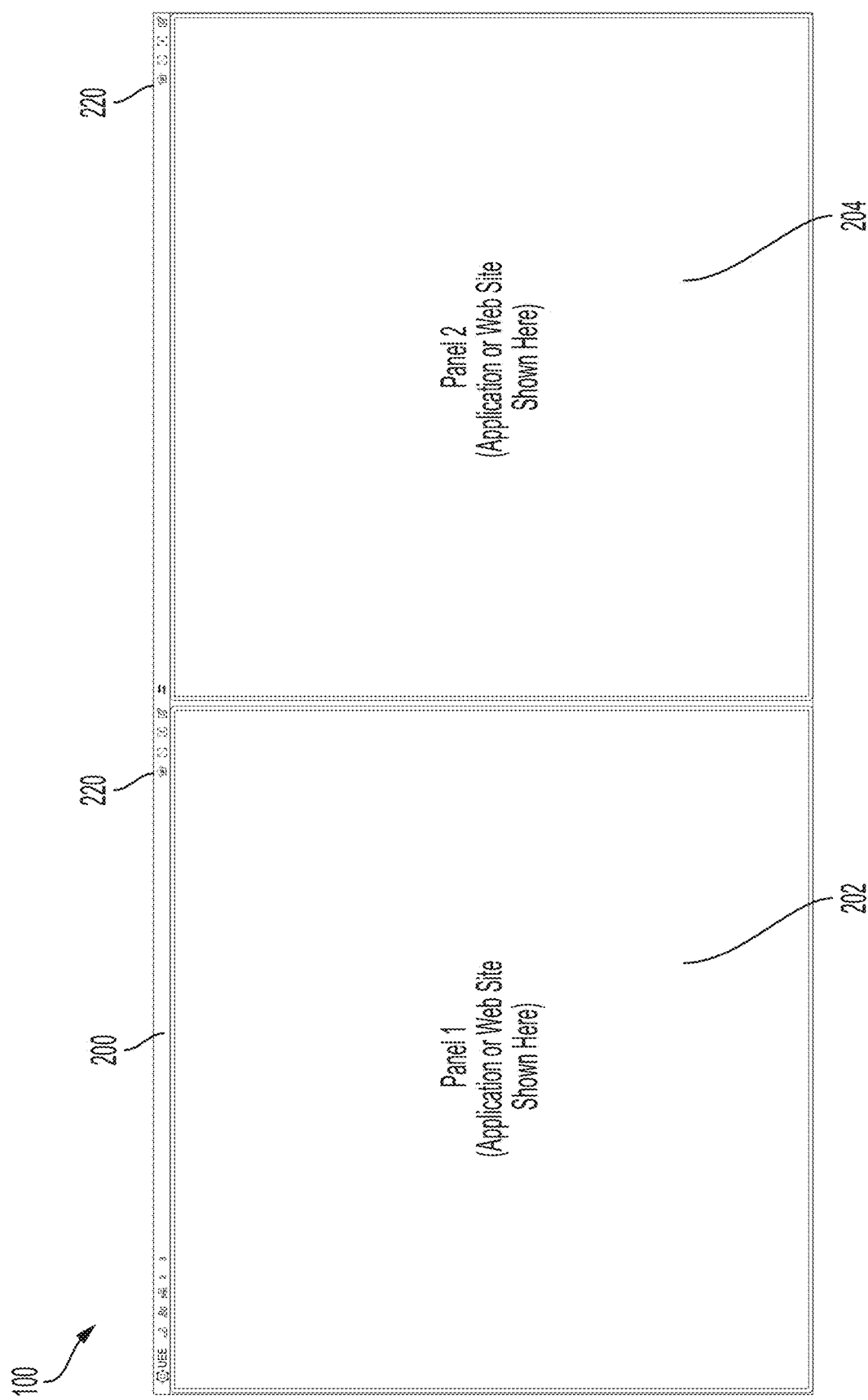
FIG. 2C illustrates a two panel embodiment of the user interface manager application.

FIG. 2C shows a two-panel arrangement similar to the three-panel arrangement described above, less a third panel. As shown in FIG. 2C, one specific example of the local icons as described above with respect to FIG. 2A is the refresh icons 220 shown in the upper right of each panel section of the main toolbar 200 of FIG. 2A. These refresh icons only serve to refresh the associated panel (e.g., 202, 204). Thus, in the three-panel embodiment of FIG. 2A, there are three refresh icons, one for each panel 202, 204, 206 (e.g., the refresh icon is provided on a per panel basis). The two applications in the two-panel layout of FIG. 2C may be sized to share the display area of the two-panel layout.

Figure 2D:
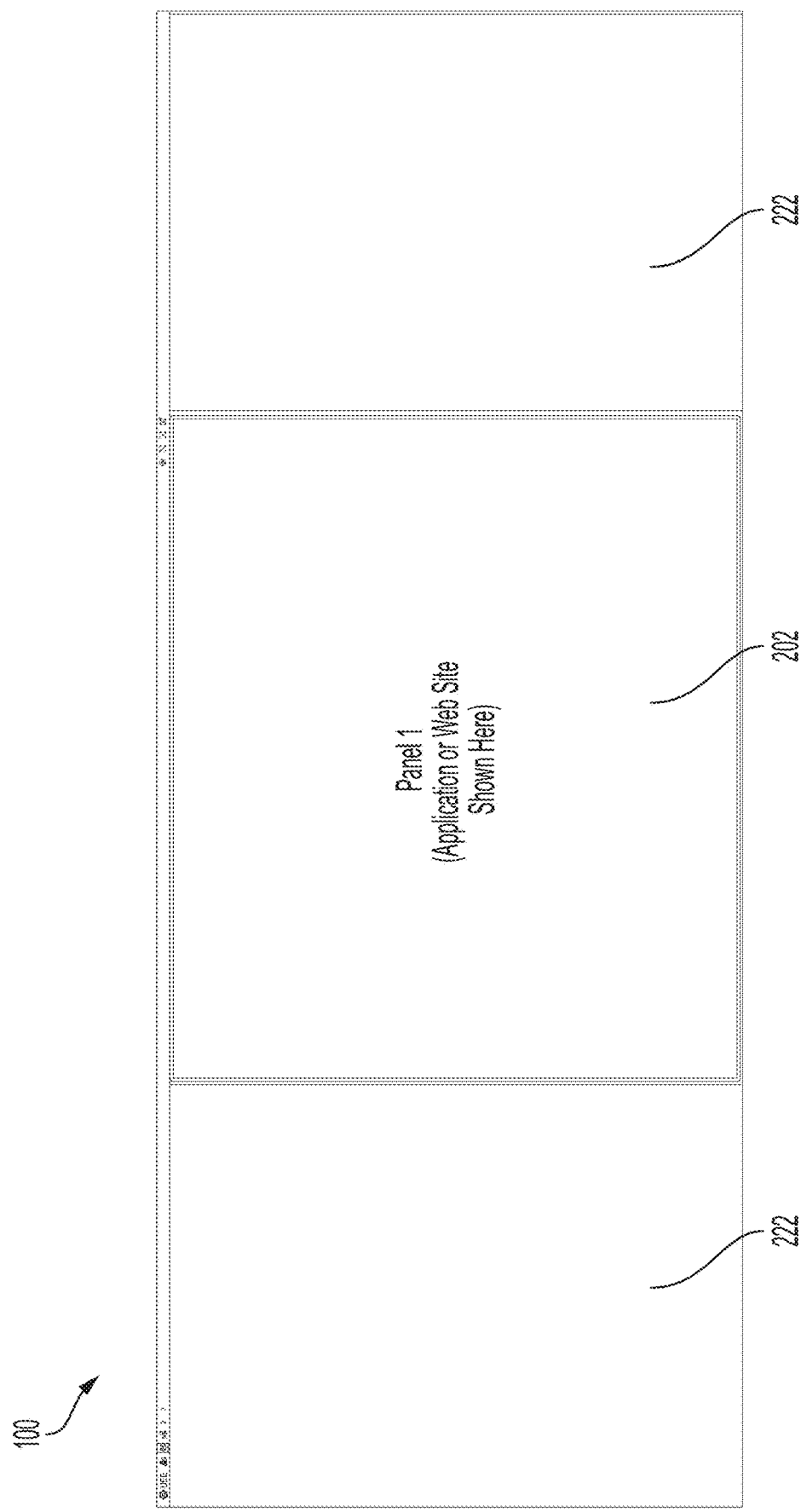
FIG. 2D illustrates a single panel embodiment of the user interface manager application.

FIG. 2D shows a single panel (e.g., 202) arrangement similar to the above three- and two-panel arrangements in FIGS. 2A and 2C, except that the unoccupied display areas have a generic background 222 instead of being populated with an application.

The applications that populate the panels 202/204/206 may take the form of one or more healthcare computer applications. Examples of suitable healthcare applications for use in populating the panels of the user interface manager application 100 include applications such as the COREO™ suite of applications available from Navvis & Company, LLC of St. Louis, Mo.

Furthermore, as described above, panels 202/204/206 need not necessarily be populated by computer applications—a practitioner may choose to populate one or more of the panels with websites (or with a combination of applications and websites if desired). Thus, rather than the user interface manager application 100 displaying a series of applications, websites may be displayed in the panels of the user interface manager application 100. The displayed website can be a web page accessed at a web uniform resource locator (URL). Accordingly, each panel can be associated with a web uniform resource locator (URL) or the like so that panel will display a website corresponding to the associated web URL. Such websites may include health services websites, among other examples. Thus, the user interface manager application 100 is able to display panels in a composite manner whereby the panels comprise a mix of applications and websites, as desired by the user. The above examples described in FIGS. 2A to 2D are not intended to be limiting with respect to the number of panels and arrangement/amount of icons on the toolbar. For example, the user interface manager application can be configured to display more than three panels, different sized panels, vertically/horizontally positioned panels, and the toolbar icons may be configured in various layouts comprising various icons.

Figure 3A:
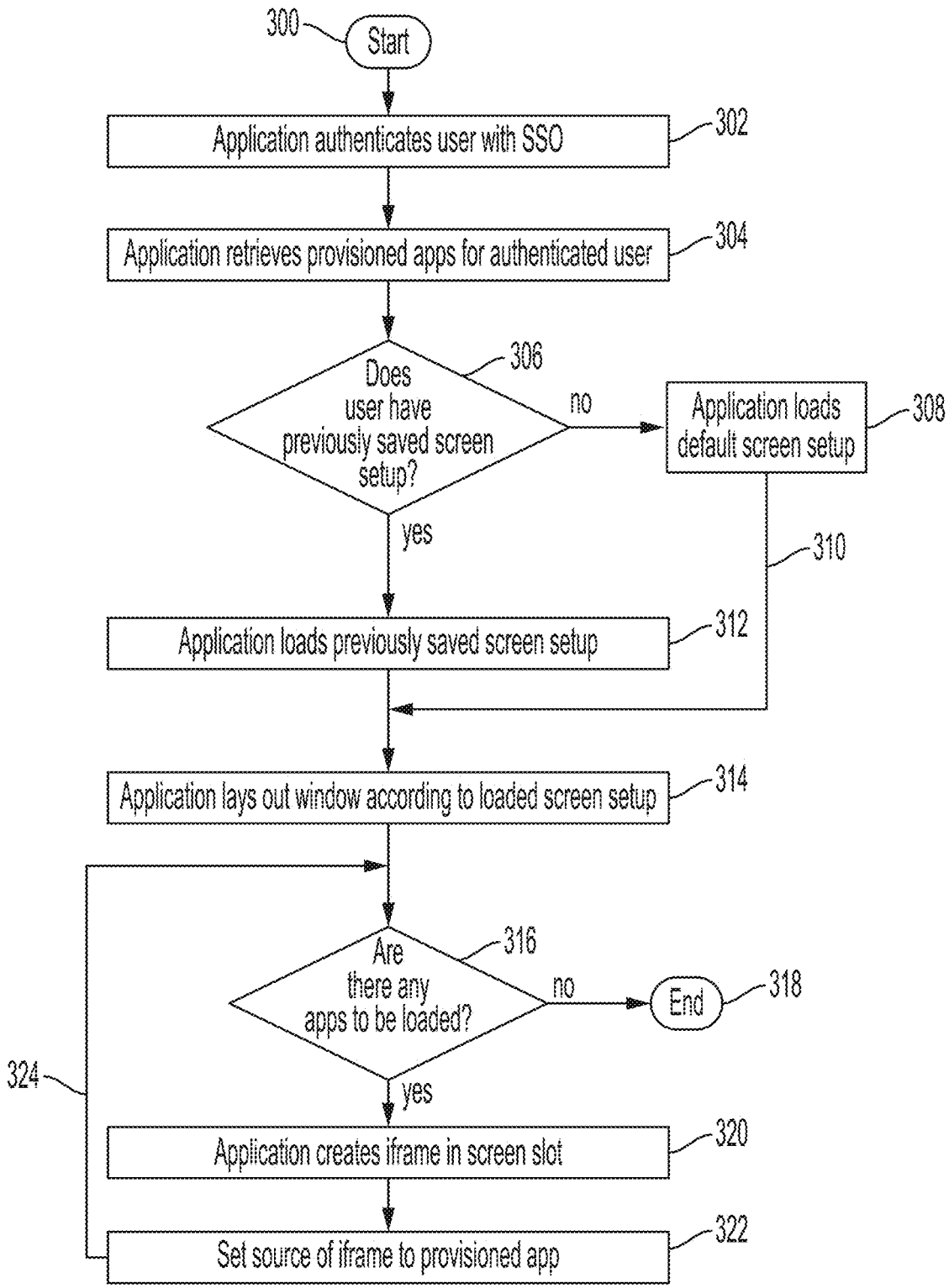
FIG. 3A depicts an exemplary process flow for the creation and population of a main composite screen of the user interface manger application according to FIGS. 2A, 2C and 2D.

FIG. 3A depicts a process flow for creating and populating a main composite screen of the user interface manager application 100 with content from different source applications. At step 300, the creation/population process starts. At step 302, an application authenticates a user (e.g., with a single-sign on (SSO) password management platform such as the OKTA® SSO password management platform available from Okta, Inc. that can also manage application permissions for the UEE). With SSO, users can enter one login to access a plurality of applications for which they have been permitted access (e.g., provisioned applications). At step 304, the user interface manager application retrieves provisioned applications for the authenticated user. Next, at step 306, a determination is made as to whether or not the user has a saved screen setup (e.g., a preset). If the determination at step 306 is "no," the user interface manager application loads a default screen setup at step 308, and the process flow continues via step 310. If the determination at step 306 is "yes," the user interface manager application loads a previously saved screen setup at step 312. With either the default or saved screen setup selected, at step 314, the user interface manager application presents the windows according to the loaded screen setup. Next, at step 316, a determination is made as to whether or not any applications are to be loaded. If the determination at step 316 is "no," the process flow ends at step 318. If the determination at step 316 is "yes," then at step 320 the application creates an iframe in a designated screen slot according to the user's preset. Finally, at step 322, the source of the iframe is set to a provisioned application. This setting of the source of the iframe at step 322 can be repeated as necessary by the process flow jumping back to just before step 316, as shown by step 324.

Figure 3B:
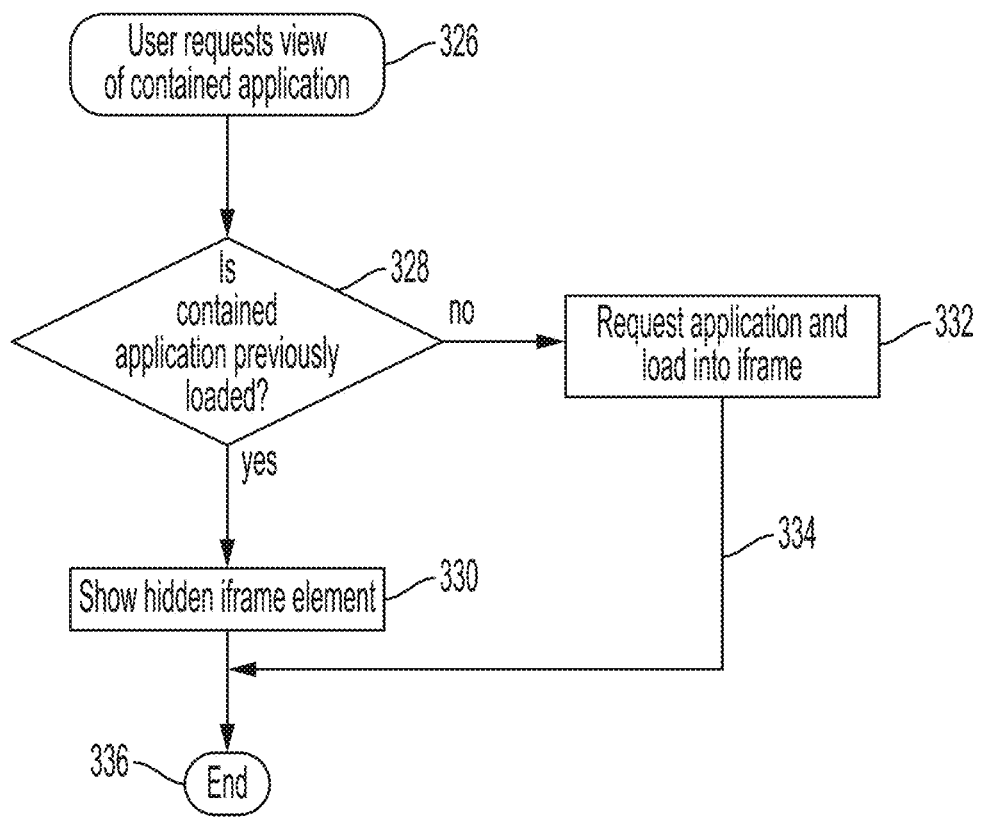
FIG. 3B depicts an exemplary process flow for iframe management of the user interface manager application according to FIGS. 2A, 2C and 2D.

FIG. 3B illustrates a process flow for iframe management as performed by the user interface manager application. At step 326, a user requests to view an application contained within the user interface manager application. Such a contained application may, for example, be a healthcare application as described above. At step 328, a determination is made as to whether the contained application was previously loaded. If the determination at step 328 is "yes," then the process flow proceeds to step 330 at which time a hidden iframe element is then shown, and then the routine ends at step 336. If the determination at step 328 is "no," then the process flow proceeds to step 332 whereby an application is requested and loaded into a corresponding iframe, and the process flow proceeds via step 334 to an end at step 336. In operation, each application will have its iframe state maintained regardless of whether it is currently being shown. This serves to prevent a noticeable refresh (and any corresponding hit on performance) upon bringing the iframe and its associated application back into view. In order to prevent unnecessary memory utilization with respect to iframe management, the applications and their associated iframes will be lazily loaded such that applications can allow for user display and interaction to begin prior to the entire application being downloaded at the time when they are first requested. As the user engages in the user interface manager application, iframes are added to memory. Because each browsing context is a complete document environment, every iframe in a page requires increased memory and other computing resources. There is an iframe pool comprising loaded iframes and not-yet-loaded iframes. The iframes are added to memory as the user progresses through the user interface manager application using the various applications. While any number of iframes can be used, the use of more and more iframes could result in performance problems and noticeable lag when switching between applications. However, due to the manner in which the user interface manager application manages the loading of iframes to prevent unnecessary memory utilization, the user does not experience any significant lag when switching or loading applications. Rather, from the user's perspective switching and/or loading applications is a quick, streamlined event. The above-described manner in which the user interface manager application manages iframes to optimize the display of applications but still realizing reduced memory utilization is not well-understood or conventional representing a significant improvement over current techniques, and serves to enhance the user experience during engagement of the user interface manager application.

By way of the above-described iframe management techniques, various states and instances of the applications can be preserved via the iframes such that even if a user should swap locations of the applications within the panels of the browser of the user interface manager application, the applications retain their state (e.g., the applications maintain the information they were displaying prior to being swapped by the user). This represents further improvements over the art and adds further convenience in addition to utility for the user. This non-conventional, not well-understood management technique realizes the goal of merging a variety of applications/websites into a common interface to create a look-and-feel of one application as opposed to many separate applications.

Figure 4:
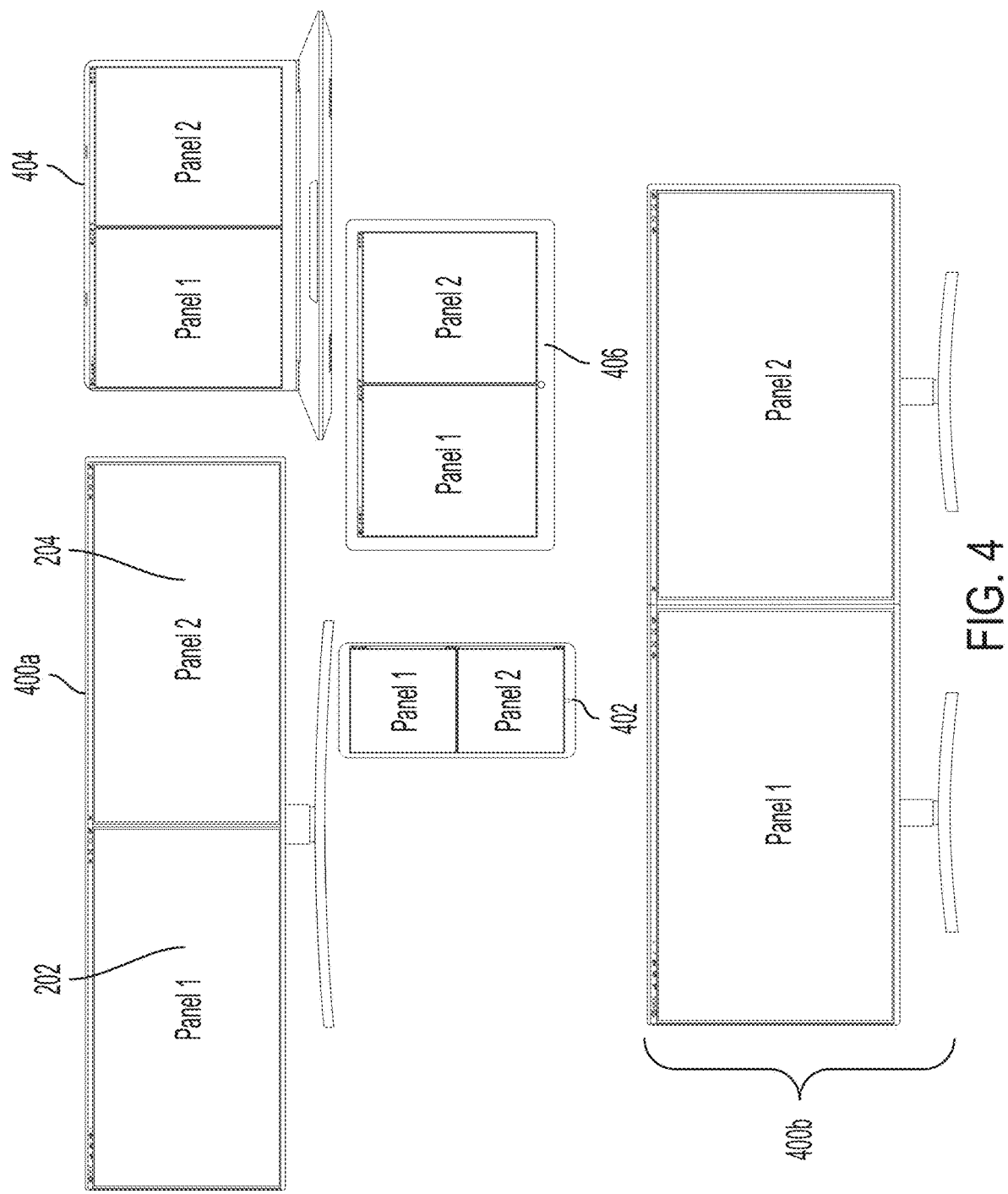
FIG. 4 illustrates the user interface manager application on various display screens.

FIG. 4 illustrates an auto-adaptation feature of the user interface manager application across a wide array of display formats. As shown in FIG. 4, the user interface manager application maintains integrity and appearance across a variety of displays. The user interface manager application 100 can display the panels (e.g., 202, 204) such that they can be viewed on a desktop monitor. Such a monitor can be a single monitor 400a having dimensions to enable widescreen aspect ratio viewing or may comprise a plurality of monitors 400b adjacent to one another and configured for use as a single desktop display (e.g., two or more monitors can display a single desktop user interface). In addition, the user interface manager application 100 can scale down to small form-factor displays such as the screens of mobile devices 402, laptops 404 and tablets 406 as well as scale up to wider screens such as those found on wide screen monitors and ultra-wide screen monitors, while preserving the overall look-and-feel of the user interface manager application allowing users to experience the solution in a similar manner to the above-described traditional desktop computer displays. The user interface manager application 100 can also be used on a wall monitor (not shown) such as a plurality of television/monitors mounted on a wall in for a common viewing location for healthcare users. (e.g. a centralized command center) Thus, the user interface manager application can scale to fit standard and/or widescreen aspect ratio large form-factor wall displays, while maintaining a consistent viewing experience and user experience. Accordingly, the user interface manager application maintains integrity and appearance across a gamut of display screens.

Figure 5:
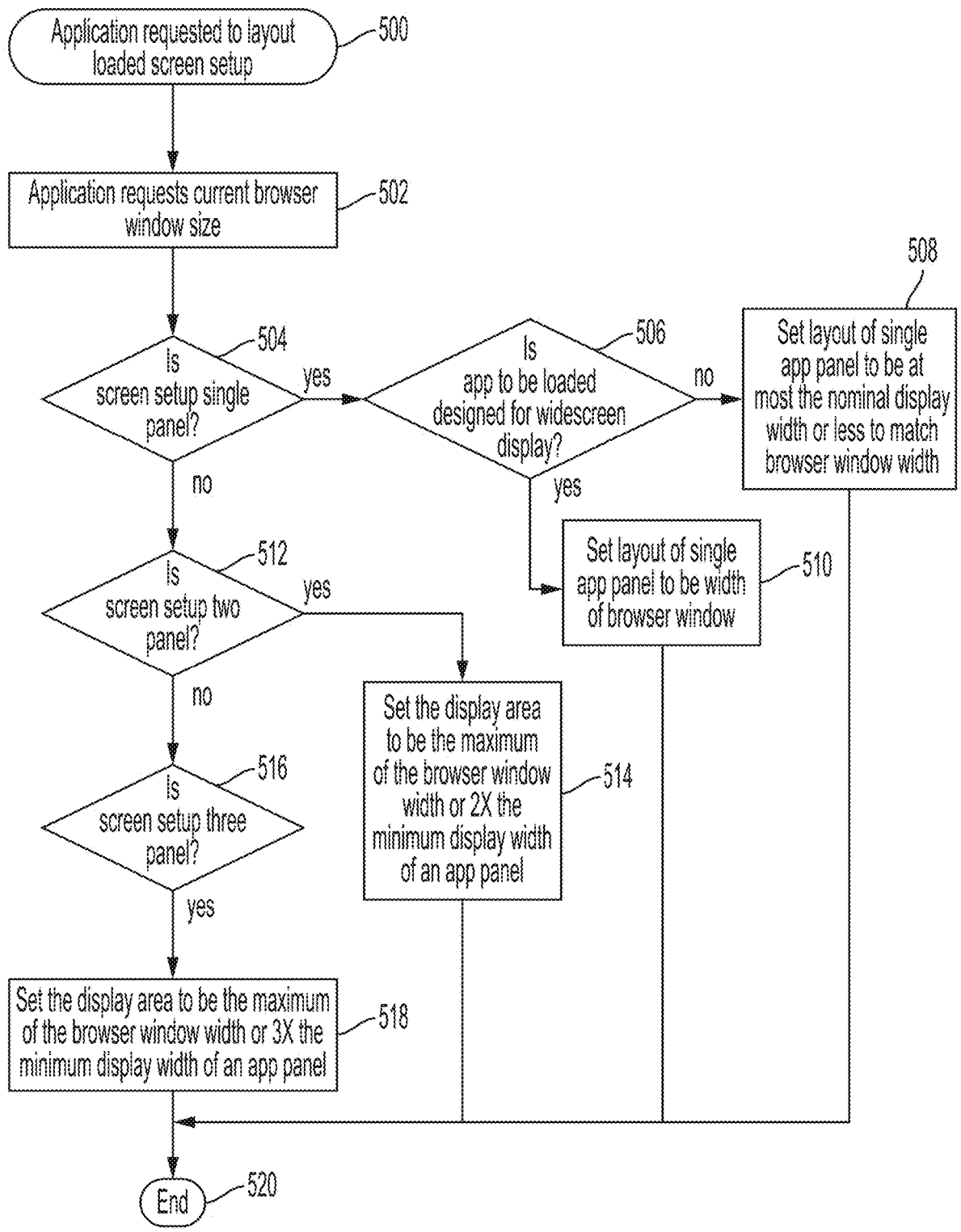
FIG. 5 depicts an exemplary process flow for the detection of and auto-adaptation to a desired display format for the user interface manager application.

FIG. 5 illustrates a methodology for detecting a display format and auto-adapting the content to the detected display format as described above in connection with FIG. 4. At step 500, a layout for display of an application on a particular screen setup is requested. The screen can, for example, be that of a standard desktop computer, a tablet computer, a laptop computer, a mobile phone, a wide screen monitor, an ultra-wide screen monitor, or a wall display (e.g., television or monitor), as described above. At step 502, a request is made by the application for the current browser window size. After the request in step 502, a determination is made at step 504 as to whether the screen is a single panel. If the determination at step 504 is "yes," the routine proceeds to a further determination at step 506 regarding whether the application to be loaded is designed for widescreen display. If the determination at step 506 is "no," the routine proceeds to step 508 and sets a layout of a single panel application to be at most a nominal display width or less to match a browser window width, and the routine then ends (at step 520). If the determination at step 506 is "yes," the routine proceeds to step 510 and sets a layout for a single panel application to become the width of the browser window, and the routine then ends (at step 520). If the determination at step 504 is "no" (i.e., the screen setup is not single panel), the routine proceeds to step 512 to make a determination as to whether the screen is a two-panel setup. If the determination at step 512 is "yes," the routine proceeds to step 514 and sets the display area to be the maximum of the browser window width or two times (2×) the minimum display width of an application panel and then ends (at step 520). If the determination at step 512 is "no" (i.e., the screen is not set up for two panel display), the routine proceeds to step 516 to make a determination as to whether the screen is a three-panel setup. If the determination at step 516 is "yes," the routine proceeds to step 518 and sets the display area to be the maximum of the browser window's width or three times (3×) the minimum display width of an application panel and then ends (at step 520). Moreover, certain applications may be boundless in that they can be expanded to occupy the entire real estate of the user interface, whereas other applications may be boundary limited and thus limited to a size less than the entirety of the real estate of the user interface. For example, for a boundless application, the user interface handles spanning of the application to a full width of the real estate of the browser, according to a width of the display.

Another aspect of the UEE that can be implemented as a result of display format auto-adaptation is a scrollability feature for the multi-panel view that is presented to the user. That is, a scrollable multi-panel view can be presented on the screen where a scroll tool provides the user with a virtual endless scroll capability for viewing all of the panels of the multi-panel display. For example, if a 3-panel view is presented on a monitor whose screen size is not sufficiently wide to readily accommodate a view of all 3 panels, the system can automatically adapt the presentation so that less than 3 panels are shown to the user on the screen at a given time, and a scroll tool can be included for interaction with by the user to scroll the view to the other panels of the multi-panel display. Such a scroll tool can take the form of a scroll bar that is displayed along the bottom edge of the screen.

Figure 14A:
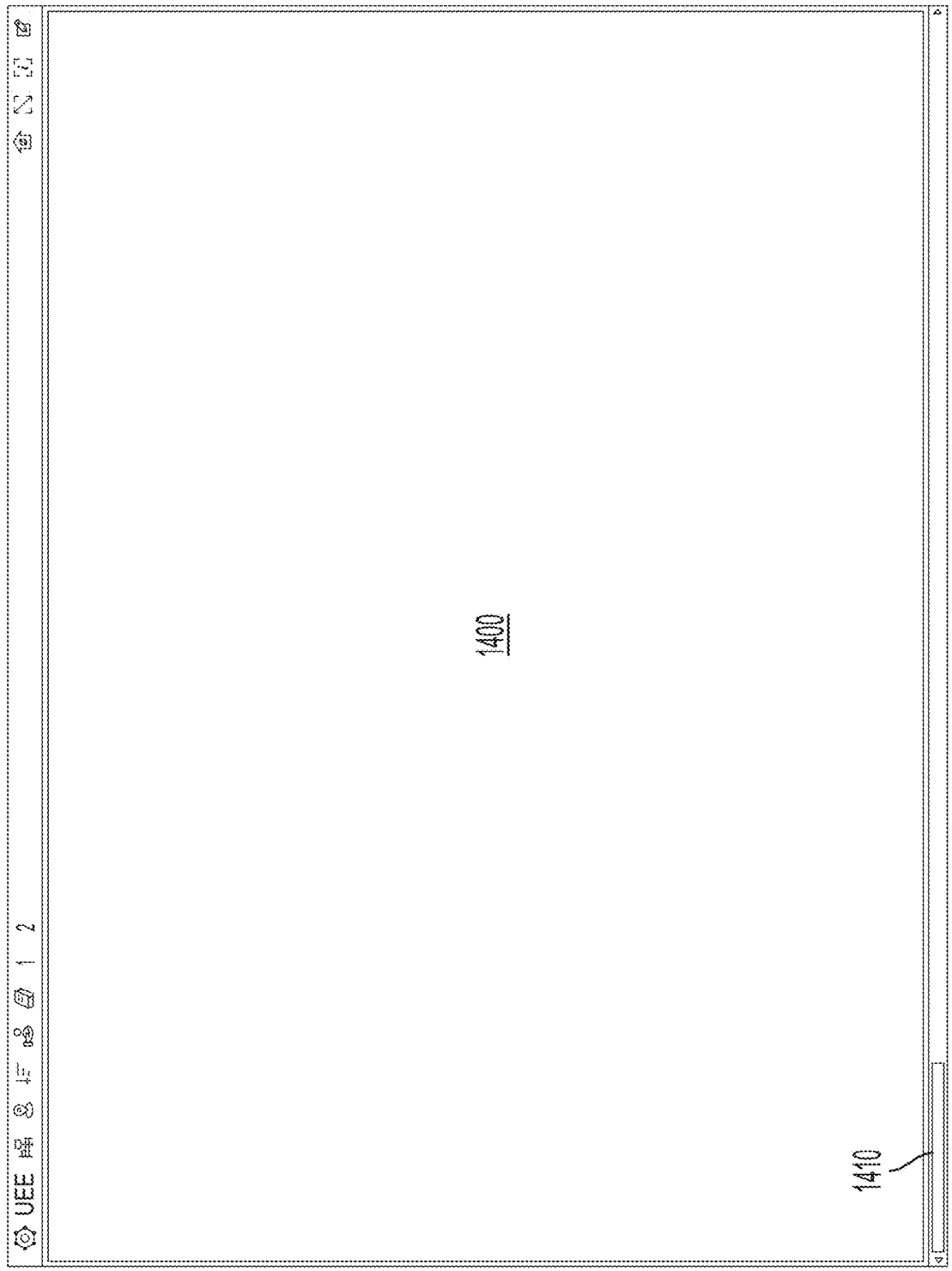
FIGS. 14A-14C show examples of scrollability for an example 2-panel view with respect to a first screen dimension.
Figure 14B:
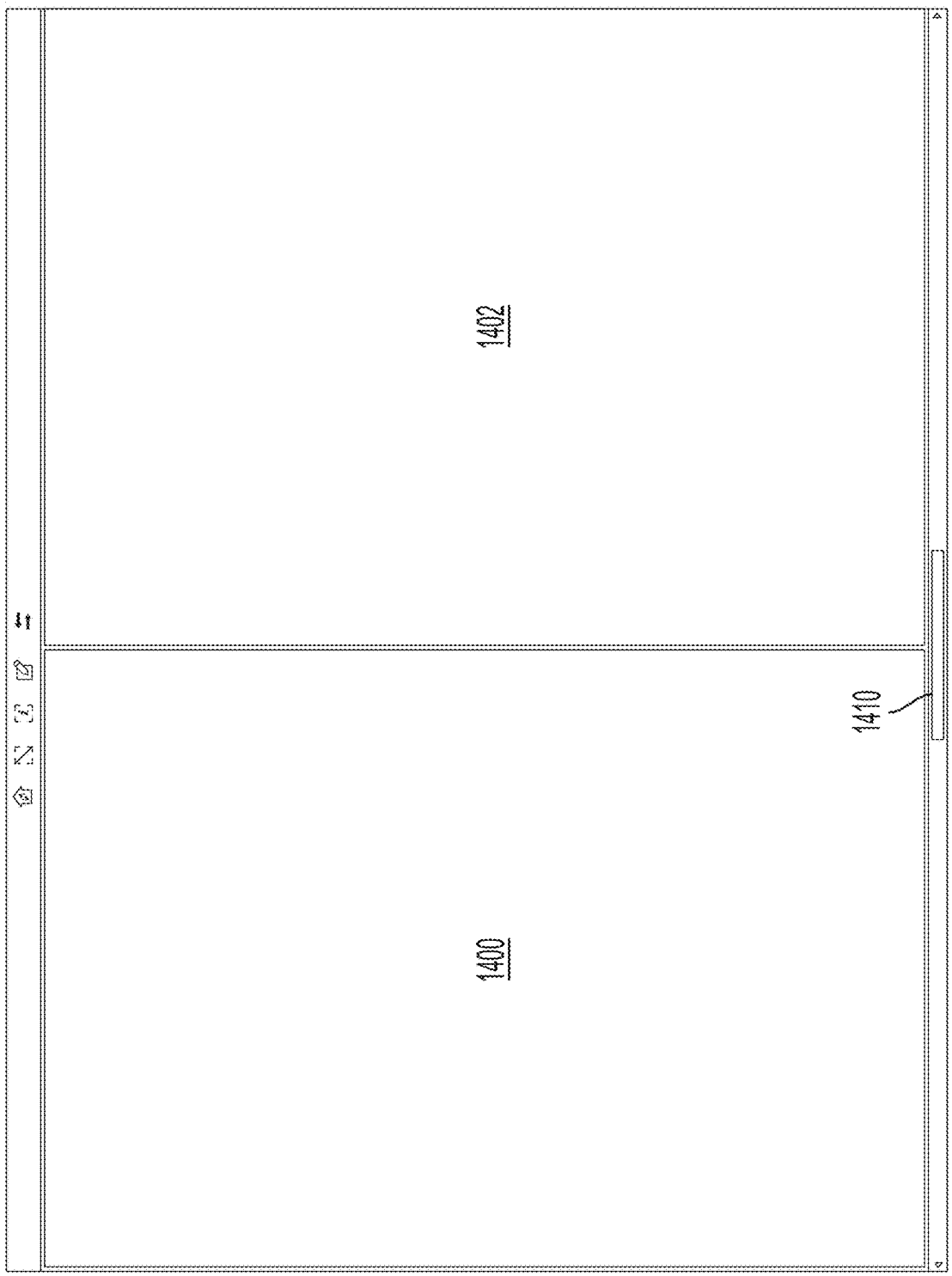
Figure 14C:
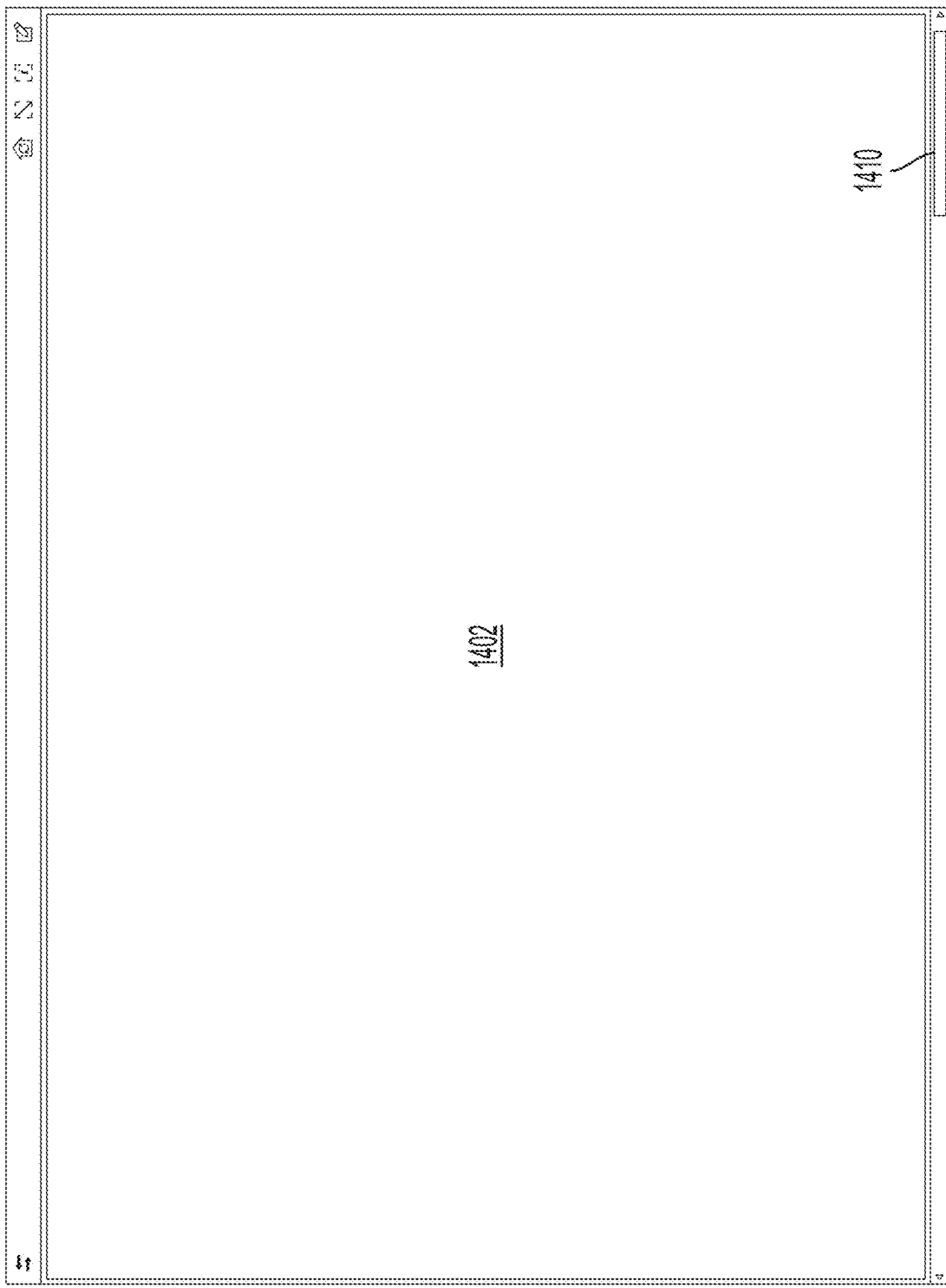

FIGS. 14A-14C show example screenshots where a 2-panel view is presented in a scrollable display format to better accommodate the display dimensions. FIG. 14A shows a view where the leftmost panel 1400 (Panel 1) is displayed in conjunction with scroll bar 1410. As the user uses the scroll bar 1402 to scroll the view to the right, a view like that shown by FIG. 14B is presented—where a portion of panel 1400 is shown as well as a left portion of panel 1404 (Panel 2). Then, as the user completes scrolling to the right (where scroll bar 1410 is in a rightwardly shifted position), a view like that shown by FIG. 14C is presented—where only panel 1402 (Panel 2) is seen.

Figure 15A:
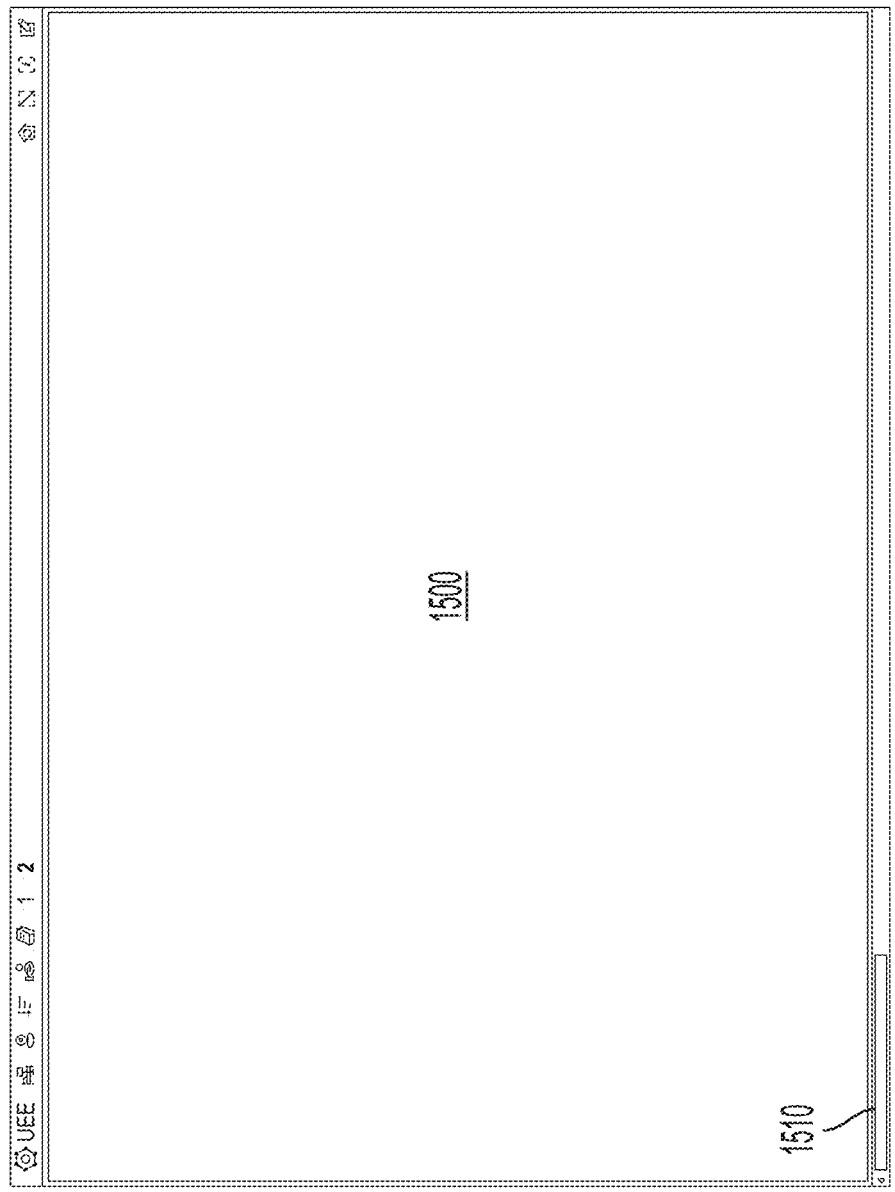
Figure 15B:
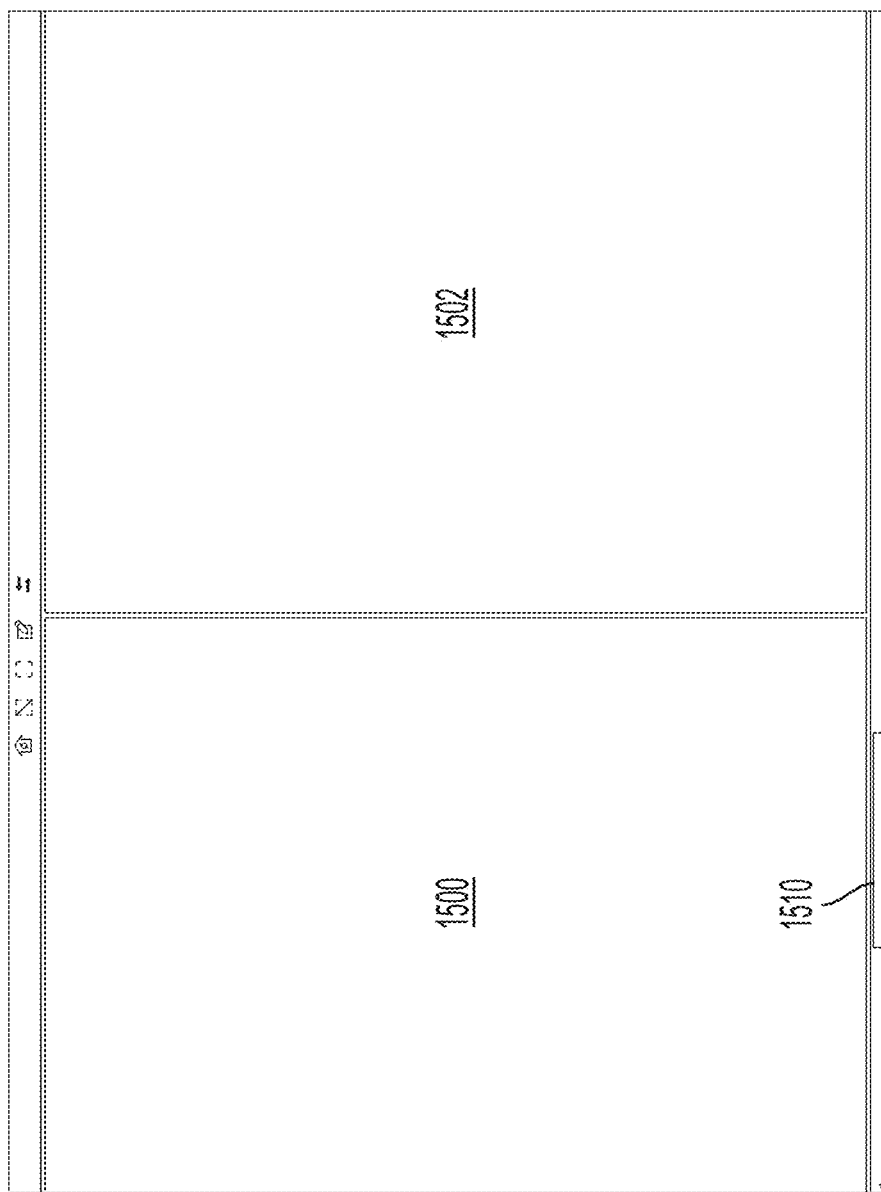
Figure 15E:
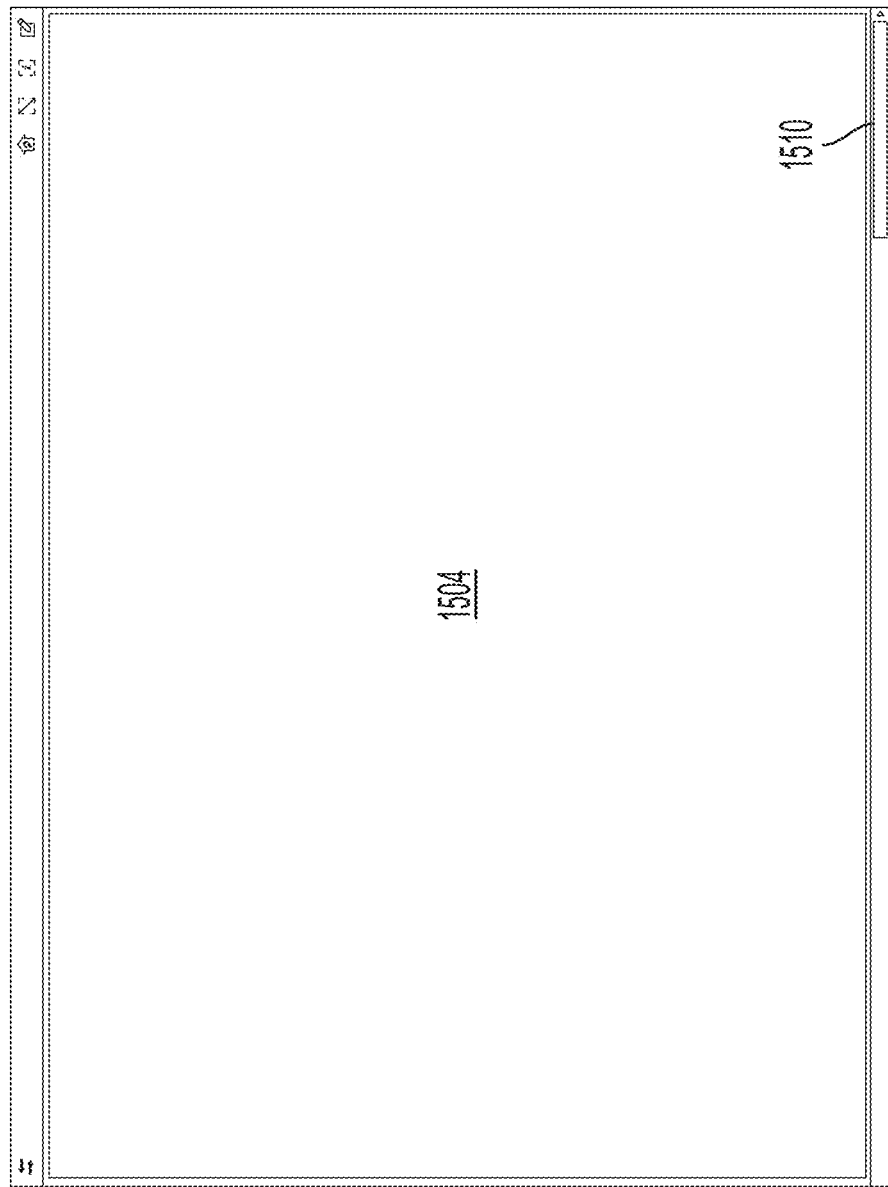

FIGS. 15A-15E show a similar set of example screenshots for scrolling with respect to a 3-panel view. In this example, FIG. 15A shows a scroll position for scroll bar 1510 where Panel 1 (1500) is seen. FIG. 15B shows a scroll position where portions of Panel 1 (1500) and Panel 2 (1502) are seen. FIG. 15C shows a scroll position where Panel 2 (1502) is seen. FIG. 15D shows a scroll position where portions of Panel 2 (1502) and Panel 3 (1504) are seen, and FIG. 15E shows a scroll position where Panel 3 (1504) is seen. It should be understood that similar scrollability would accommodate ever larger numbers of panels depending on how many panels the display is set up to present (e.g., a 4-panel view, 5-panel view, etc.).

Figure 16A:
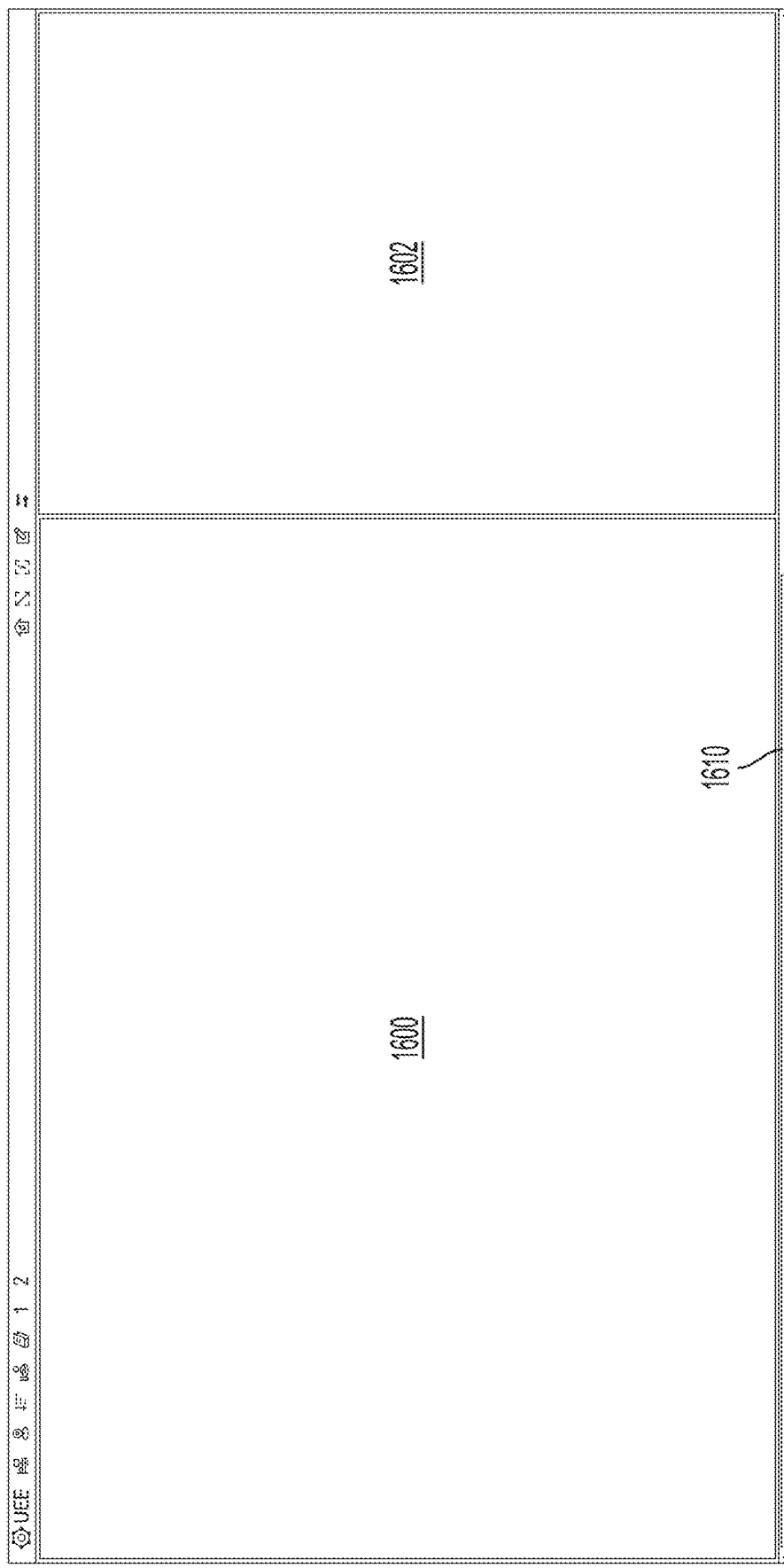
FIGS. 16A and 16B show examples of scrollability for an example 2-panel view with respect to a second screen dimension.
Figure 16B:
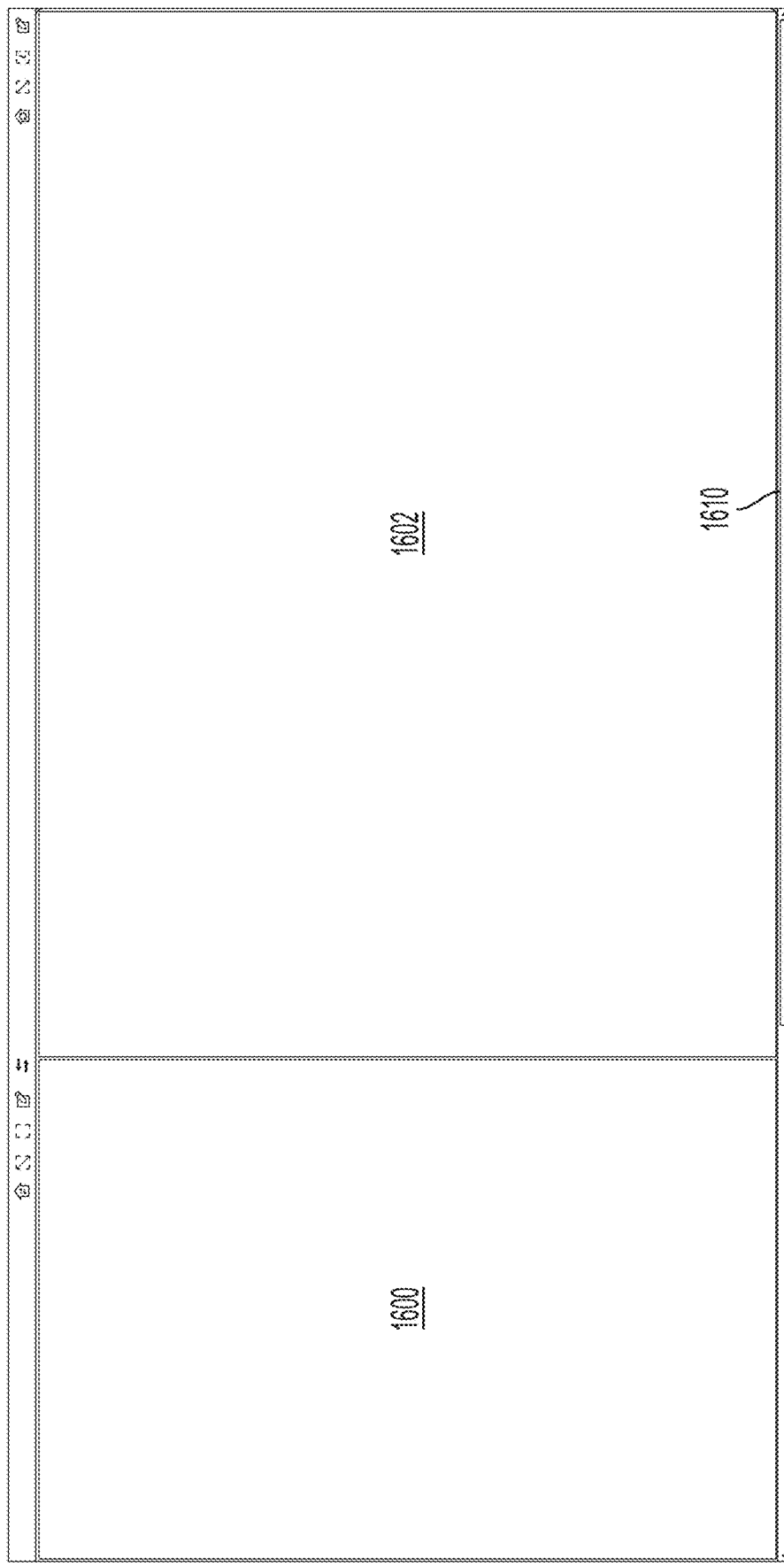
Figure 17C:
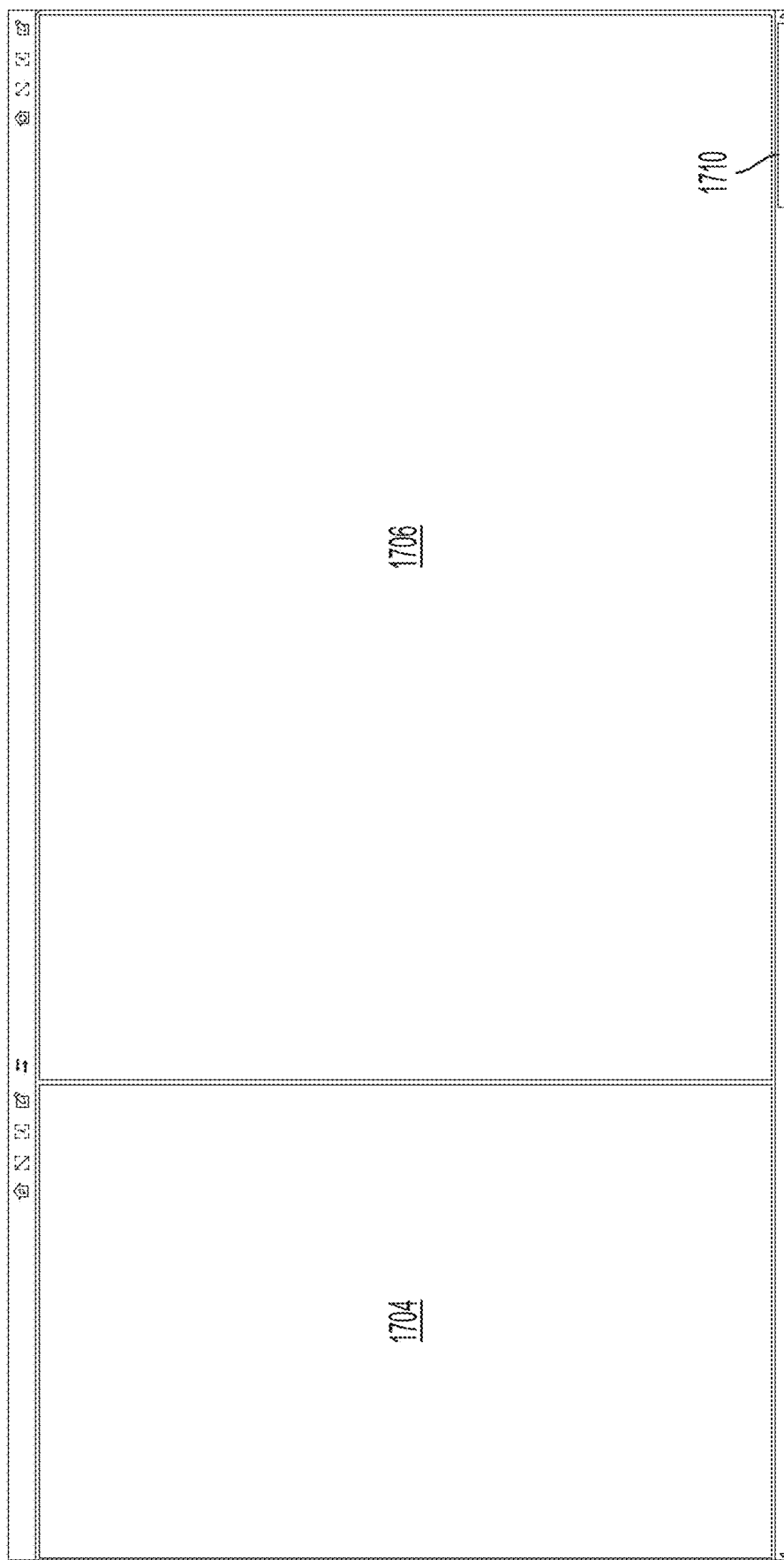

If the monitor is a bit wider than these two examples, the system can still accommodate auto-adaptation for such wider dimensions while still providing a virtual, endless scroll capability. For example, FIGS. 16A and 16B show an example 2-panel view on a wider screen. FIG. 16A shows Panel 1 (1600) and a left portion of Panel 2 (1602) while the scroll bar 1610 is in a leftward position, and FIG. 16B shows the view when the scroll bar 1610 has been shifted to the right (where a right portion of Panel 1 (1600) and Panel 2 (1602) are seen). As another example, FIGS. 17A-17C show an example 3-panel view on a wider screen. FIG. 17A shows Panel 1 (1700) and a left portion of Panel 2 (1702) while the scroll bar 1710 is in a leftward position. FIG. 17B shows the view when the scroll bar 1710 has been shifted to the right (where a right portion of Panel 1 (1700) and a left portion Panel 2 (1702) are seen), and FIG. 17C shows the view when the scroll bar 1710 has been shifted still further to the right (where a right portion of Panel 2 (1702) and Panel 3 (1704) are seen).

Figure 18:
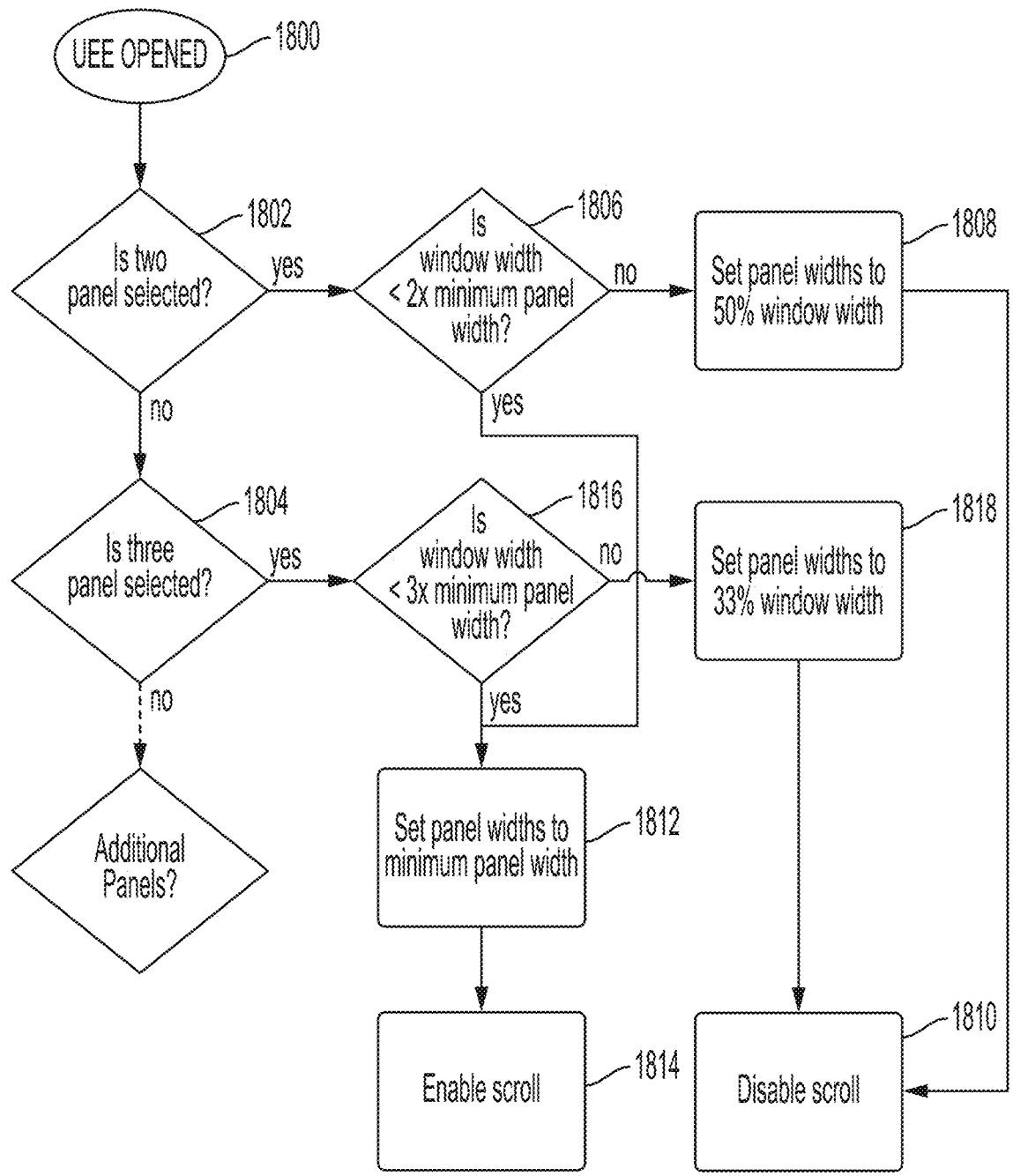
FIG. 18 shows an example process flow for auto-adapting panel presentation and scrollability based on screen dimensions.

FIG. 18 shows an example process flow for execution by a processor to implement auto-adaptive scrollability. At step 1800, the process flow begins as the UEE opens/launches. At steps 1802 and 1804, the processor determines whether the display is to exhibit 2 panels (step 1802) or 3 panels (1804).

If the processor determines that the UEE is to exhibit 2 panels, then the process flow proceeds to step 1806. At step 1806, the processor compares the window width for the UEE with the minimum panel width for the system. This comparison helps the system determine the nature of available display real estate for scaling of the panels within the multi-panel display. The processor can determine the UEE's window width by determining the width of the browser window (e.g., Google Chrome window width) which is a value known by and accessible from the browser. Alternatively, the processor can access known hardware settings for the subject computer system to determine monitor width. The determined UEE window width can serve as a proxy for the width of the user's screen. Thus, if a user has a widescreen monitor or ultra-widescreen monitor, this would be reflected in a relatively large value for the UEE window width. Similarly, if a user is accessing the UEE via a more conventionally-sized monitor, this would be reflected in a relatively smaller value for the UEE window width. The minimum panel width for the UEE can be a defined parameter that is selected to accommodate a practitioner's desires for including sufficient display real estate for presenting a computer application or website within a panel. The comparison at step 1806 can take the form of a determination whether the UEE's window width is less than two times (2×) the minimum panel width. If the UEE's window width is greater than 2× the minimum panel width, this means that the entirety of both of the panels can be displayed at the same time. In this circumstance, the process flow proceeds to step 1808. At step 1808, the processor sets the panel widths for each panel of the 2 panel display to be 50% of the UEE's window width. Given that both of the panels for the 2 panel display can be fully displayed at the same time, there is no need for a scroll capability; in which case the scroll feature is disabled (step 1810). If the UEE's window width is less than 2× the minimum panel width, this means that the entirety of both of the panels cannot be displayed at the same time. In this circumstance, the process flow proceeds to step 1812. At step 1812, the processor sets the panel widths for each panel of the 2 panel display to be the minimum panel width. Since the entirety of both panels will not fit on the screen at the same time, this means a scroll capability is needed in order to access the second panel (or portions thereof). Accordingly, at step 1814, the scroll feature is enabled so that a scroll bar is included as part of the UEE as discussed above and shown by the examples of FIGS. 14A-C and 16A-B.

If the processor determines that the UEE is to exhibit 3 panels, then the process flow proceeds to step 1816. At step 1816, the processor compares the window width for the UEE with the minimum panel width for the system by determining whether the UEE's window width is less than three times (3×) the minimum panel width. If the UEE's window width is greater than 3× the minimum panel width, this means that the entirety of all 3 panels can be displayed at the same time. In this circumstance, the process flow proceeds to step 1818. At step 1818, the processor sets the panel widths for each panel of the 3 panel display to be 33% of the UEE's window width. Given that all 3 panels of the 3 panel display can be fully displayed at the same time, there is no need for a scroll capability; in which case the scroll feature is disabled (step 1810). If the UEE's window width is less than 3× the minimum panel width, this means that the entirety of all 3 panels cannot be displayed at the same time. In this circumstance, the process flow proceeds to step 1812, which operates as discussed above. From step 1814, the process flow proceeds to step 1814 where the scroll feature is enabled so that a scroll bar is included as part of the UEE as discussed above and shown by the examples of FIGS. 15A-E and 17A-C.

While the example of FIG. 18 describes auto-adaptive scrolling in the context of 2 panel displays and 3 panel displays, it should be understood that the same approach can be used in extending the process to layouts with additional panels (e.g., 4 panel displays, 5 panel displays, etc.) so that the system can automatically adapt the scaling and scrolling that may be needed to accommodate additional numbers of panels on the multi-panel display.

Figure 6A:
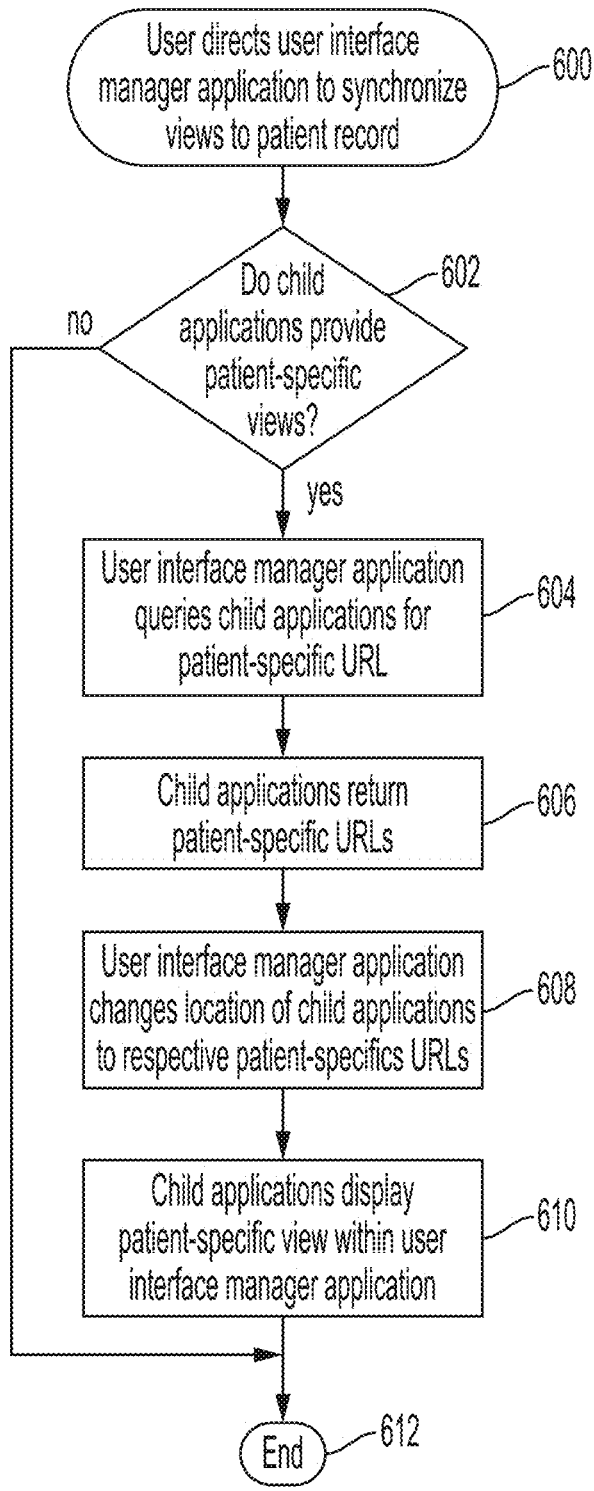
FIG. 6A illustrates a unidirectional approach to synchronization of multiple applications displayed within the user interface manager application.

FIG. 6A illustrates a first process flow for view synchronization. At step 600, the user directs the user interface application manager to synchronize views to a particular patient record. The applications displayed by the UEE can include hierarchical relationships where one of the applications is a parent application and one or more of the other applications is a child application. The FIG. 6A process flow involves instances where a user seeks to synchronize views via input at step 600 in the parent application. In this context, the process flow of FIG. 6A can be referred to as unidirectional view synchronization. At step 602, a determination is made as to whether any child applications provide patient-specific views. If the determination made at step 602 is "yes," then the process flow proceeds to step 604, whereby the user interface application manager queries child applications for corresponding patient-specific details such as URLs. For example, each application may include its own URL for a particular patient. At step 606, the child applications return their respective patient-specific URLs. At step 608, the user interface manager application changes locations of the child applications to the respective patient-specific URLs. At step 610, the child applications then display their patient-specific views within the user interface manager application such that the overall user interface manager application is configured to convey information pertaining to that particular patient. The unidirectional synchronization process flow then ends (see step 612). If the determination made at step 602 is "no," then the unidirectional process flow ends (see step 612).

Figure 19A:
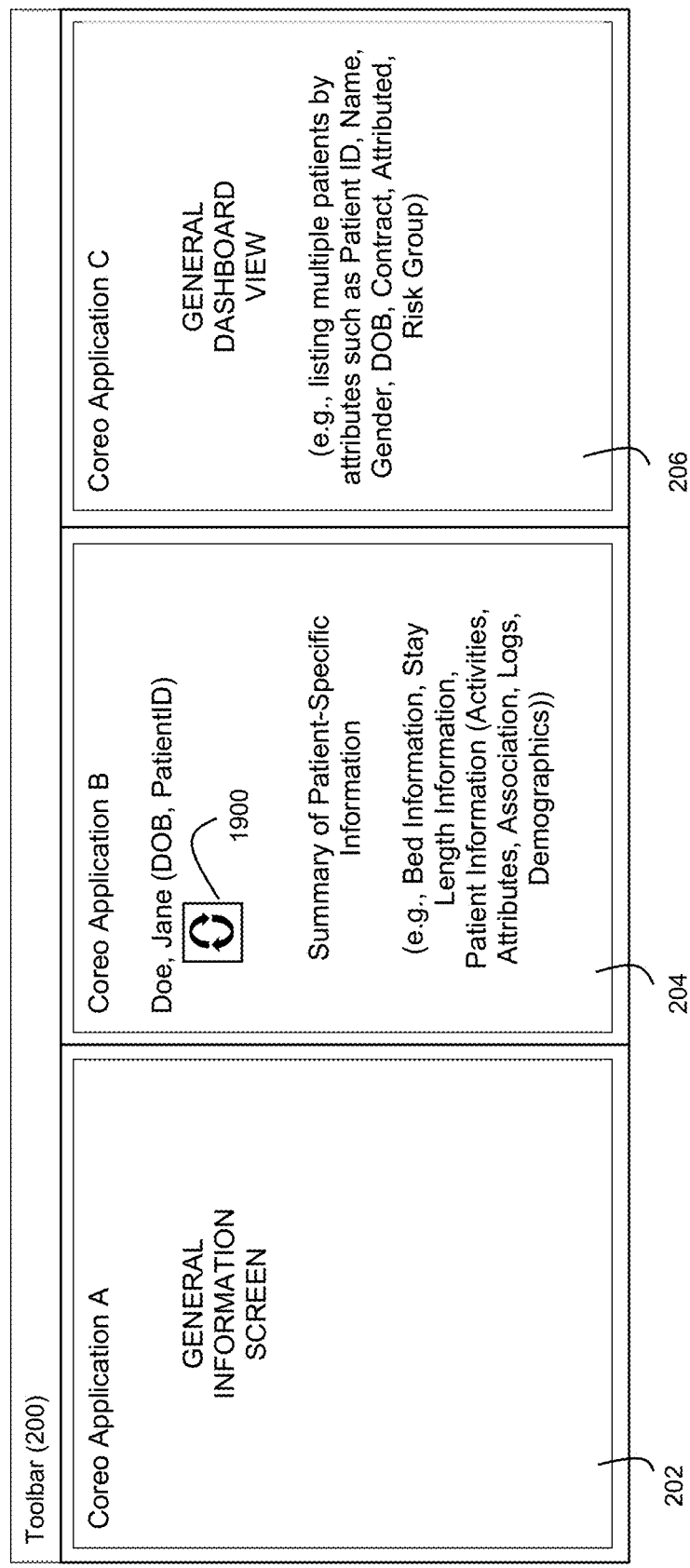
FIGS. 19A and 19B show example multi-panel displays relating to the unidirectional synchronization of FIG. 6A.
Figure 19B:
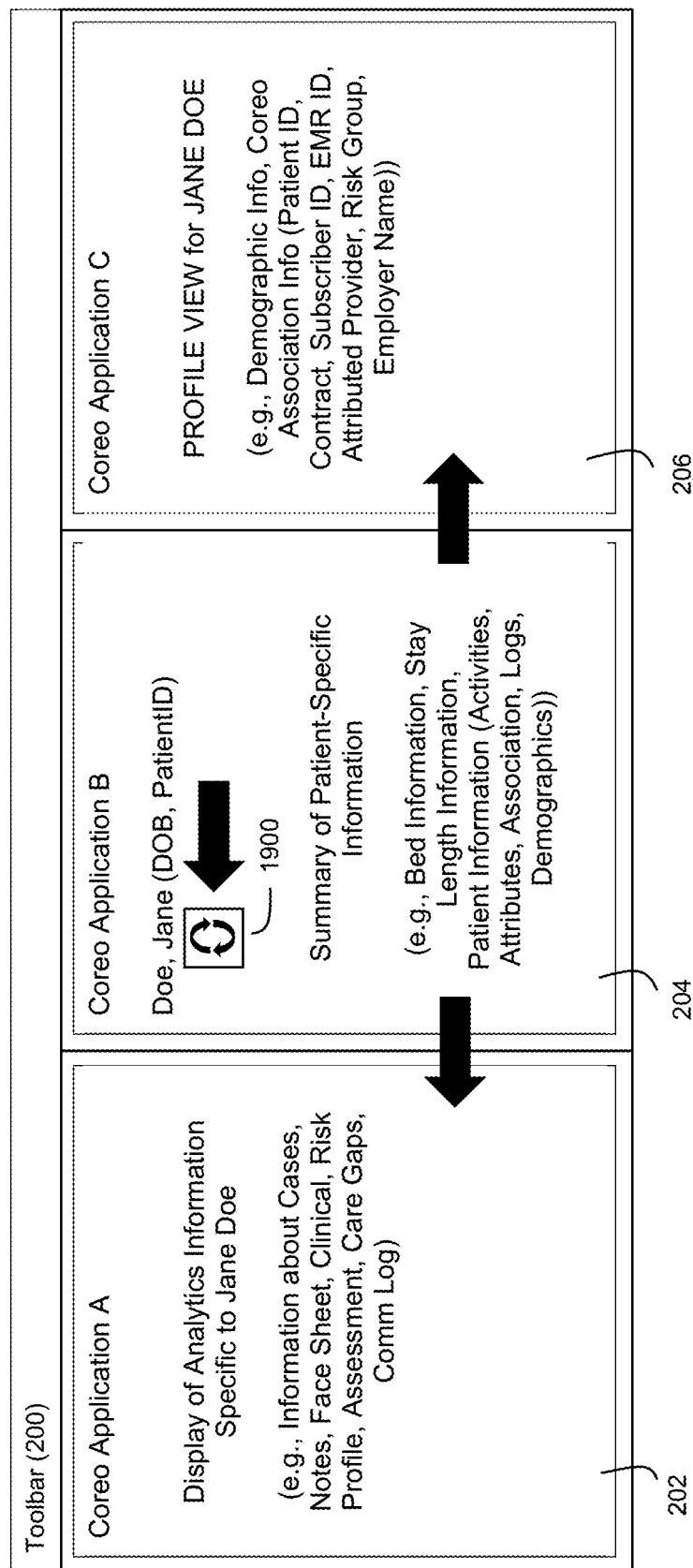

FIG. 19A shows an example of a 3-panel UEE display before unidirectional view synchronization is performed. In panel 202 of FIG. 19A, an application such as COREO™ Application A is presented. This application in this example can be in a state where it shows general information that is not patient-specific. In panel 204 of FIG. 19A, an application such as COREO™ Application B is presented. COREO™ Application B in this example can be in a state where it provides a summary of information specific to a particular patient (e.g., Jane Doe as shown by FIG. 19A). In panel 206 of FIG. 19A, an application such as COREO™ Application C is presented. COREO™ Application C in this example can be in a state where it provides a general dashboard view that lists a number of different patients and their associated attributes. COREO™ Application B in this example can serve as the parent application, while COREO™ Applications A and C can serve as child applications. The UEE shown by FIG. 19A includes a view synchronization button 1900 in panel 204, which allows a user to synchronize the views in the UEE to the specific patient that is the subject of the application presented by panel 204. Thus, user selection of button 1900 will trigger execution of the FIG. 6A process flow, where the other applications are updated to reflect information for the specific patient shown by panel 204 (Jane Doe). FIG. 19B shows the result of this unidirectional view synchronization. As shown by FIG. 19B, user selection of the view synchronization button 1900 in panel 204 has caused the applications in panels 202 and 206 to reflect information specific to the synchronized patient (Jane Doe).

Figure 6B:
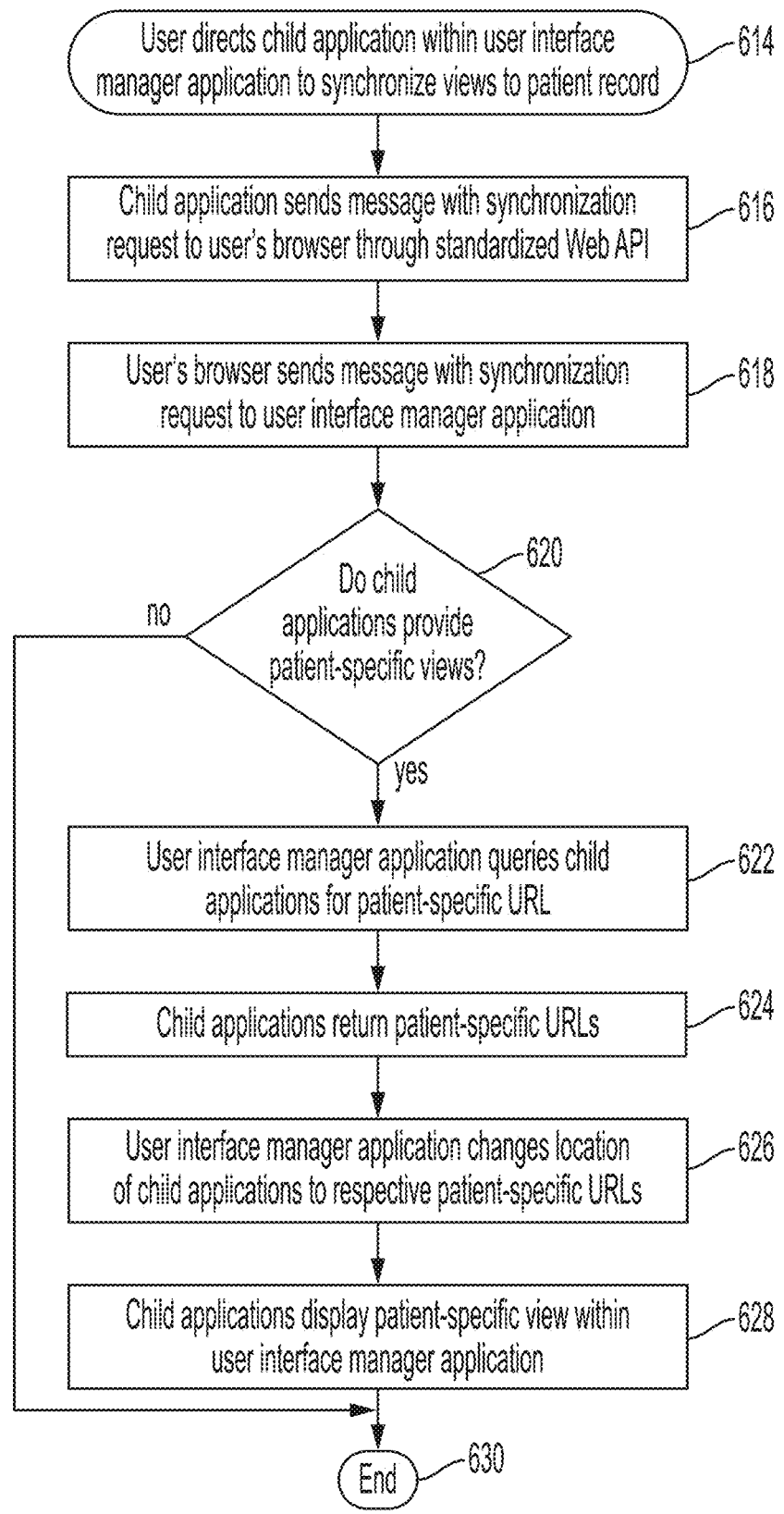
FIG. 6B illustrates a bidirectional approach to synchronization of multiple applications displayed within the user interface manager application.

FIG. 6B illustrates a second process flow for view synchronization. With the process flow of FIG. 6B, user input in a child application causes an adjustment to the display state for the parent application and any sibling applications. In this context, the process flow of FIG. 6B can be referred to as bidirectional view synchronization. At step 614, the user directs a child application within the user interface manager application to synchronize views to a particular patient record. At step 616, the child application sends a message with a synchronization request to the user's browser. This messaging/requesting may be performed in the browser through a standardized web API. At step 618, the user's browser sends a message with a synchronization request to the user interface manager application. Next, at step 620, a determination is made as to whether the parent and sibling applications have patient-specific views. If the determination at step 620 is "yes," then at step 622, the user interface manager application queries the parent and sibling applications for corresponding patient-specific URLs. Then, at step 624, the parent and sibling applications return respective patient-specific URLs. At step 626, the user interface manager application changes the locations of the parent and sibling applications to the respective patient-specific URLs. At step 628, the parent and sibling applications display their respective patient-specific views within the user interface manager application, such that the overall user interface manager application is configured for display, throughout the various applications, of information pertaining to that particular patient. The bidirectional process flow then ends (see step 630). If the determination at step 620 is "no," then the bidirectional process flow ends (see step 630).

Figure 20A:
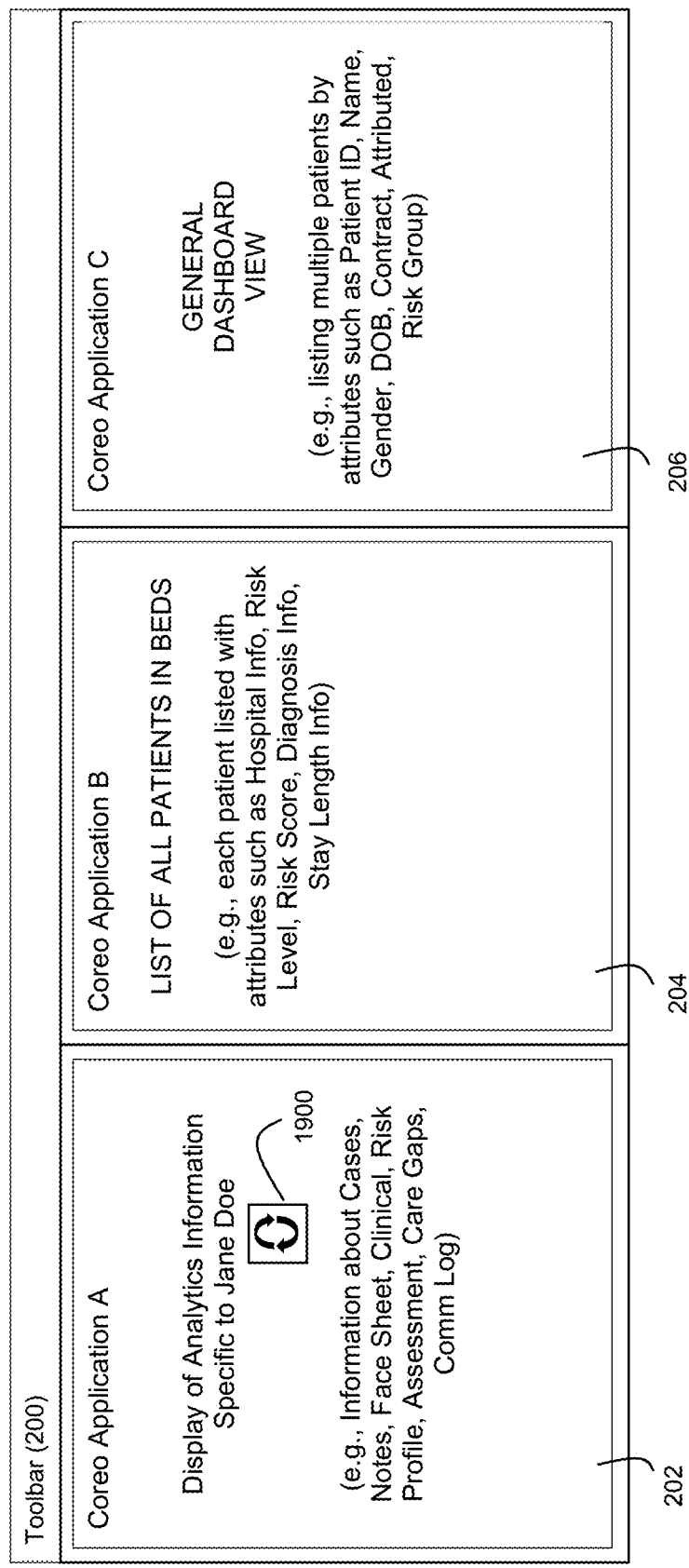
FIGS. 20A and 20B show example multi-panel displays relating to the bidirectional synchronization of FIG. 6B.
Figure 20B:
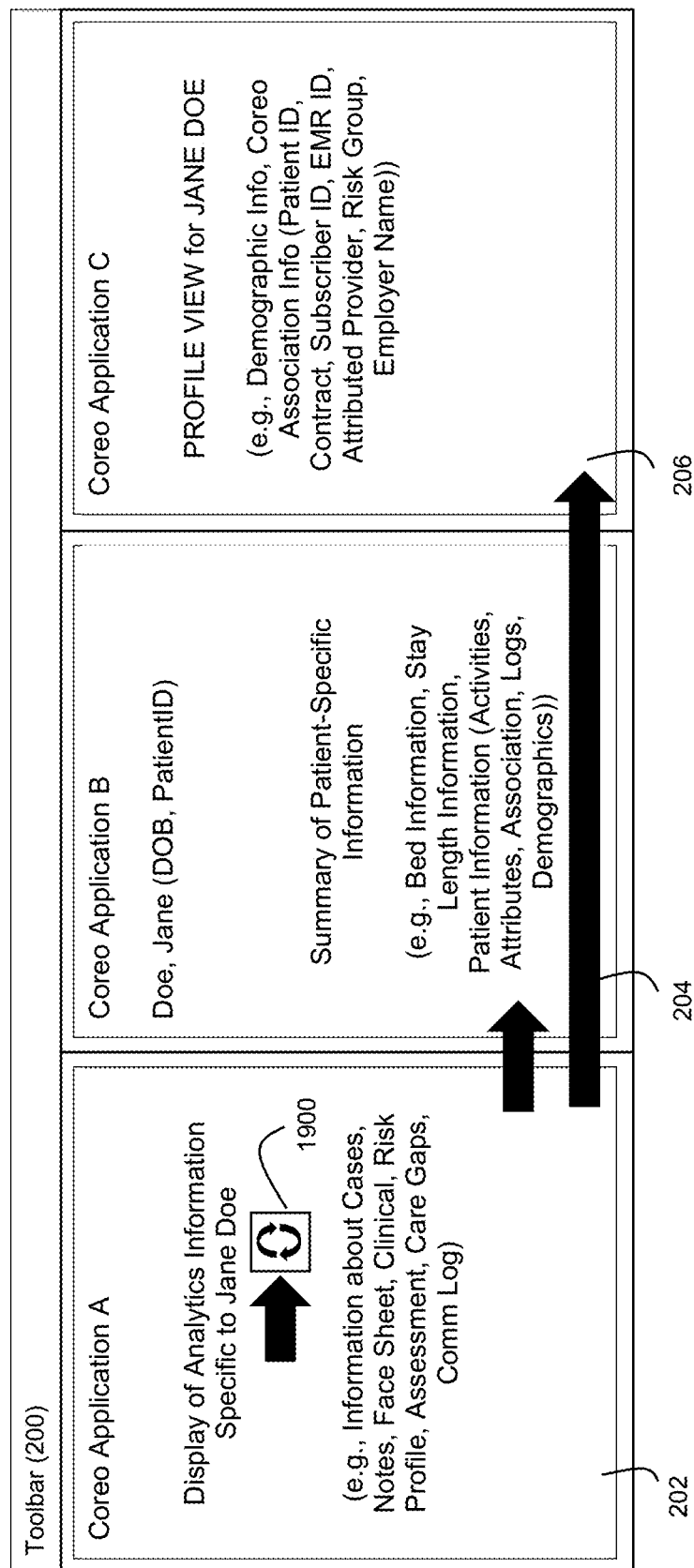

FIG. 20A shows an example of a 3-panel UEE display before bidirectional view synchronization is performed. In panel 202 of FIG. 20A, an application such as COREO™ Application A is presented. This application, which as noted above serves as a child application, in this example can be in a state where it shows information specific to a patient (Jane Doe). In panel 204 of FIG. 20A, an application such as COREO™ Application B is presented. COREO™ Application B in this example serves as the parent application, and it can be in a state where it provides information about multiple patients in beds (along with associated attributes about each such patient). In panel 206 of FIG. 20A, an application such as COREO™ Application C is presented. COREO™ Application C, which as noted above serves as a child application (or sibling to COREO™ Application A), in this example can be in a state where it provides a general dashboard view that lists a number of different patients and their associated attributes. User selection of the view synchronization button 1900 will trigger execution of the FIG. 6B process flow, where the parent and sibling applications (COREO™ Applications B and C) are updated to reflect information for the specific patient shown by panel 202 (Jane Doe). FIG. 20B shows the result of this bidirectional view synchronization. As shown by FIG. 20B, selection of the view synchronization button 1900 has caused the applications in panels 204 and 206 to reflect information specific to the synchronized patient (Jane Doe).

Figure 7A:
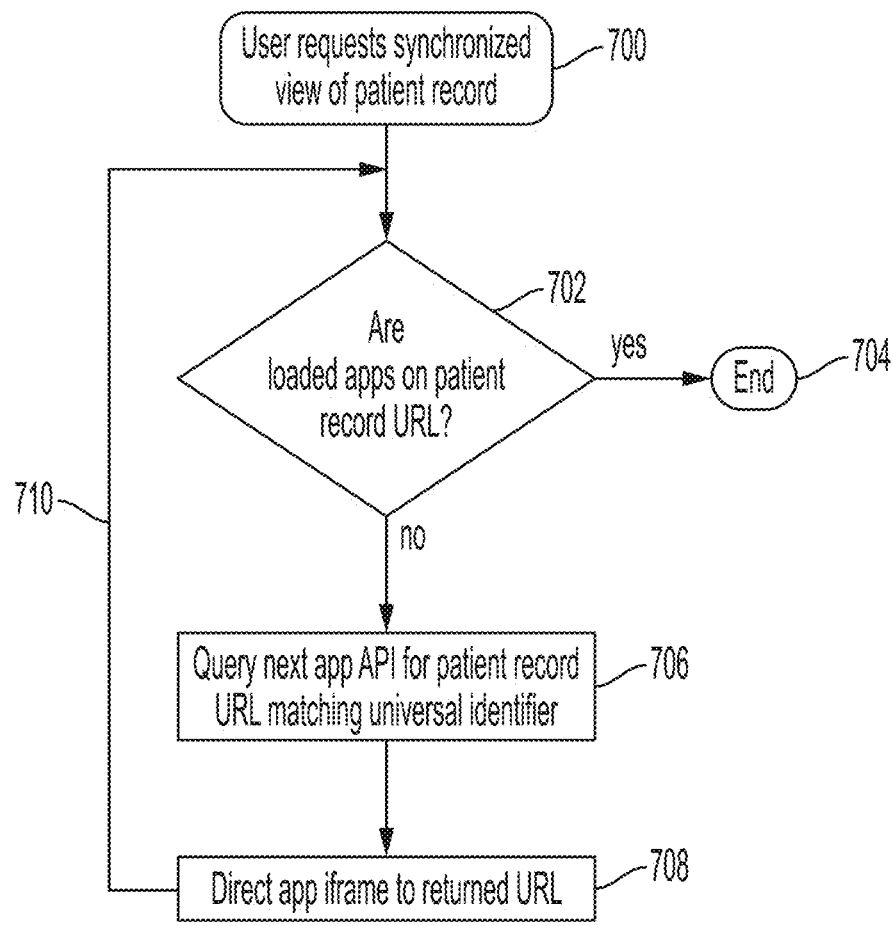
FIG. 7A depicts an exemplary process flow for unidirectional view synchronization via deep linking according to patient data.

FIG. 7A illustrates a flow diagram for carrying out view synchronization via deep linking. At step 700, a user requests a synchronized view of a patient record. After the user request, there is advancement to step 702, which is a determination as to whether or not there are loaded applications on the patient record URL. If the determination at step 702 is "yes", the routine proceeds to step 704, an end point. If the determination at step 702 is "no", the routine proceeds to step 706. Step 706 is a query for a next application API for a patient record URL that matches a universal identifier. Then, at step 708, a direct application iframe is attributed to a returned URL. The process flow can then revert, via step 710, back to at point before step 702, to repeat a determination as to whether there are any loaded applications on a patient record URL. From a holistic viewpoint, after such synchronization, a patient specific view comprising information such as claims records, care plans, and appointments is shown in the user interface manager application by way of the various applications loaded in the user interface manager application.

Figure 7B:
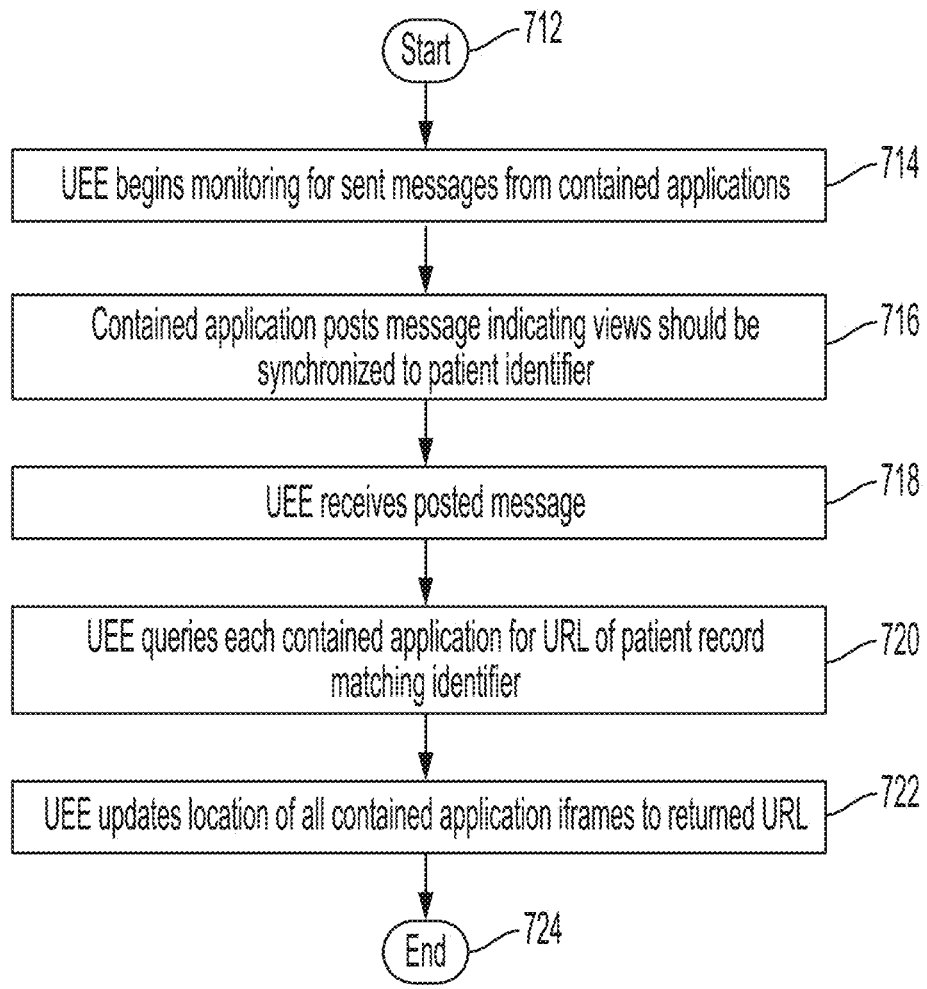
FIG. 7B depicts an exemplary process flow for unidirectional view synchronization via deep linking according to event data.

FIG. 7B illustrates a process flow for how the user interface manager application manages a healthcare event (such as a particular ED event or other event that occurs within an application). After the start of the process flow (step 712), the UEE begins monitoring for healthcare events leveraging the contained applications (step 714). Examples of types of event data that can trigger changes in context and/or display layouts can include events such as a patient ED visit, a patient admission/discharge, a medication trend, a population diagnosis trend, and others. Then, at step 716, a contained application identifies a healthcare event which should automatically change the context of the applications displayed in the user interface manager application to optimally display the right information at the right time among a plurality of applications for immediate context by a healthcare user. For example, a patient-specific event can trigger a change in the context of displayed applications so that the displayed applications are synchronized to the specific patient corresponding to the event. As another example, a collection of events can be tracked and monitored via the UEE to trigger changes in the applications. For example, medication events can be tracked and monitored to detect medication trends (e.g., rising/falling incidents of administrations of Medication X, rising instances of adverse patient effects following administrations of Medication Y, etc.). Furthermore, diagnostic events can be tracked and monitored to detect population diagnosis trends (e.g., increases in COVID-19 incidents within a community, etc.). At step 718, the user interface manager application receives the posted message. At step 720, the user interface manager application queries each contained application for a respective URL of a patient record matching identifier. At step 722, the user interface manager application updates the location of all contained iframes to a returned URL, and the routine ends at step 724. For example, the applications are all directed to their respective patient-specific URLs that are associated with the matching global patient identifier. This allows for a single patient view to result from the various applications all loading the URL associated with the same patient. As described above, modern browsers implement a standard API that includes the ability to post a message that is delivered to any webpage or application within an embedded iframe or the containing webpage. The receiving page must implement an event listener such that it is notified of the message that is being sent. Through this mechanism, the user interface manager application can send or receive messages to any of the applications contained within it. This communication mechanism is primarily utilized for purposes including to be notified of session activity (e.g., SSO session) and to notify other contained applications to keep their associated sessions alive. Alternatively, deep-linking commands may be delivered to iframes within the UEE to allow for i) application view synchronization and ii) application context changes for each contained application so that all the contained applications are directed to the respective patient record view and application screen, although other purposes are envisioned. In doing so, the user experience is benefitted by maintaining session activity and automatically displaying relevant application context representing a significant improvement of conventional techniques in the art.

Figure 8A:
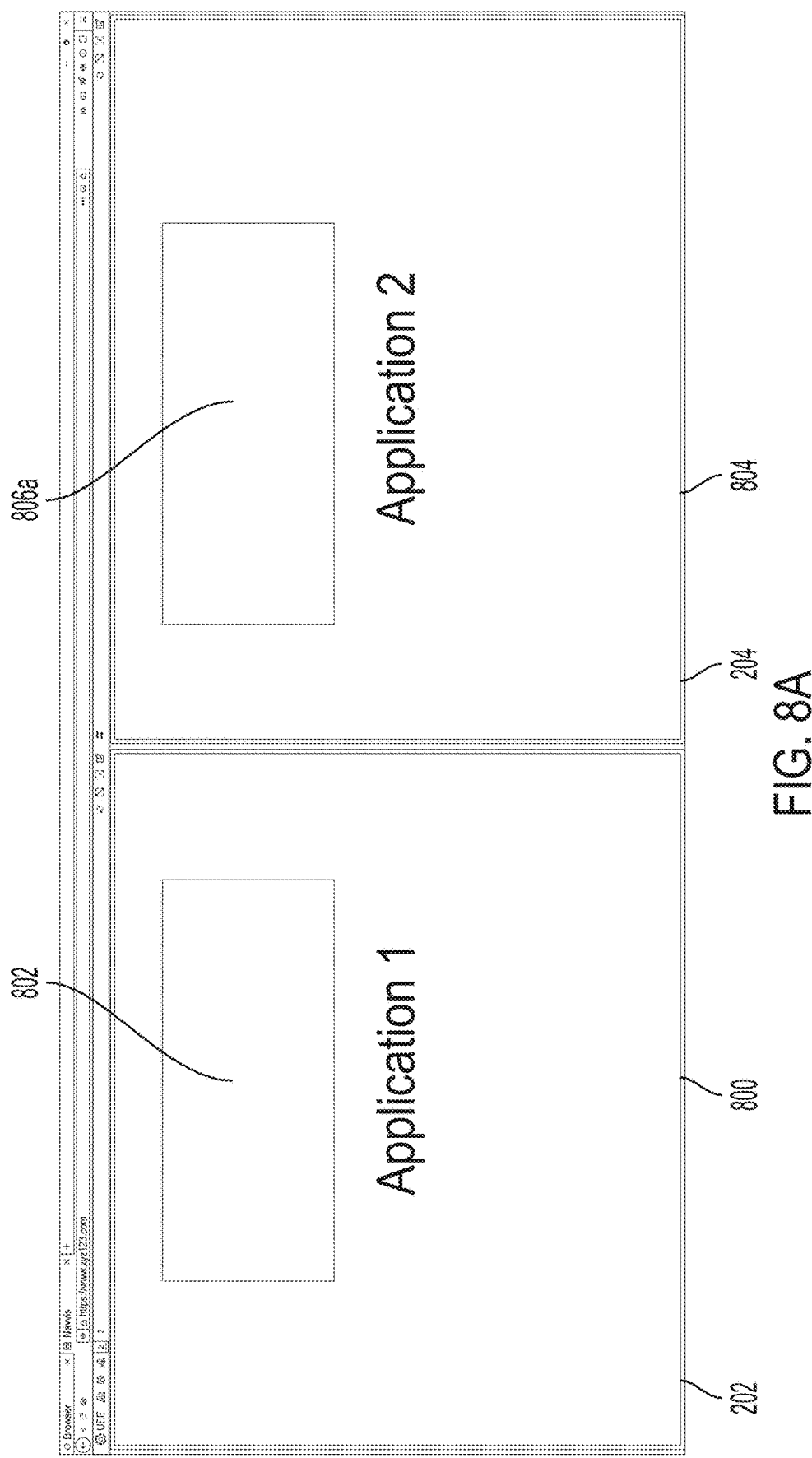
FIG. 8A illustrates a patient data interface prior to a user input.
Figure 8B:
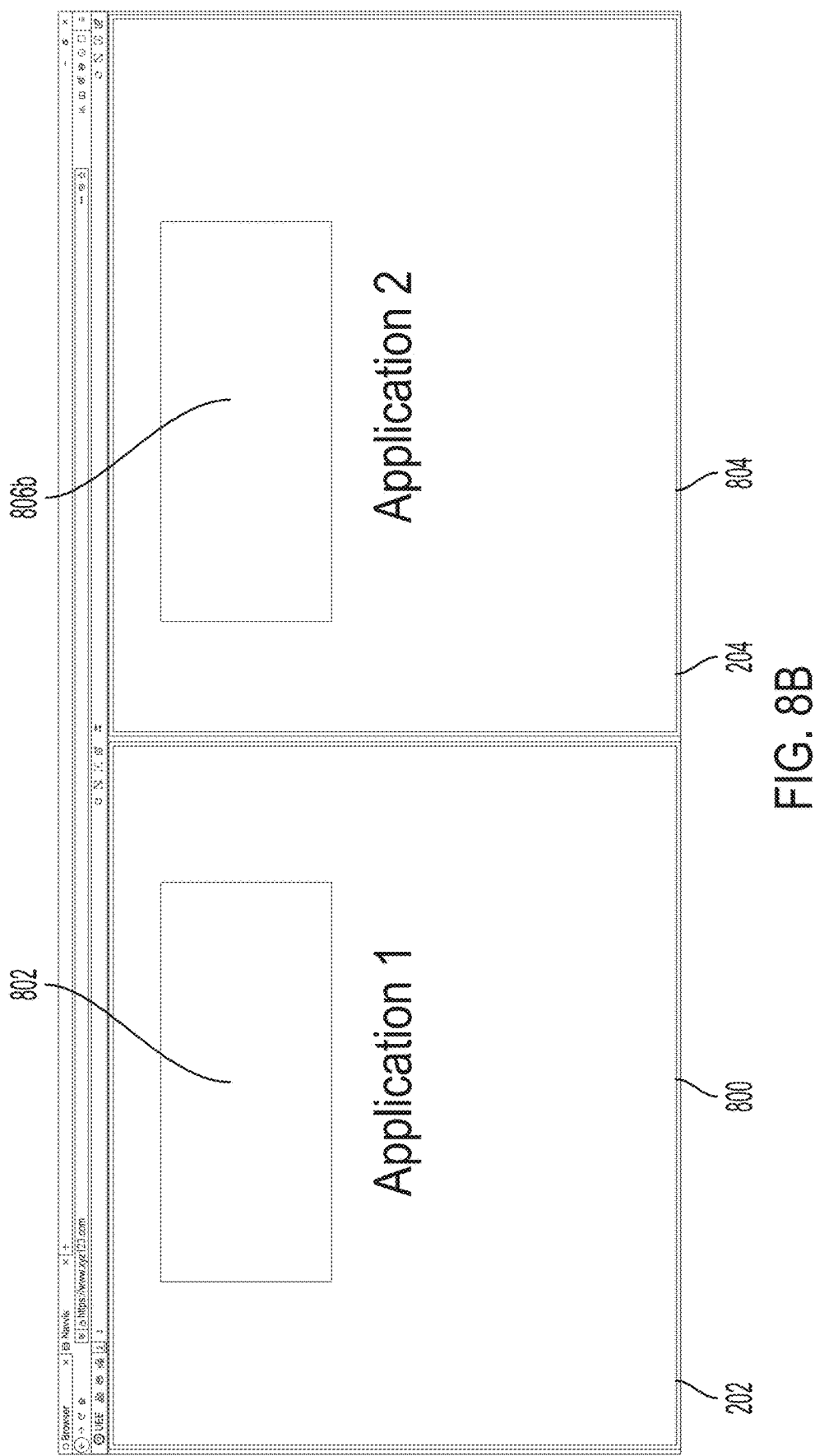
FIG. 8B illustrates the patient data interface according to FIG. 8A after a user input.

FIGS. 8A and 8B illustrate an example of contextual linking between applications in the panels of the user interface manager application. For example, in FIG. 8A, the left panel 202 shows a first application 800 (e.g., Application 1) which may include a window 802 of first information (e.g., information of a particular patient, such as name, gender, date of birth, an alphanumeric identifier, etc.). This information may include various risk levels such as high, moderate or low with a sublevel to observe the patient. There may also be an indication of the status of the patient, such as stable. There may also be demographics information that may include such data as a primary email, address, city, state, zip code, phone number, etc. The right panel 204 shows a second application 804 (e.g., Application 2) which includes a window 806a of second information (e.g., a dashboard of tasks, appointments and work queues). The second information in window 806a may be unrelated to the first information in window 802. A user can select certain information or carry out other user selections in the applications shown in FIG. 8A, which causes a contextual reaction in an adjacent panel, as illustrated in FIG. 8B. As shown in FIG. 8B, after a particular user input in the window 802 of the left panel 202 as shown in FIG. 8A has occurred, further information of the patient may be contextually displayed in window 806*b*. Thus, the previous window 806*a* of information unrelated to the information in window 802 is updated to window 806*b* which displays information that is contextually-linked to the information in window 802. This capability allows healthcare users greater efficiency since the clicks required to change the context of each currently displayed or hidden adjacent application panel require time and the UEE can help ensure that the optimal context of each currently displayed or hidden adjacent application panel is maintained at all times. In Application 2 in the right panel 204 as shown in FIG. 8B, there may be, for example, a left information column may include a health summary, immunizations, metrics, lifestyle, history, procedure, gaps in care, care coordination, financial information and reports. The window 806*b* may include information pertaining to allergies, current medications, diagnoses, programs, waiting lists, risk scores, tasks/appointments, care team, scoring and outcomes, and insurance details. The patient demographics may also be re-displayed with expanded information such as legal contact information, Medicaid/Medicare ID, primary care provider (PCP) information, and primary language. There may also be additional functional elements such as fields to enter alerts or separate portions that serve as a communication center. Additional aspects include setting a flag to follow a patient in one panel. Thus, FIGS. 8A and 8B represent an example of how applications loaded within the user interface manager application can be contextually updated based on user input which as described herein is a significant improvement over conventional techniques.

Figure 9A:
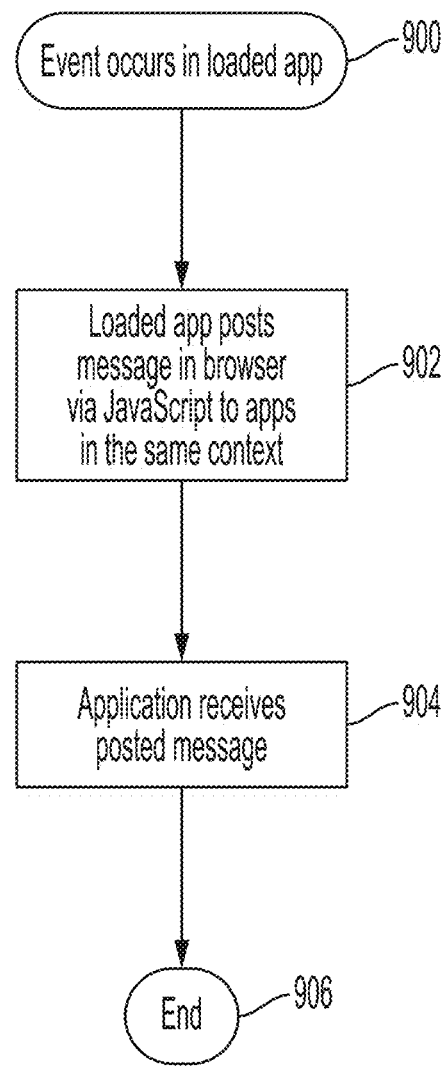
FIG. 9A depicts an exemplary process flow for changing an application/URL view based on events/inputs in different applications/URLs.

FIG. 9A depicts a process flow for changing views in other applications/websites based on events and/or user inputs in a different application/website, as shown, for example, in FIGS. 8A and 8B. At step 900, an event occurs or a user input is performed in a loaded application. At step 902, the loaded application posts a message in the browser (e.g., via JAVASCRIPT® available from Oracle America, Inc.) to applications in the same context. For example, if the event relates to a particular patient (e.g., a particular patient is selected via one of the applications), the posted message can include patient demographic data, which allows the other applications and/or websites to snap their views to the contextually-relevant patient. Then, at step 904, the loaded application(s) receive the posted message such that they are contextually updated in accordance with the other loaded applications, and the routine ends at step 906. To enable this capability, deep-linking commands may be delivered to iframes within the UEE to allow for i) application view synchronization and ii) application context changes for each contained application so that all the contained applications are directed to the respective patient record view and application screen, although other purposes are envisioned. Applications can be automatically displayed and directed to a particular screen within each to present the right information at the right time for a healthcare user to optimally monitor and engage in a particular patient to population event.

Figure 9B:
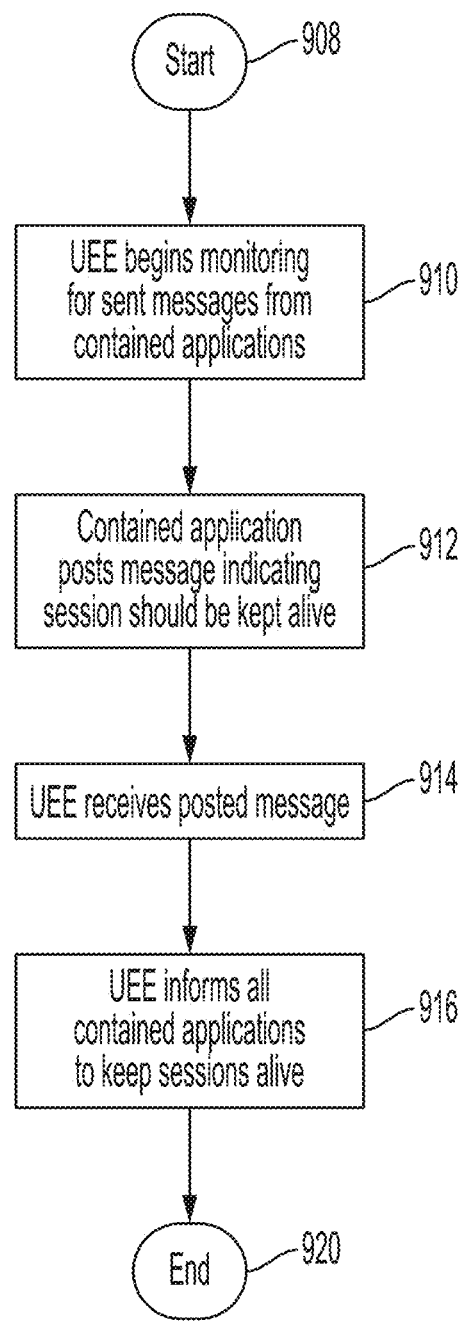
FIG. 9B depicts an exemplary process flow for managing messages and user sessions.

FIG. 9B illustrates a process flow demonstrating how the user interface manager application manages messages and prevents a signed-in (e.g., SSO) user from being logged out. As described above, a user is only able to engage in applications which are authorized in their SSO profile. After the start of the process flow at step 908, the UEE begins monitoring for sent messages from contained applications at step 910. At step 912, the contained application posts a message indicating that a session should be kept alive. At step 914, the user interface manager application receives the posted message. At step 916, the user interface manager application informs all contained applications to keep the session alive and the routine ends at step 920. Thus, due to the manner in which the user interface manager application utilizes the receiving and posting of messages, a user session is able to be kept alive. For example, an SSO global login session can be kept alive by each application either directly communicating (e.g., via API) with the SSO session or communicating with the user interface manager which in turn extends the SSO global login session. This allows a user to stay logged in to access the UEE.

Further, in the example of the occurrence of an ED event, an event may cause the applicable applications to snap to an updated contextual state to optimally present the event in a synchronized update to the applicable applications due to the occurrence of the event. While it is generally preferable for all applications to update to reflect the event, some applications may respond to the event, while others may not. Moreover, rather than a business (e.g., an ED event), the event can be driven by deep-linking commands delivered to iframes within the UEE to allow for i) application view synchronization and ii) application context changes for each contained application so that all the contained applications are directed to the respective patient record view and application screen leveraging iframe positioning and deep-linked URLs passed to each iframe. For example, when a first application is selected in one panel, it causes the system to automatically open a second application in an adjacent panel. The first and second applications can be applications from a common ecosystem of applications, or be from separate ecosystems, or individual applications or websites that are not part of any particular ecosystem. An example of different applications that still have a contextual link includes a first application that displays an ED alert within a care management record alongside an application that displays available service providers to support patient needs upon discharge to home. Clicking on a patient in one view can automatically display the optimal associated views and patient/population context mitigating the need for users to manually navigate each application that is displayed in the overall user interface. Moreover, opening one type of application may trigger the automatic opening of another (e.g., related) application.

Figure 9C:
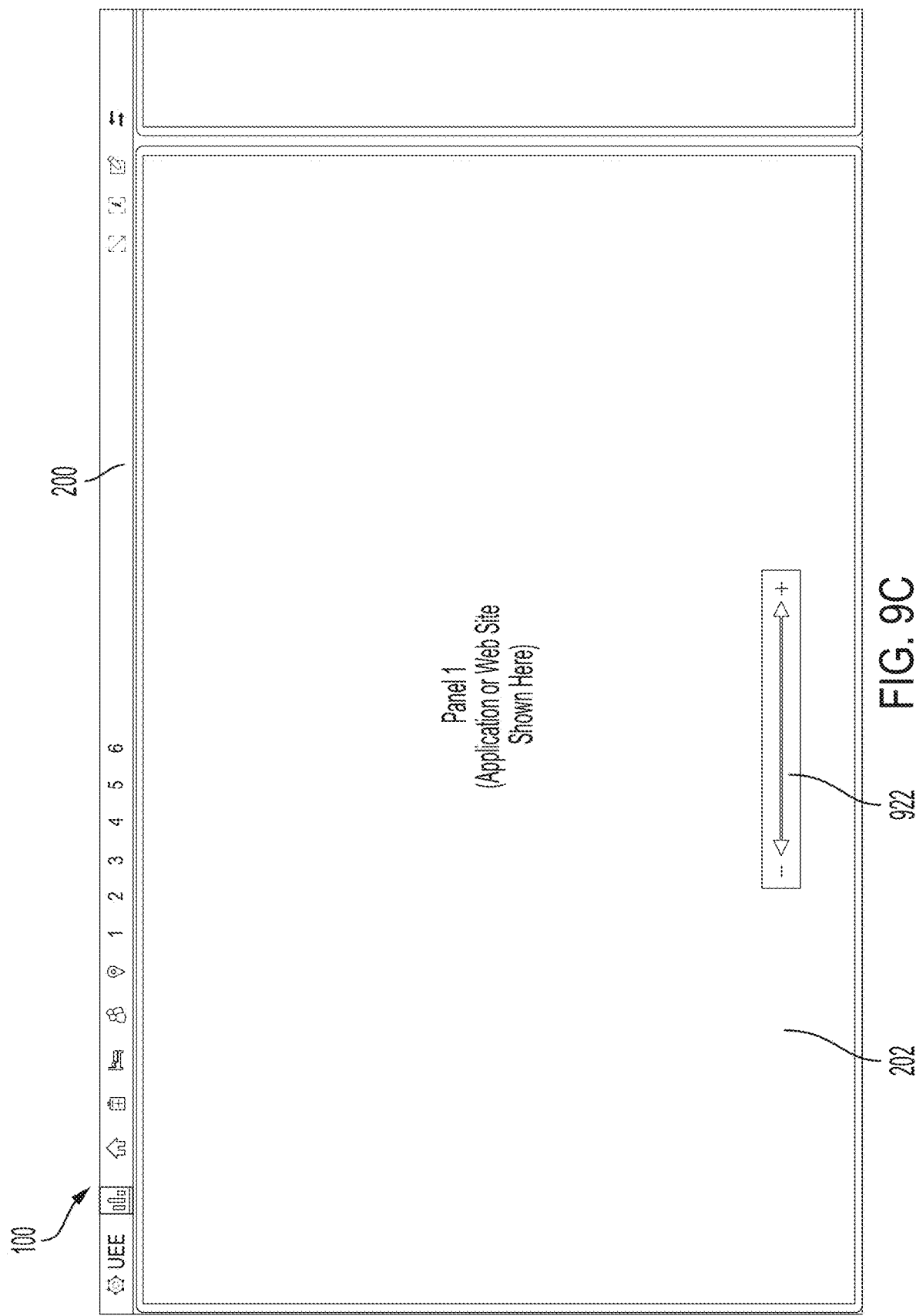
FIG. 9C depicts an illustration of a user-adjustable slider allowing for view adjustment in different applications/URLs.

As illustrated in FIG. 9C, the user interface of the user interface manager application 100 may comprise a user-adjustable slider 922 for adjusting to different view levels. For example, the slider 922 can be a population level selector allowing the user to span views from patient, panel, contract, system, and multiple systems levels to a full population level. While FIG. 9C shows slider 922 as being an object within panel 202, the slider could be designed to appear and/or be docked within others areas of the user interface manager application 100, such as in toolbar 200. When the user selects a desired population level, the UEE can send a message to each affected application to switch those applications to the level corresponding to the desired population.

Figure 21A:
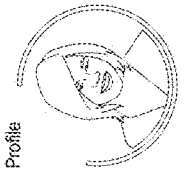
Figure 21B:
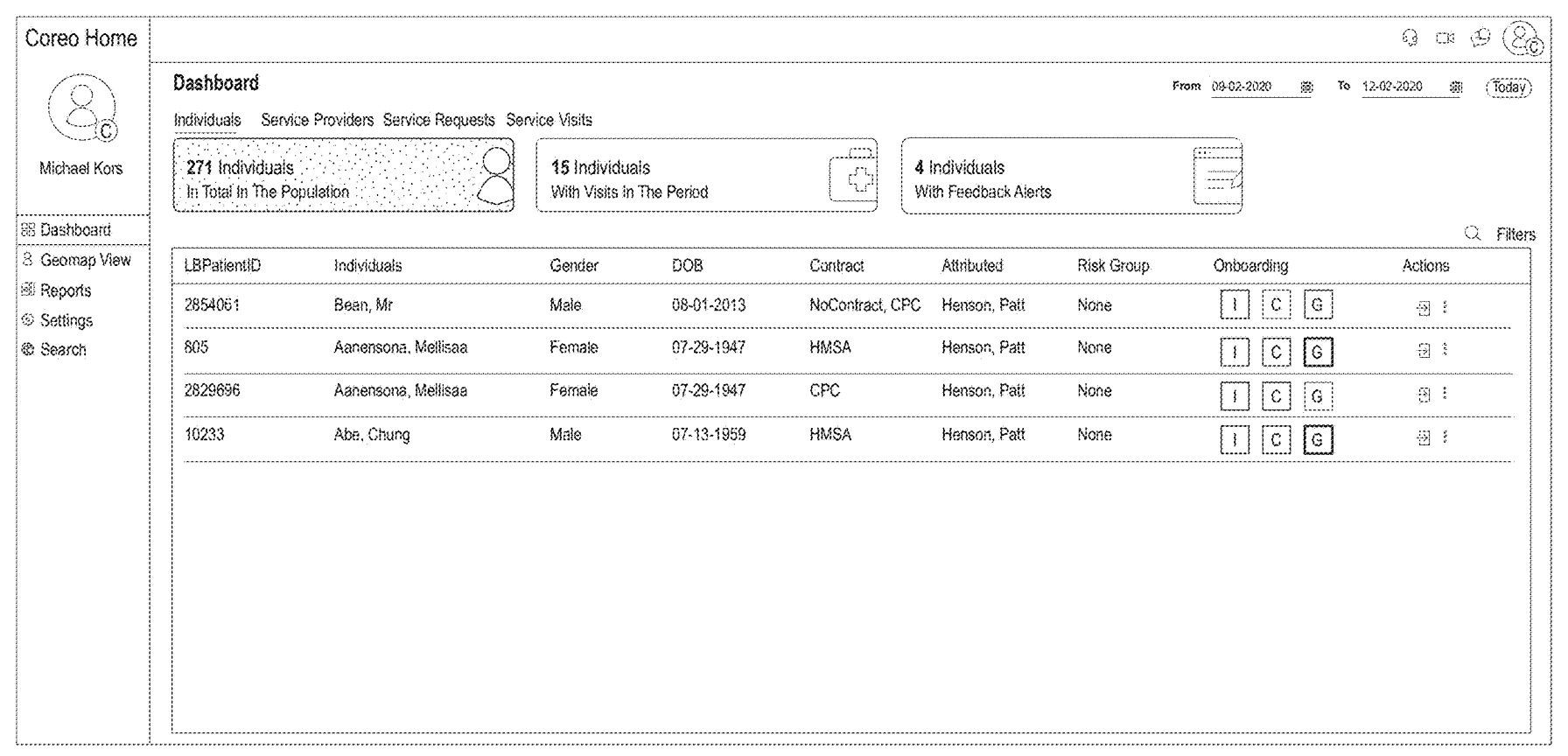
Figure 21C:
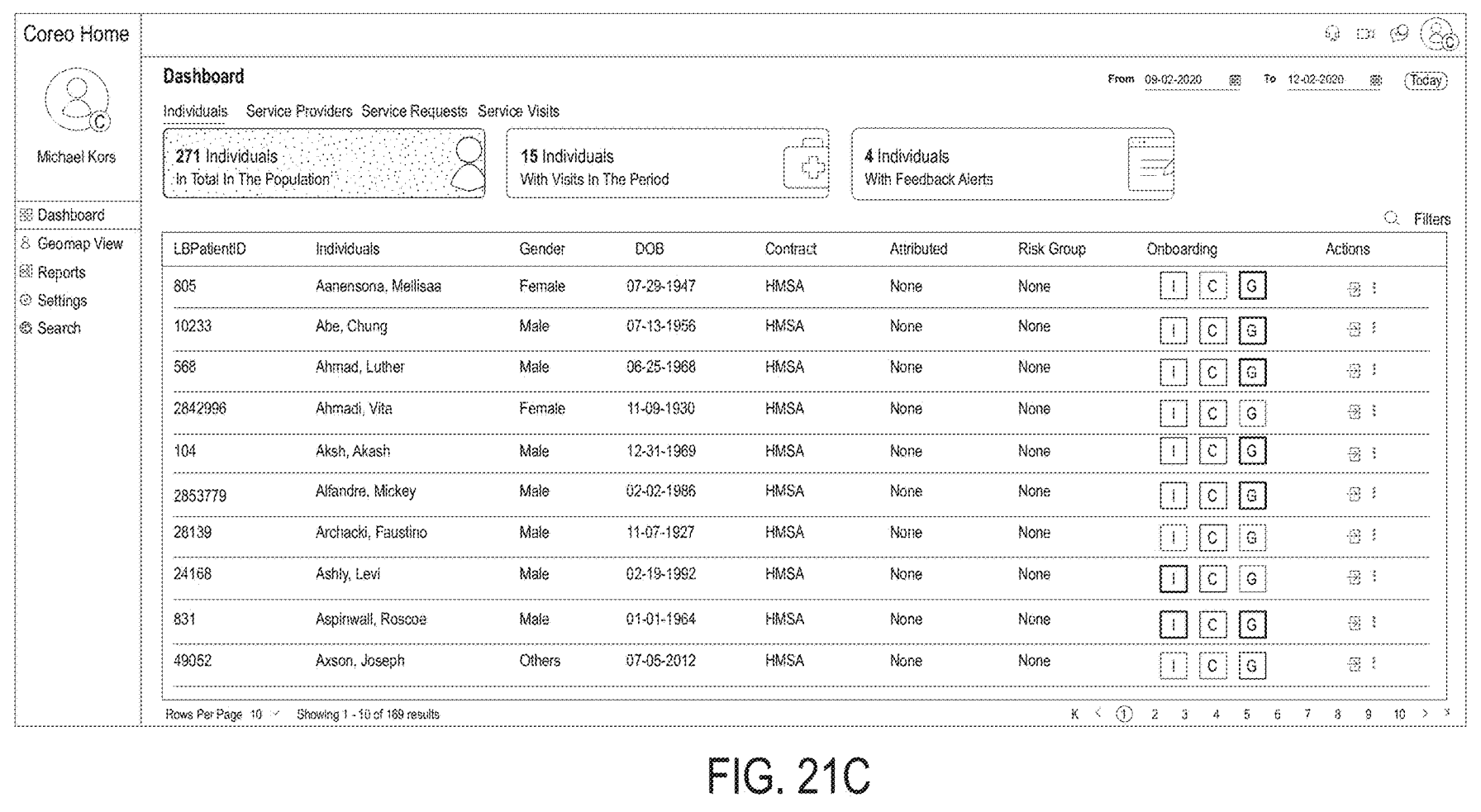

With respect to an example embodiment, at its lowest population level, the population level selector 922 can allow the user to view information via the UEE at an individual patient level. In this scenario, the system may ask the user to specify an individual patient to be covered. FIG. 21A shows an example screenshot of an application that displays information at the patient level. In this example, the COREO™ Home application can show profile data for a specific patient. At a next higher population level, the population level selector 922 can allow the user to view information via the UEE at a panel level. As an example, the panel can correspond to a primary care physician (PCP) practice and thus encompass a group of patients who are treated by a given PCP practice. In this scenario, the system may ask the user to specify the particular panel to be covered. FIG. 21B shows an example screenshot of an application that displays information at the panel level. In this example, the COREO™ Home application can show a dashboard that lists all of the patients that are attributed to a particular panel provider (Dr. Henson in this example). At a next higher population level, the population level selector 922 can allow the user to view information via the UEE at a contract level. As an example, the contract can correspond to Medicare and thus encompass a group of patients who are covered by Medicare and treated by various different practices. Other examples of contract types can include Medicare Share Savings Program (MSSP), Accountable Care Organization (ACO), and/or Commercial contracts. In this scenario, the system may ask the user to specify the particular contract to be covered. FIG. 21C shows an example screenshot of an application that displays information at the contract level. In this example, the COREO™ Home application can show a dashboard that lists all of the patients that are linked to a particular contract (HMSA in this example). At a next higher population level, the population level selector 922 can allow the user to view information via the UEE at a system level. As an example, the system can correspond to a health system or health plan and thus encompass a group of patients who are treated within a given health system or health plan. In this scenario, the system may ask the user to specify the particular system to be covered. FIG. 21D shows an example screenshot of an application that displays information at the system level. In this example, the COREO™ Home application can show a dashboard that lists all of the patients that are attributed to a particular health system. At the next higher population level (which would be the highest population level in this example), the population level selector 922 can allow the user to view information via the UEE at a multi-system/population-wide level. As an example, the system can correspond to multiple health systems or health plans and thus encompass a wide group of patients regardless of health system/health plan. In the context of a dashboard for the COREO™ Home application, the multi-system level view would be similar in nature to the system level of FIG. 21D, but with no constraints on health system so that the entire population of patients accessible to the user would be listed via the dashboard.

Further, beyond patient level displays there can be prioritized patient lists and/or aggregated patient data shown. The context of each application within the UEE can present the most relevant information varying automatically from the patient level to population level, thereby providing a user with the ability to optimally view small- and large-scale levels within the UEE. Selectable levels of display context for the management of population health can thus be achieved wherein each level displays segments of information such as clinical history and social determinants of health (SDOH), community and care team resources, among others. Additionally, certain applications may be associated with only one customer and other applications may be associated with one or more customers.

While FIG. 9C shows the use of a slider 922 as the population level selector, it should be understood that other mechanisms for capturing user input to define the population level could be employed. For example, user-selectable buttons could be provided for each population level. Moreover, the population level selector could be positioned on other parts of the GUI—for example, the population level selector could be positioned within the main toolbar 200.

Figure 10A:
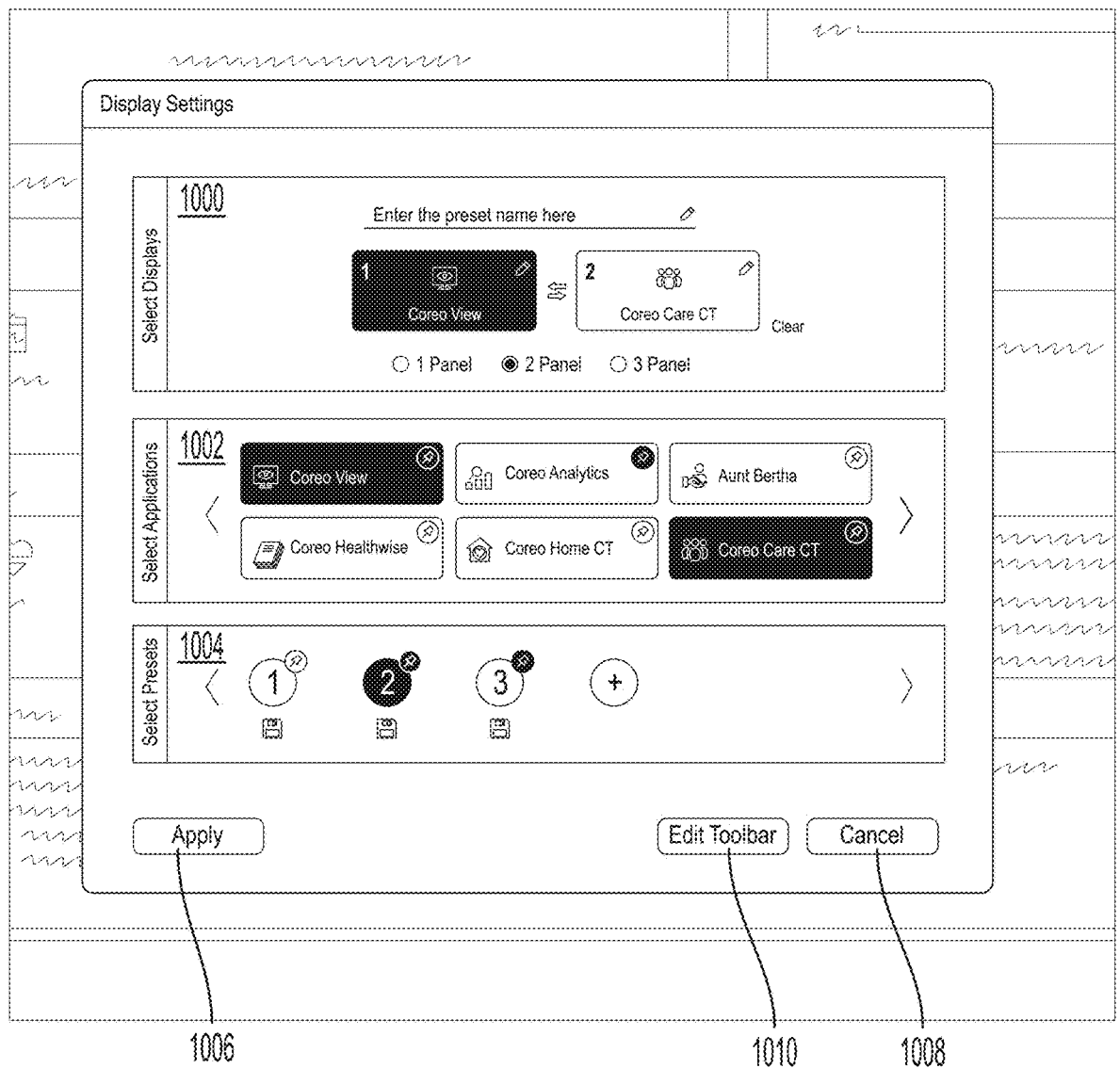
FIG. 10A illustrates user-defined settings for display of preferred applications and/or websites on a particular panel arrangement.

FIG. 10A illustrates an exemplary manner in which a user can define preferred display settings of the user interface manager application 100, such as preset panel configurations. At display settings section 1000, the user first selects a display format (e.g., single panel, two-panel, or three-panel), including a particular view (e.g., setting a first application to display in a first panel and a second application to display in a second panel in a two-panel setup). The user then selects, at section 1002, the desired applications from amongst a plurality of applications. These applications may be associated analytics data, patient data, among a wide array of other information. For example, the applications may be from one or more ecosystems of healthcare applications. After the user then selects, at 1004, the desired preset profile is saved based upon the above-noted selections. Operative buttons such as "Apply" button 1006 and "Cancel" button 1008 can be selected to effect or cancel any changes. There may also be additional buttons such as "Edit Toolbar" button 1010 to allow the user to further edit the user interface to their preferences. While a three-panel embodiment is shown as the maximum, this is definitely not a limiting factor since displaying more than three panels is envisioned whether horizontally positioned vertically and horizontalized position and/or less orderly positioned throughout enabling the precise placement of each application panel.

Figure 10B:
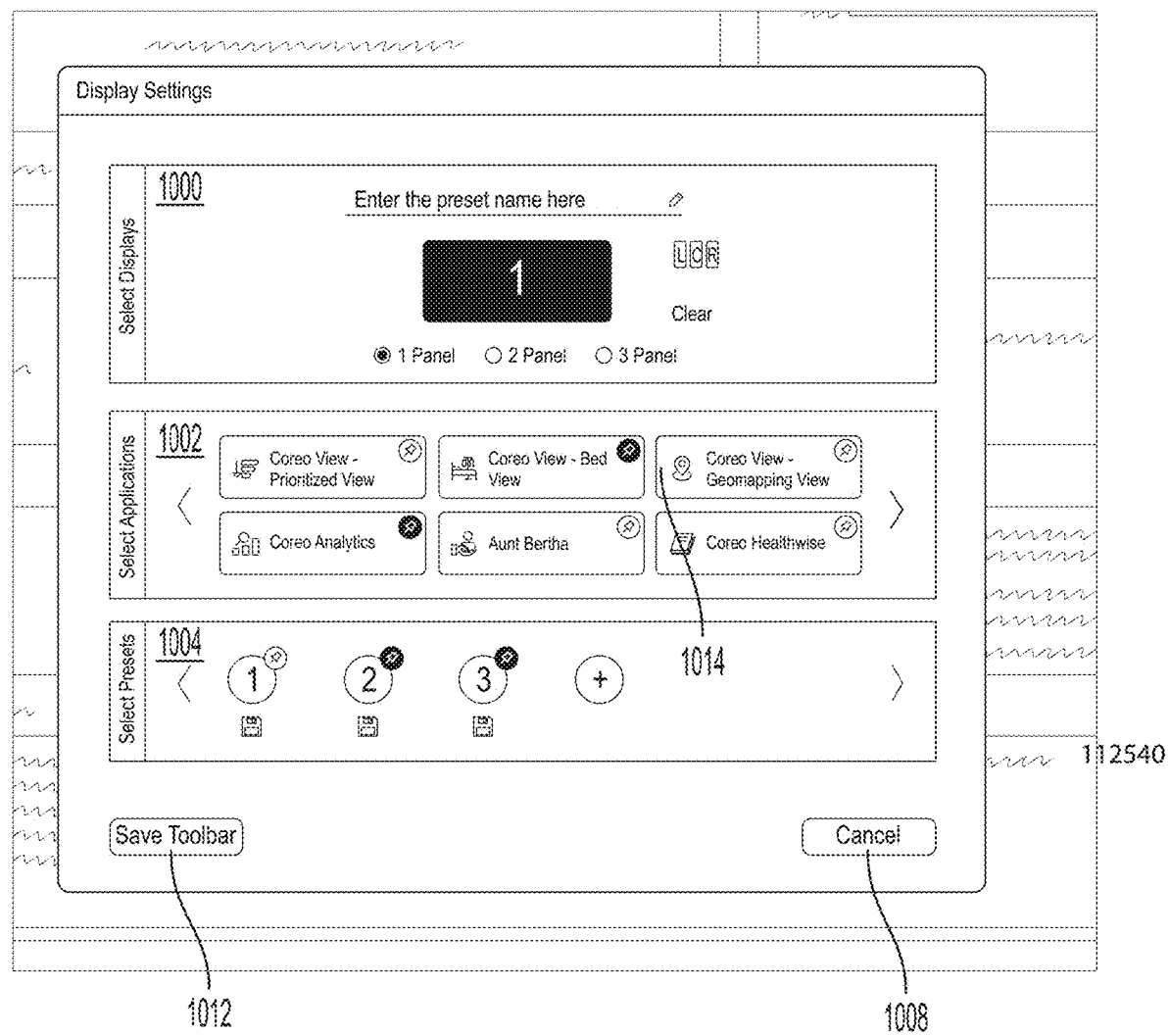
FIG. 10B illustrates storage of the user-defined settings according to FIG. 10A as a user preset.

FIG. 10B illustrates an example of the manner in which a user can save their desired settings for future use. As shown in FIG. 10B, the user has selected, at section 1000, a single panel arrangement and pinned two application buttons to the UEE toolbar, (e.g., an application 1 and an application 2) at section 1002. The user can, at section 1004, assign these display and application settings to a desired preset (e.g., preset slot 2) from amongst a plurality of preset slots and save the toolbar setting via the "Save Toolbar" button 1012, or cancel the settings via the "Cancel" button 1008. User selection of the pin feature associated with the respective applications (e.g., geo-mapping application 1014) and presets as shown in FIGS. 10A and 10B causes the pinned applications/presets to appear in the upper left of the main toolbar 200 as shown in FIGS. 2A to 2D for easy and convenient selection by the user. As such, the user is able to instantly switch the layout of applications using presets from the interface, thereby improving usability and efficiency within the unified look-and-feel of the user interface, representing a major improvement over the art. As described above, since the panels of the user interface manager application 100 are able to be used to display both applications and websites, the user is able to customize their desired presets to display an individualized combination of websites and/or applications.

While FIGS. 10A and 10B show an example user interface menu for defining panel layout presets, it should be understood that other techniques can be employed by the system to define panel layout presets. For example, the system can support "drag and drop" control over panel layouts where a user can drag desired applications and/or websites into desired panels to define an assignment of a particular panel of the multi-panel display with a particular application or website. Further still, the user can interact with the system via an input such as a right mouse click or the like to access a control instruction to identify a particular layout as a preset. Moreover, the system can support a user's ability to drag and draw a desired panel layout for placement of applications and/or websites. For example, user input could stretch or shrink panel borders to define a desired size for a given panel.

Figure 10C:
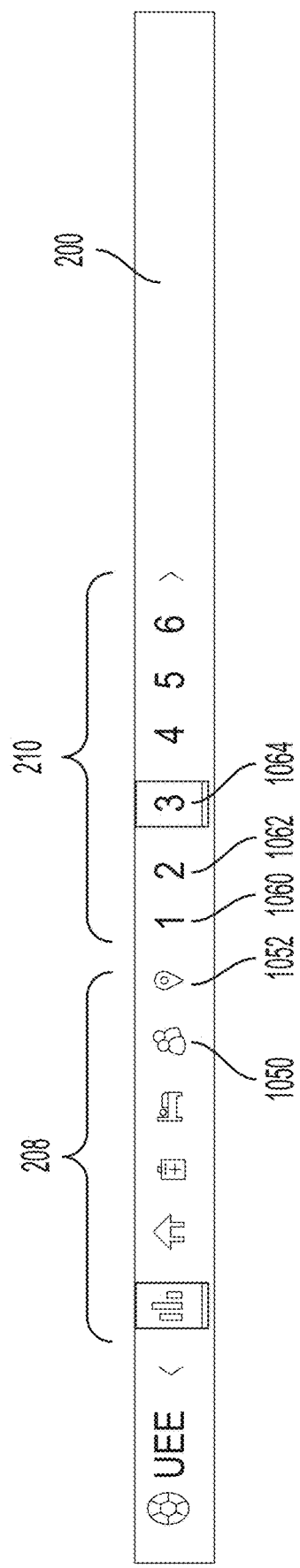
FIG. 10C illustrates a zoomed view of the toolbar of the user interface manager application according to FIG. 2A.
Figure 13A:
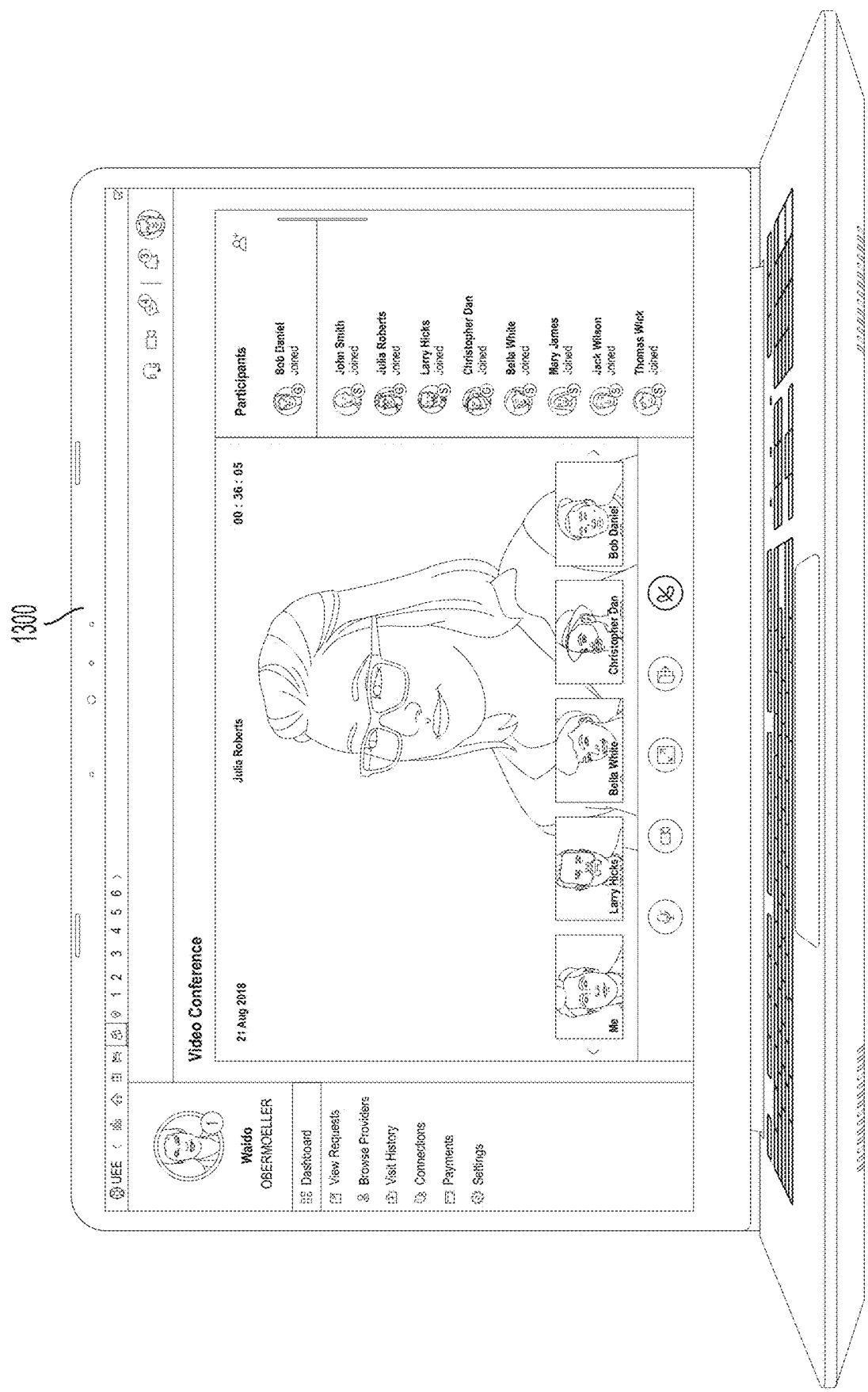
FIGS. 13A and 13B show examples of single panel preset views.
Figure 13B:
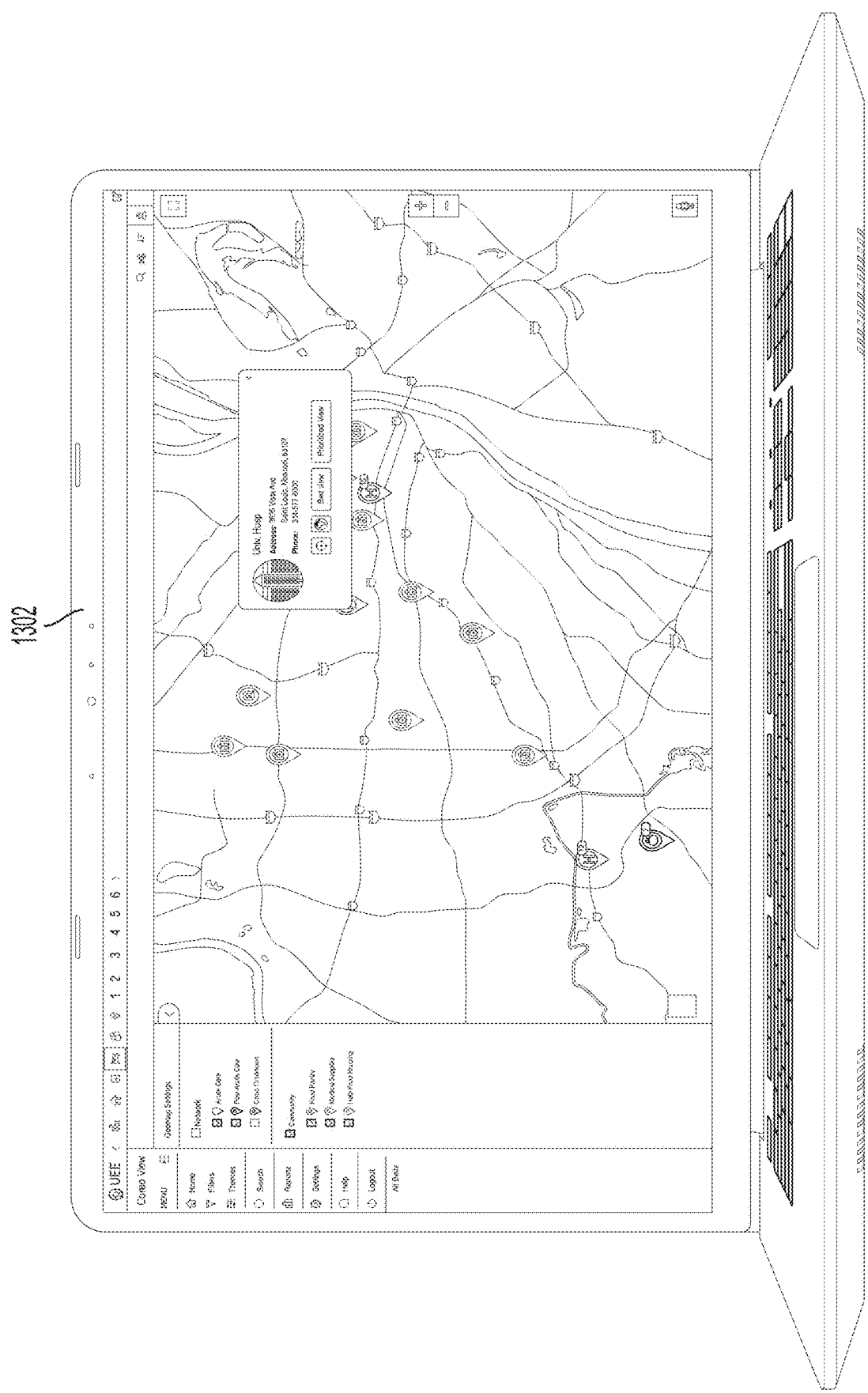

FIG. 10C illustrates a zoomed view of the left portion of main toolbar 200 of the user interface manager application (aka UEE), such as that shown in FIGS. 2A and 2B. Toolbar 200 shown by FIG. 10C includes a plurality of single panel preset buttons 208. The number of single panel preset buttons 208 that are included in the toolbar 200 can be user-configurable (for example, via the number of apps that are selected in connection with FIGS. 10A-10B discussed above). Each single panel preset button 208 corresponds to a particular application (or website) so that user selection of a given single panel preset button 208 will cause the display to switch to a single panel view through which the particular application (or website) corresponding to the selected button 208 is presented. For example, FIG. 2C shows an example view of a multi-panel layout where the first and second panels 202 and 204 show different applications. For the purpose of explanation, we can say that FIG. 10C shows a zoomed-in portion of the toolbar 200 of FIG. 2C. If the user selects single panel preset button 1050 shown by FIG. 10C (where single panel preset button 1050 is associated with Application X (say, a videoconferencing application)), then the view can switch to a single panel view 1300 where Application X is presented via the single panel (see FIG. 13A). Similarly, if the user selects single panel preset button 1052 shown by FIG. 10C (where single panel preset button 1052 is associated with Application Y (say, a map application)), then the view can switch to a single panel view 1302 where Application Y is presented via the single panel (see FIG. 13B). To facilitate the user's understanding of which single panel preset buttons 208 correspond to which applications, the graphics that are included in each single panel preset button 208 can be designed to indicate the corresponding application for that single panel preset button 208.

When the UEE is in a single panel mode (e.g., after one of the single panel presets has been selected), the UEE can maintain the standard aspect ratio of the application contained by the single panel. This can be the case even if the UEE width is greater than the application's standard width. In such a circumstances, the UEE can include space outside the single panel (e.g., see background spacing 222 shown by FIG. 2D). Furthermore, the single panel presets can accommodate a left-center-right configuration by a user that accommodates the position of the single panel so that the system avoids landing in a split between two monitors (if the user is employing multiple monitors). This makes the system flexible for accommodating different monitor formats (e.g. 2-monitor vs. 3-monitor setups, high resolution displays such as 4K monitors, etc.). FIG. 2D shows an example where a center configuration is employed on a single monitor layout. If a left configuration is employed on a 2-monitor or 3-monitor layout, then the single panel can be positioned in a leftmost position so that is occupies the leftmost part of the UEE (which would correspond to the leftmost-defined monitor). If a right configuration is employed on a 2-monitor or 3-monitor layout, then the single panel can be positioned in a rightmost position so that is occupies the rightmost part of the UEE (which would correspond to the rightmost-defined monitor). Similarly, in a 3-monitor layout, a center configuration can result in the single panel being positioned to occupy the center-defined monitor. In an example embodiment, the left-center-right configurations can be defined by a user via L-C-R buttons or the like that are included on a display settings control screen such as those shown by FIG. 10B. Furthermore, the displayed single panel can have one or more user-adjustable dimensions (such a user-adjustable width) that allows the user to change the panel dimension to achieve alignment with the display resolution of the monitor(s) which allows for perfect alignment within the edges of the monitor (such as with high resolution 4K monitors).

Figure 13C:
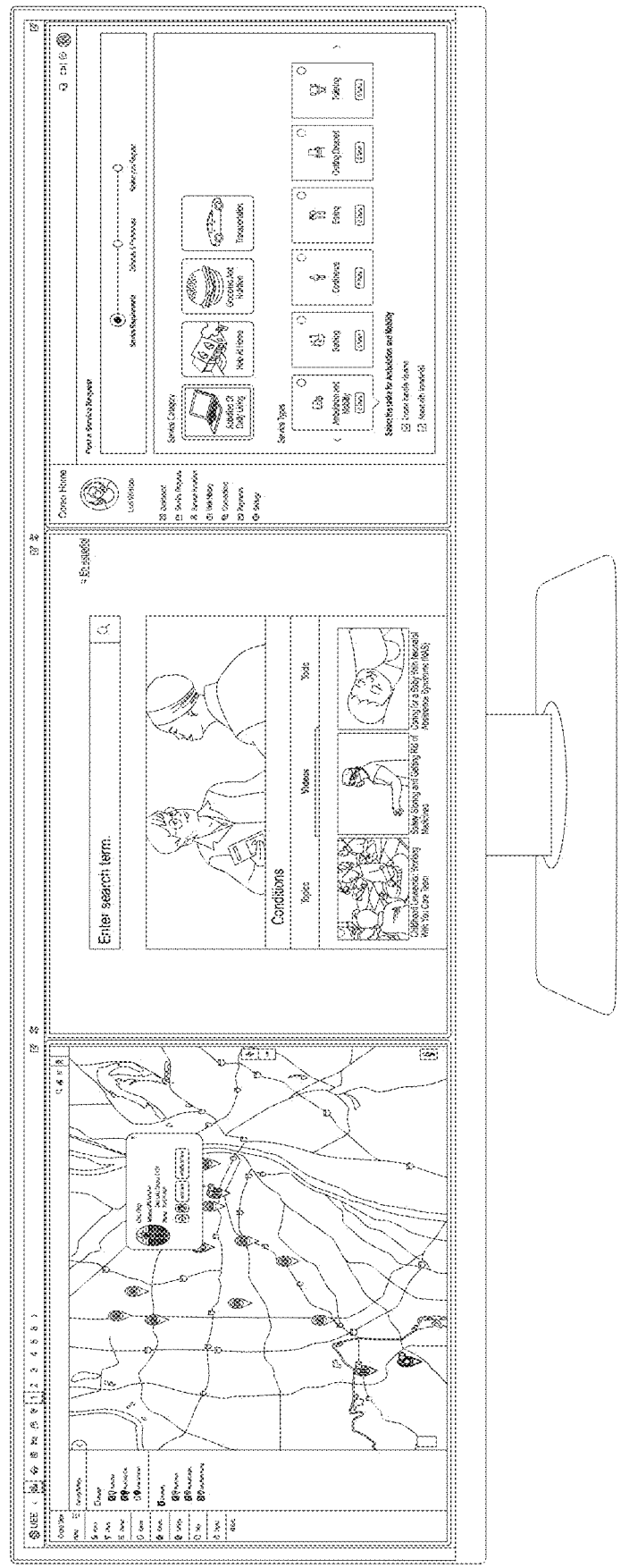
FIGS. 13C-13E show examples of multi-panel preset views.
Figure 13D:
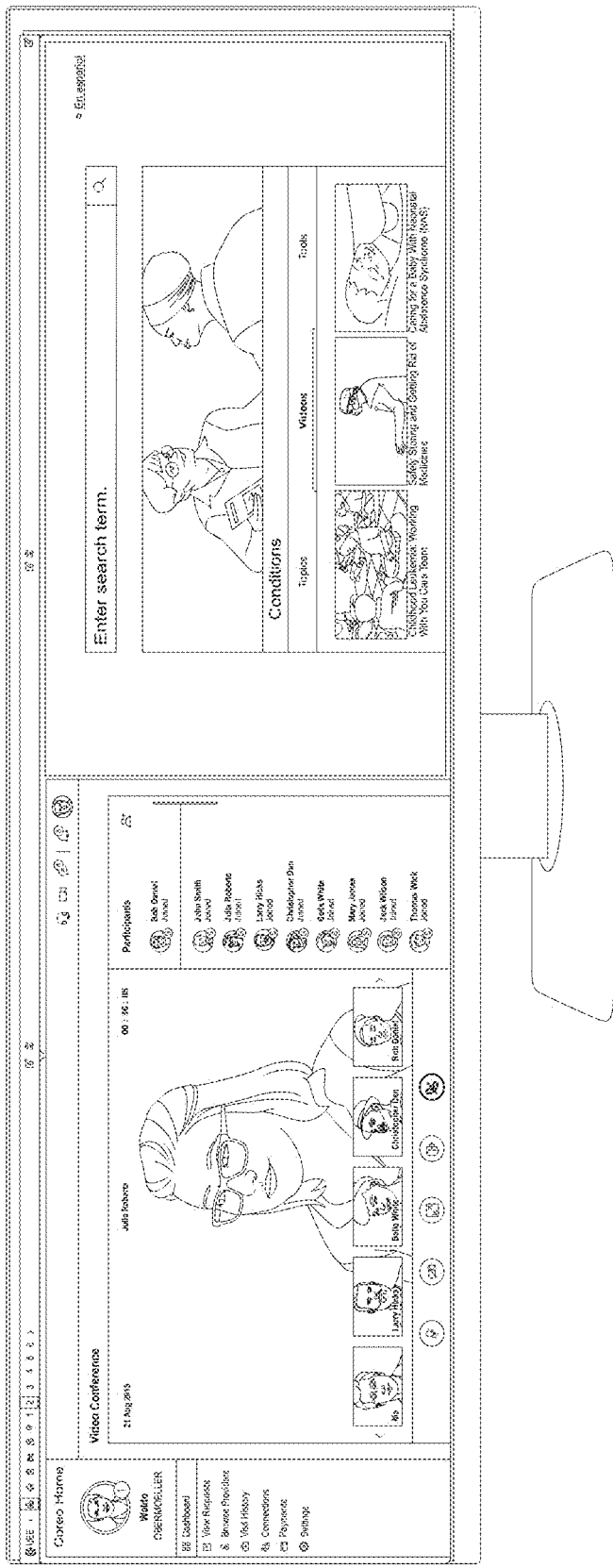
Figure 13E:
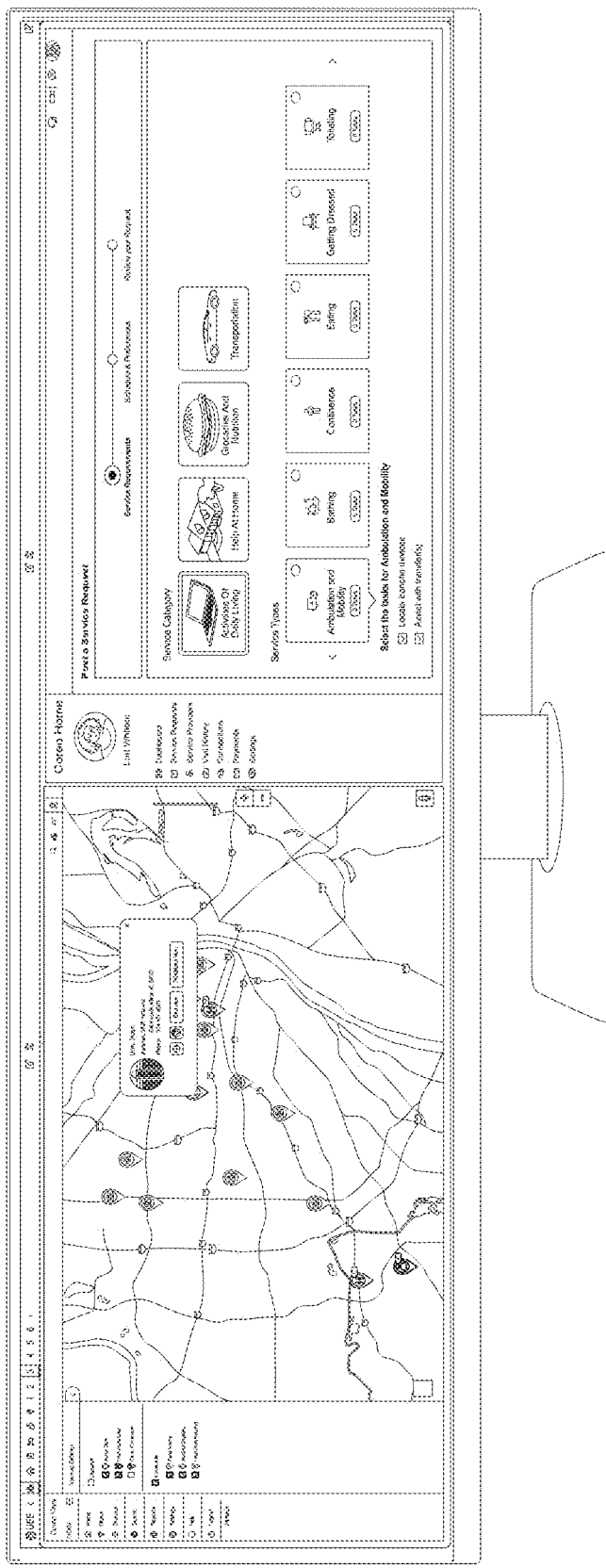

Toolbar 200 shown by FIG. 10C also includes a plurality of multi-panel preset buttons 210. The number of multi-panel preset buttons 210 that are included in the toolbar 200 can be user-configurable (for example, via the number of multi-panel presets that are created in connection with FIGS. 10A-10B discussed above). Each multi-panel preset button 210 corresponds to a particular grouping of applications across multiple panels so that user selection of a given multi-panel preset button 210 will cause the display to switch to a multi-panel view through which the various applications for that preset are presented in their corresponding panels. Continuing with the running example from above, where FIG. 10C shows a zoomed-in portion of the toolbar 200 of FIG. 2C, (1) multi-panel preset button 1060 shown by FIG. 10C is associated with a 3-panel view where Panel 1 shows a map application, Panel 2 shows a search application, and Panel 3 shows as home application), (2) multi-panel preset button 1062 shown by FIG. 10C is associated with a 2-panel view where Panel 1 shows a videoconferencing application and Panel 2 shows a search application, and (3) multi-panel preset button 1064 shown by FIG. 10C is associated with a 2-panel view where Panel 1 shows a mapping application and Panel 2 shows a home application. In response to user selection of multi-panel preset button 1060, the view can switch to that button's corresponding 3-panel view (see FIG. 13C). Similarly, in response to user selection of multi-panel preset buttons 1062 or 1064, the view can switch to that button's corresponding 2-panel view (see FIG. 13D if button 1062 is selected and FIG. 13E if button 1064 is selected).

The groupings of single panel preset buttons 208 and multi-panel preset buttons 210 in toolbar 200 serve as a significant and meaningful technical innovation in the art because they provide users with efficient access to multiple applications and views through the UEE while retaining the ability to efficiently navigate to different applications and views. Relative to conventional solutions in the art, there is no need to navigate to different applications or views by manually switching to different browsers or browser tabs. Instead, the toolbar 200 (which can remain in position above the panel(s) as the user interacts with the system) provides users with direct access to a desired view through selection of an appropriate single panel preset button 208 or multi-panel preset button 210.

Figure 11:
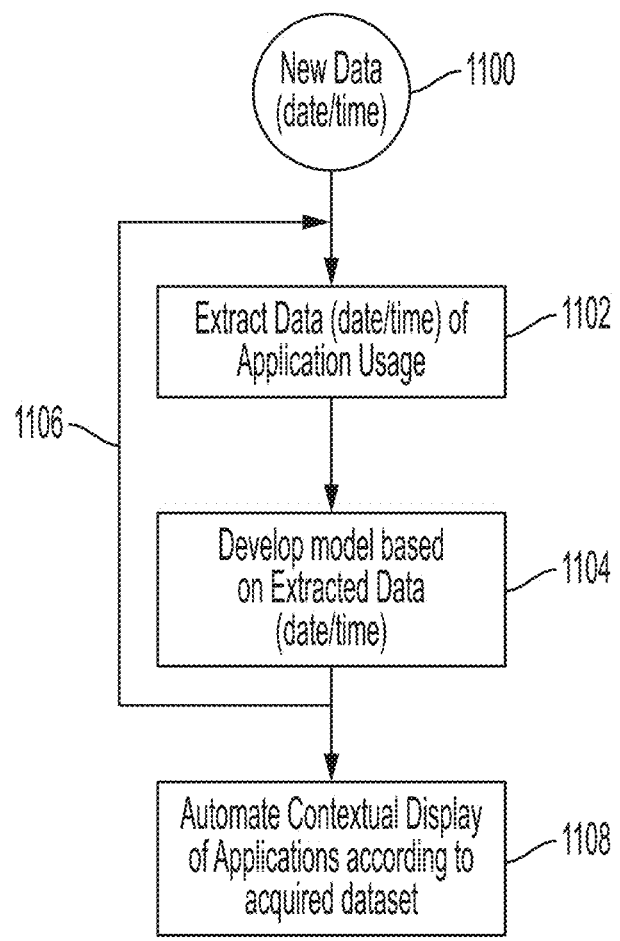
FIG. 11 illustrates an embodiment of the user interface manager application that utilizes artificial intelligence and/or machine learning for adjusting context.

FIG. 11 illustrates a process flow for how artificial intelligence (AI) and/or machine learning (ML) can be leveraged to learn a user's preferences (e.g., workflow preferences) and automatically adapt the UEE to apply such preferences accordingly, based on various triggers such as date, time, events and a user's habits over a particular time period, among others. At step 1100, new data is entered into a dataset of an algorithm/model for learning a user's patterns, such the context of the displayed applications at the time of an event or at a certain date/time. This new data may be used as a trigger to cause an automatic update/change to occur. For example, a particular time may serve as a trigger that causes an application to refresh or otherwise update and/or change content at the particular time. At step 1102, the data is extracted and added to the dataset of the algorithm/model.

At step 1104, the algorithm/model is refined/further developed. Prior to implementation of the model in the user interface manager application, the model can be trained to develop the model as desired. The refinement of the algorithm/model can be repeated over and over to further develop the algorithm/model, as illustrated by the return loop 1106 that jumps back to just before step 1102. At step 1108, automation of the user interface manager application 100 can be achieved by way of the algorithm/model generating an output that can be received by the user interface manager application for automating the contextual display of applications within the user interface manager application based on the learned behaviors of the user. Thus, contextual changes as described above in other embodiments can be realized on the basis of user behavior that is learned over time via AI/ML techniques incorporated into the user interface manager application. For example, using the above-described AI/ML techniques, clicking within one panel such as a particular feature of the application within the panel could automatically cause the layout of other adjacent applications within the UEE to adapt to optimally display the right information at the right time. Such a trigger action can be based upon patient selection (e.g., view synchronization), feature selection (e.g., choosing an ED visit summary in one application displays a particular layout of applications and associated screens within each corresponding adjacent application for monitoring and engaging in the associated workflow), or other selections. Thus, AI and/or ML can be used to facilitate learning and/or implementing based upon these triggers (e.g., the new data at 1100). An AI/ML model of the present application as described above is thus built (e.g., at step 1104) based on learned user behavior data gathered, by way of supervised learning techniques, unsupervised learning techniques, and/or reinforcement learning techniques. In supervised learning, an input is provided and the task is to predict the correct output. In unsupervised learning, the task is to discover the structure of the data by grouping similar items to form clusters for example. In reinforcement learning, feedback about good or bad choices in a particular context/environment is used to develop the AI/ML. The model algorithm may be designed so as to be particularly tuned to the above-noted triggers (e.g., event, date, time of application access, duration of use, etc.) such that an output from the algorithm can cause the contextual updates within the applications of the user interface manager application. This can lead to automation of the layout of the applications and panels of the user interface based upon various triggers (e.g., ranging from a single patient event such as an ED alert to geo-fencing being crossed by a patient arriving at a healthcare facility such as a primary care provider (PCP) office), and expanded to a population wide AI/ML driven scenario identified (e.g., significant increase in ED visits or purchasing of a particular drug trending higher than expected across populations). Such automation can further be used to trigger certain application layouts to be displayed in the UEE with specific areas within each application recalled based upon the source trigger to optimally review, monitor and act upon the event and AI/ML identified situation. Moreover, the solution can be leveraged to trigger situations outside the boundaries of the norm thereby resulting in solutions that may have otherwise been missed by human operators. The solution can learn prevalent user workflow layouts that can be instantly recalled improving efficiency and effectiveness of healthcare users representing a significant improvement over conventional workflows. While the new data at 1100 in FIG. 11 is shown in the context of being used in conjunction with an AI/ML embodiment, the use of triggers is also envisioned outside of an AI/ML embodiment. For example, a particular time may trigger a certain event regardless of if that time is used as part of an AI/ML scheme.

FIG. 12 illustrates certain applications being capable of providing both a single-customer and/or multi-customer experience (e.g., a customer mode 1200). Customers may have different applications and isolated data that must be accessed by a centralized team. Single- and multi-customer applications may be displayed side-by-side, minimizing the inefficiencies of context switching and avoiding confusion of switching applications and/or URL tabs. For example, in FIG. 12, panel 202 may display a first customer application (Customer Application 1) and panel 204 may display a second customer application (Customer Application 2). The customer(s) associated with Customer Application 1 and Customer Application 2 may be different, or may be the same. Moreover, Customer Application 1 may be configured to only display information pertaining to one customer, while Customer Application 2 may be configured to display information pertaining to multiple customers, and vice versa. Customer Application 1 and Customer Application 2 can alternatively each be configured to display information pertaining to multiple customers.

Additional aspects of the present user interface manager application are as follows. The operation of the mouse cursor may be aligned with the ease and simplicity of the overall user interface manager application. The mouse cursor may be configured such that merely hovering of the cursor over an intended clickable object automatically causes the panel containing that clickable object to become the active panel. Therefore, no click is required to take control of any given window and/or to grab context between windows. The user does not need to actively click to make a particular panel the active panel. Rather, merely traversing the cursor through the panels of the user interface manager application triggers activation of the panels with respect to the position of the cursor. The user interface manager application can be programmed to provide for such mouse cursor functionality to further increase the usability and efficiency benefiting the user experience by reducing errors and sparing the user from having to waste time and effort clicking the mouse to activate an intended clickable object within an application panel. The user is able to navigate through the various loaded applications and/or websites seamlessly with extreme ease matching the ease of operation of the overall user interface manager application.

The user interface manager application may be configured to provide real-time, remote collaboration. For example, a user can share a real-time experience using the user interface manager application among two or more participants to facilitate collaboration from across the room or across the world (e.g., sharing the experience of the user interface manger application as opposed to merely sharing the screen). This can further be combined with live, multi-party video conferencing for face-to-face collaboration and would allow for warm hand-offs of an initiator/team leader to step out while the remainder of the team engages to complete the workflow.

In addition to the above-noted mechanisms for triggering contextual UEE based workflows, a telephony-driven trigger is also envisioned. A telephony-driven trigger allows for automatic display of optimal applications and/or URLs and specific content based upon inbound/outbound calling. As such, the area code and/or phone number itself may serve as a trigger to automatically adjust the applications and associated information being displayed by the user interface manager application. Further triggering mechanisms for producing a contextual response throughout various applications and/or websites is also envisioned.

As described above, the user interface manager application (also known as the application layout and synchronization manager) of the present application provides a cohesive, seamless GUI that displays contextually cross-linked applications as a plurality of panels within a common window. Due to the unified design of the user interface manager application, space does not need to be consumed by elements that are not beneficial to clinical workflows (e.g., URLs, browser tabs, etc.). Due to the underlying contextual linkage between applications contained within the user interface manager application, there is support for both ecosystem and non-ecosystem customer applications (e.g. customer EMR applications) displayed side-by-side allowing experience unification to extend beyond a single ecosystem. These nonconventional techniques represent a drastic improvement over conventional user interfaces in the healthcare field.

Although the user interface manager application is primarily envisioned for usage in the healthcare industry, the user interface manager application can be used in various industries, such as those where screen real estate is at a premium and/or contextually-linked information is of importance. For example, the user interface manager application has applicability in industries such as stock trading, graphic design, industrial control, and so on and so forth. The user interface manager application represents a drastic improvement over conventional user interfaces in general outside of the healthcare industry. The processes and techniques described herein are non-conventional and the method of applying the combination of elements to fulfill the embodiment of this solution is not well-known techniques regardless of what industry they are used in.

In the present disclosure, all or part of the units or devices of any system and/or apparatus, and/or all or part of functional blocks in any block diagrams may be executed by one or more electronic circuitries including a semiconductor device, a semiconductor integrated circuit (IC) (e.g., such as a processor), or a large-scale integration (LSI). The LSI or IC may be integrated into one chip and may be constituted through combination of two or more chips. For example, the functional blocks other than a storage element may be integrated into one chip. The integrated circuitry that is called LSI or IC in the present disclosure is also called differently depending on the degree of integrations, and may be called a system LSI, VLSI (very large-scale integration), or ULSI (ultra large-scale integration). For an identical purpose, it is possible to use an FPGA (field programmable gate array) that is programmed after manufacture of the LSI, or a reconfigurable logic device that allows for reconfiguration of connections inside the LSI or setup of circuitry blocks inside the LSI. Furthermore, part or all of the functions or operations of units, devices or parts or all of devices can be executed by software processing (e.g., coding, algorithms, etc.). In this case, the software is recorded in a non-transitory computer-readable recording medium, such as one or more ROMs, RAMs, optical disks, hard disk drives, solid-state memory, and so on and so forth, having stored thereon executable instructions which can be executed to carry out the desired processing functions and/or circuit operations. For example, when the software is executed by a processor, the software causes the processor and/or a peripheral device to execute a specific function within the software. The system/method/device of the present disclosure may include (i) one or more non-transitory computer-readable recording mediums that store the software, (ii) one or more processors (e.g., for executing the software or for providing other functionality), and (iii) a necessary hardware device (e.g., a hardware interface).

In view of the foregoing, it will be seen that the several advantages of the invention are achieved and attained. The embodiments were chosen and described in order to best explain the principles of the disclosure and their practical application to thereby enable others skilled in the art to best utilize the various embodiments and with various modifications as are suited to the particular use contemplated. As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

It should also be understood that when introducing elements of the present invention in the claims or in the above description of exemplary embodiments of the invention, the terms "comprising," "including," and "having" are intended to be open ended and mean that there may be additional elements other than the listed elements. Additionally, the term "portion" should be construed as meaning some or all of the item or element that it qualifies. Moreover, use of identifiers such as first, second, and third should not be construed in a manner imposing any relative position or time sequence between limitations.

What is claimed is:

1. A system for a unified experience exercising integrated viewing and control over a plurality of different computer applications and/or websites, the system comprising:
  a processor; and
  a memory configured to store a plurality of software instructions that define a user interface manager application;
  wherein the processor is configured to (1) communicate over a network with a plurality of different computer applications and/or websites and (2) execute the user interface manager application to present a unified user interface experience that permits a user to view and interact with the different computer applications and/or websites that are combined via the software instructions for display through different portions of a user interface; and
  wherein the user interface manager application is configured for execution by the processor to cause the processor to:
    create a plurality of different user interface layouts selectable by the user for display on a screen, wherein each user interface layout comprises at least one panel, and wherein each of a plurality of the user interface layouts comprises a plurality of panels; and
    manage a plurality of frame data structures to control which of the computer applications and/or websites are presented to the user through the panels of the user interface layouts, wherein each frame data structure is (1) associated with a corresponding computer application or website and (2) assignable via the user interface manager application to the panels of the user interface layouts, and wherein the frame data structures are concurrently persisting within the memory to retain states for their corresponding computer applications and/or websites even if their corresponding computer applications and/or websites are not presented through a currently displayed user interface layout; and wherein each panel of the currently displayed user interface layout is configured to (1) present data from the computer application or website associated with a frame data structure assigned to that panel and (2) receive user input for delivery to the computer application or website associated with the frame data structure assigned to that panel.

2. The system of claim 1 wherein the user interface manager application is configured as an application layout and synchronization manager.

3. The system of claim 1 wherein the computer applications comprise a plurality of healthcare applications.

4. The system of claim 1 wherein the computer applications include an Electronic Medical Record (EMR) application, a care management application, a healthcare visualization application, a patient engagement application, and a remote patient monitoring application, and wherein different panels of the user interface layouts are configured to present the EMR application, the care management application, the healthcare visualization application, the patient engagement application, and the remote patient monitoring application.

5. The system of claim 1 wherein the user interface manager application is further configured for execution by the processor to cause the processor to:
   assign the concurrently persisting frame data structures to the panels to associate the panels with corresponding computer applications and/or websites; and
   switch between different ones of the user interface layouts for current display on the screen in response to user inputs through the panels or a toolbar so that different ones of the displayed user interface layouts present different combinations of the computer applications and/or websites through their panels.

6. The system of claim 1 wherein each concurrently persisting frame data structure identifies an address for its associated computer application or website.

7. The system of claim 1 wherein each concurrently persisting frame data structure has a display status of visible or hidden, and wherein the user interface manager application is further configured for execution by the processor to cause the processor to:
   controllably switch the concurrently persisting frame data structures between the visible status and the hidden status based on which of the user interface layouts is currently presented on the screen so that (1) each concurrently persisting frame data structure associated with a computer application or website and assigned to a panel of the currently presented user interface layout has the visible status while the other concurrently persisting frame data structures have the hidden status and (2) the currently presented user interface layout displays the retained state of each computer application and/or website corresponding to each concurrently persisting frame data structure with the visible status.

8. The system of claim 1 wherein the created user interface layouts include a plurality of single panel user interface layouts for a plurality of single panel presets, wherein each single panel user interface layout comprises a single panel that is associated with a different computer application or website for presentation to the user, and wherein the user interface manager application is further configured for execution by the processor to cause the processor to:
   include a plurality of single panel preset buttons in a user interface toolbar, each single panel preset button corresponding to a different one of the single panel user interface layouts and being selectable by the user to switch the system to display the single panel user interface layout corresponding to the selected single panel preset button on the screen.

9. The system of claim 8 wherein the user interface toolbar includes a user-configurable number of the single panel preset buttons.

10. The system of claim 8 wherein the user interface manager application is further configured for execution by the processor to cause the processor to:
    create the single panel presets by selecting the computer applications and/or website to be associated with the single panel presets from a menu of available computer applications and/or websites in response to user input.

11. The system of claim 8 wherein the created user interface layouts further include a plurality of multi-panel user interface layouts for a plurality of multi-panel presets, wherein each multi-panel user interface layout comprises a plurality of panels where each panel is associated with a different computer application or website for presentation to the user, and wherein the user interface manager application is further configured for execution by the processor to cause the processor to:
    include a plurality of multi-panel preset buttons in the user interface toolbar, each multi-panel preset button corresponding to a different one of the multi-panel user interface layouts and being selectable by the user to switch the system to display the multi-panel user interface layout corresponding to the selected multi-panel preset button on the screen.

12. The system of claim 11 wherein the user interface toolbar includes a user-configurable number of the multi-panel preset buttons.

13. The system of claim 11 wherein the user interface manager application is further configured for execution by the processor to cause the processor to:
    create the multi-panel presets by (1) selecting how many panels to include in each multi-panel user interface layout in response to user input and (2) selecting the computer applications and/or websites to be associated with the panels of the multi-panel presets from a menu of available computer applications and/or websites in response to receive user input.

14. The system of claim 11 wherein the currently displayed user interface layout comprises a multi-panel user interface layout that includes a toolbar in a top portion of the multi-panel user interface layout that spans a plurality of the panels of the currently displayed user interface layout, and wherein the toolbar includes the single panel preset buttons and the multi-panel preset buttons.

15. The system of claim 1 wherein the user interface manager application is further configured for execution by the processor to cause the processor to:
    detect data indicative of a screen dimension for the screen, and auto-adapt the user interface for presentation on the screen based on the detected screen data.

16. The system of claim 15 wherein the detected data comprises a screen dimension corresponding to a screen type from among at least a mobile device screen, a computer monitor screen, and a multi-monitor screen.

17. The system of claim 15 wherein the auto-adaptation controls a size and format of the one or more panels within the user interface.

18. The system of claim 15 wherein the screen comprises a plurality of screens in a multi-monitor arrangement.

19. The system of claim 15 wherein the user interface manager application is further configured for execution by the processor to cause the processor to:
provide a virtual endless scroll capability for a multi-panel user interface layout that is displayed on a screen whose screen size is not sufficiently wide to accommodate a view of all panels of the multi-panel user interface layout.

20. The system of claim 1 wherein the user interface manager application is further configured for execution by the processor to cause the processor to:
present a selection interface through which the user creates a preset user interface layout, wherein the selection interface is configured to (1) prompt the user for input to define a number of panels to include in the preset user interface layout, (2) provide the user with a menu of available computer applications and/or websites for association with each panel of the preset user interface layout, and (3) receive input from the user corresponding to a selection of a computer application or website from the menu to associate with each panel of the preset user interface layout; and
create a preset user interface layout for inclusion among the user interface layouts in response to user inputs via the selection interface.

21. The system of claim 20 wherein the user interface manager application is further configured for execution by the processor to cause the processor to:
create a plurality of preset user interface layouts for inclusion among the user interface layouts in response to user inputs via the selection interface, wherein the preset user interface layouts include a plurality of single panel preset user interface layouts and a plurality of multi-panel preset user interface layouts; and
include selectable buttons for accessing the single panel preset user interface layouts and the multi-panel preset user interface layouts on a toolbar of the currently displayed user interface layout.

22. The system of claim 20 wherein the user interface manager application is further configured for execution by the processor to cause the processor to:
control access, by the user, to the different computer applications and/or websites by a single sign on (SSO) control scheme associated with the user.

23. The system of claim 22 wherein the SSO control scheme limits the different computer applications and/or websites to computer applications and/or websites that the user is authorized to use.

24. The system of claim 1 wherein each of a plurality of the user interface layouts includes panels that have predefined associations with computer applications and/or websites that are to be presented in those panels, wherein the predefined associations are defined in the memory by the software instructions.

25. The system of claim 1 wherein the user interface manager application is further configured for execution by the processor to cause the processor to create an initial user interface display for presentation to the user in response to a start of the user interface manager application for the user by:
determining the user;
identifying a plurality of computer applications that are available to the determined user, wherein a plurality of the concurrently persisting frame data structures are associated with the identified computer applications;
selecting a multi-panel user interface layout from among the user interface layouts;
populating the selected multi-panel user interface layout by assigning the concurrently persisting frame data structures that are associated with a plurality of the identified computer applications to the panels of the selected multi-panel user interface layout; and
providing the selected and populated multi-panel user interface layout as the initial user interface display for presentation to the determined user on the screen.

26. The system of claim 25 wherein the selected multi-panel user interface layout is a preset multi-panel user interface layout for the determined user.

27. The system of claim 25 wherein the selected multi-panel user interface layout is a default multi-panel user interface layout.

28. The system of claim 1 wherein the user interface manager application is further configured for execution by the processor to cause the processor to:
define a parent browsing context corresponding to the currently displayed user interface layout, and wherein each concurrently persisting frame data structure serves as an embedded browsing context within the defined parent browsing context and has its own session history so that the user interface manager application retains states for the computer applications and/or websites associated with the concurrently persisting frame data structures even if not currently displayed.

29. The system of claim 28 wherein the user interface manager application is further configured for execution by the processor to cause the processor to:
handle a document object model (DOM) that manages the concurrently persisting frame data structures.

30. The system of claim 1 wherein the user interface manager application is further configured for execution by the processor to cause the processor to:
switch between displays of the different user interface layouts by changing which of the concurrently persisting frame data structures are visible through the panels without requiring a reload of the computer applications and/or websites.

31. The system of claim 30 wherein the computer applications are swapped in and out of the displayed user interface layouts through control over which of the concurrently persisting frame data structures have a visible status versus a hidden status, and wherein the retained state results in a computer application corresponding to a concurrently persisting frame data structure that changes from the hidden status to the visible status to be displayed via the currently displayed user interface layout with the same information it was displaying prior to be swapped out.

32. The system of claim 1 wherein the user interface layouts comprise a first user interface layout and a second user interface layout;
wherein the first user interface layout comprises two panels for presenting a care management application and a healthcare visualization application to the user; and
wherein the second user interface layout comprises two panels for presenting an EMR application and a remote patient monitoring application to the user.

33. The system of claim 1 wherein the user interface layouts comprise a first user interface layout and a second user interface layout;
wherein the first user interface layout comprises three panels for presenting an EMR application, a care management application, and a healthcare visualization application to the user; and wherein the second user interface layout comprises two panels for presenting a patient engagement application and a remote patient monitoring application to the user.

34. The system of claim 1 wherein the user interface layouts comprise a first user interface layout and a second user interface layout;

wherein the first user interface layout comprises three panels for presenting a care management application, a healthcare visualization application, and a patient engagement application to the user; and wherein the second user interface layout comprises a single panel for presenting an EMR application to the user.

35. The system of claim 1 wherein the user interface layouts comprise a first user interface layout and a second user interface layout;

wherein the first user interface layout comprises three panels for presenting an EMR application, a healthcare visualization application, and a remote patient monitoring application to the user to the user; and wherein the second user interface layout comprises three panels for presenting the healthcare visualization application, a patient engagement application, and the remote patient monitoring application to the user.

36. A method for a unified experience exercising integrated viewing and control over a plurality of different computer applications and/or websites, the method comprising:

communicating over a network with a plurality of different computer applications and/or websites;

accessing a plurality of software instructions in a memory that define a user interface management application; and executing the accessed software instructions that define the user interface manager application to present a unified user interface experience that permits a user to view and interact with the different computer applications and/or websites that are combined via the software instructions for presentation through different portions of a user interface;

wherein the executing step comprises:

creating a plurality of different user interface layouts selectable by the user for display on a screen, wherein each user interface layout comprises at least one panel, and wherein each of a plurality of the user interface layouts comprises a plurality of panels; and managing a plurality of frame data structures to control which of the computer applications and/or websites are presented to the user through the panels of the user interface layouts, wherein each frame data structure is (1) associated with a corresponding computer application or website and (2) assignable via the user interface manager application to the panels of the user interface layouts, and wherein the frame data structures are concurrently persisting within the memory to retain states for their corresponding computer applications and/or websites even if their corresponding computer applications and/or websites are not presented through a currently displayed user interface layout; and wherein each panel of the currently displayed user interface layout (1) presents data from the computer application or website associated with a frame data structure assigned to that panel and (2) receives user input for delivery to its the computer application or website associated with the frame data structure assigned to that panel.

37. The method of claim 36 wherein the computer applications include an Electronic Medical Record (EMR) application, a care management application, a healthcare visualization application, a patient engagement application, and a remote patient monitoring application, and wherein different panels of the user interface layouts present the EMR application, the care management application, the healthcare visualization application, the patient engagement application, and the remote patient monitoring application.

38. The method of claim 36 wherein each concurrently persisting frame data structure identifies an address for its associated computer application or website.

39. The method of claim 36 wherein each concurrently persisting frame data structure has a display status of visible or hidden, and wherein the executing step further comprises:

controllably switching the concurrently persisting frame data structures between the visible status and the hidden status based on which of the user interface layouts is currently presented on the screen so that (1) each concurrently persisting frame data structure associated with a computer application or website and assigned to a panel of the currently presented user interface layout has the visible status while the other concurrently persisting frame data structures have the hidden status and (2) the currently presented user interface layout displays the retained state of each computer application and/or website corresponding to each concurrently persisting frame data structure with the visible status.

40. The method of claim 36 wherein the executing step further comprises:

presenting a selection interface through which the user creates a preset user interface layout, wherein the selection interface (1) prompts the user for input to define a number of panels to include in the preset user interface layout, (2) provides the user with a menu of available computer applications and/or websites for association with each panel of the preset user interface layout, and (3) receives input from the user corresponding to a selection of a computer application or website from the menu to associate with each panel of the preset user interface layout; and creating a preset user interface layout for inclusion among the user interface layouts in response to user inputs via the selection interface.

41. The method of claim 40 wherein the executing step further comprises:

creating a plurality of preset user interface layouts for inclusion among the user interface layouts in response to user inputs via the selection interface, wherein the preset user interface layouts include a plurality of single panel preset user interface layouts and a plurality of multi-panel preset user interface layouts; and including selectable buttons for accessing the single panel preset user interface layouts and the multi-panel preset user interface layouts on a toolbar of the currently displayed user interface layout.

42. The method of claim 36 wherein the created user interface layouts include a plurality of single panel user interface layouts for a plurality of single panel presets, wherein each single panel user interface layout comprises a single panel that is associated with a different computer application or website for presentation to the user, and wherein the executing step further comprises:

including a plurality of single panel preset buttons in a user interface toolbar, each single panel preset button corresponding to a different one of the single panel user interface layouts and being selectable by the user to switch the system to display the single panel user interface layout corresponding to the selected single panel preset button on the screen.

43. The method of claim 42 wherein the user interface toolbar includes a user-configurable number of the single panel preset buttons.

44. The method of claim 42 wherein the executing step further comprises:

creating the single panel presets by selecting the computer applications and/or website to be associated with the single panel presets from a menu of available computer applications and/or websites in response to user input that associates different ones of the single panel preset buttons with different corresponding computer applications and/or websites.

45. The method of claim 42 wherein the created user interface layouts further include a plurality of multi-panel user interface layouts for a plurality of multi-panel presets, wherein each multi-panel user interface layout comprises a plurality of panels where each panel is associated with a different computer application or website for presentation to the user, and wherein the executing step further comprises:

including a plurality of multi-panel preset buttons in the user interface toolbar, each multi-panel preset button corresponding to a different one of the multi-panel user interface layouts and being selectable by the user to switch the system to display the multi-panel user interface layout corresponding to the selected multi-panel preset button on the screen.

46. The method of claim 45 wherein the user interface toolbar includes a user-configurable number of the multi-panel preset buttons.

47. The method of claim 45 wherein the executing step further comprises:

creating the multi-panel presets by (1) selecting how many panels to include in each multi-panel user interface layout in response to user input and (2) selecting the computer applications and/or websites to be associated with the panels of the multi-panel presets from a menu of available computer applications and/or websites in response to user input.

48. The method of claim 45 wherein the currently displayed user interface layout comprises a multi-panel user interface layout that includes a toolbar in a top ribbon in a top portion of the multi-panel user interface layout that spans a plurality of the panels of the currently displayed user interface layout, and wherein the toolbar includes the single panel preset buttons and the multi-panel preset buttons.

49. The method of claim 36 wherein each of a plurality of the user interface layouts includes panels that have predefined associations with the computer applications and/or websites that are presented in those panels, wherein the predefined associations are defined in the memory by the software instructions.

50. The method of claim 36 wherein the executing step further comprises creating an initial user interface display for presentation to the user in response to a start of the user interface manager application for the user by:

determining the user;
identifying a plurality of computer applications that are available to the determined user, wherein a plurality of the concurrently persisting frame data structures are associated with the identified computer applications;

selecting a multi-panel user interface layout from among the user interface layouts;

populating the selected multi-panel user interface layout by assigning the concurrently persisting frame data structures that are associated with a plurality of the identified computer applications to the panels of the selected multi-panel user interface layout; and providing the selected and populated multi-panel user interface layout as the initial user interface display for presentation to the determined user on the screen.

51. The method of claim 50 wherein the selected multi-panel user interface layout is a preset multi-panel user interface layout for the determined user.

52. The method of claim 50 wherein the selected multi-panel user interface layout is a default multi-panel user interface layout.

53. The method of claim 36 wherein the executing step further comprises:

defining a parent browsing context corresponding to the currently displayed user interface layout, and wherein each concurrently persisting frame data structure serves as an embedded browsing context within the defined parent browsing context and has its own session history; and the user interface manager application retaining states for the computer applications and/or websites associated with the concurrently persisting frame data structures even if not currently displayed.

54. The method of claim 53 wherein the executing step further comprises:

handling a document object model (DOM) that manages the concurrently persisting frame data structures.

55. The method of claim 36 wherein the managing step comprises:

changing which of the concurrently persisting frame data structures are visible through the panels without requiring a reload of the computer applications and/or websites.

56. The method of claim 55 wherein the executing step further comprises:

swapping the computer applications in and out of the displayed user interface layouts through managing which of the concurrently persisting frame data structures have a visible status versus a hidden status, and wherein the retained state results in a computer application corresponding to a concurrently persisting frame data structure that changes from the hidden status to the visible status being displayed via the currently displayed user interface layout with the same information it was displaying prior to be swapped out.

57. The method of claim 36 wherein the executing step further comprises:

assigning the concurrently persisting frame data structures to the panels to associate the panels with corresponding computer applications and/or websites; and switching between different ones of the user interface layouts for current display on the screen in response to user inputs through the panels or a toolbar so that different ones of the displayed user interface layouts present different combinations of the computer applications and/or websites through their panels.

58. A computer program product for a unified experience exercising integrated viewing and control over a plurality of different computer applications and/or websites, the computer program product comprising:

code resident on a non-transitory computer-readable storage medium that is executable by a processor to cause the processor to present a unified user interface experience that permits a user to view and interact with the different computer applications and/or websites that are combined via the code for presentation through different portions of a user interface by:
    communicating over a network with a plurality of different computer applications and/or websites;
    creating a plurality of different user interface layouts selectable by the user for display on a screen, wherein each user interface layout comprises at least one panel, and wherein each of a plurality of the user interface layouts comprises a plurality of panels; and
    managing a plurality of frame data structures to control which of the computer applications and/or websites are presented to the user through the panels of the user interface layouts, wherein each frame data structure is (1) associated with a corresponding computer application or website and (2) assignable via the code to the panels of the user interface layouts, and wherein the frame data structures are concurrently persisting within the memory to retain states for their corresponding computer applications and/or websites even if their corresponding computer applications and/or websites are not presented through a currently displayed user interface layout; and
  wherein each panel of the currently displayed user interface layout (1) presents data from the computer application or website associated with a frame data structure assigned to that panel and (2) receives user input for delivery to the computer application or website associated with the frame data structure assigned to that panel.

\* \* \* \* \*